US012714504B2

(12) United States Patent
Spaelter et al.

(10) Patent No.: US 12,714,504 B2
(45) **Date of Patent: *Aug. 25, 2026**

(54) SURGICAL SYSTEMS AND METHODS FOR FACILITATING TISSUE TREATMENT

(71) Applicant: Stryker European Operations Limited, Carrigtwohill (IE)

(72) Inventors: Ulrich Spaelter, Schoellbronn (DE); Matthias Paulisch, Roggwil (CH); Fabian Huegle, March (DE); Rose Riemer, Langendorf (CH); Alexis Christen, Herzogenbuchsee (CH); Andreas Wiederkehr, Biel (CH); Katja Stucki, Baden (CH); Pierre-Luc Sylvestre, Grenchen (CH); Subash K. Mannanal, Grenchen Mahwah, NJ (US); Chulho Pak, Mahwah, NJ (US)

(73) Assignee: Stryker European Operations Limited, Carrigtwohill (IE)

( * ) Notice: Subject to any disclaimer, the term of this patent is extended or adjusted under 35 U.S.C. 154(b) by 87 days.

This patent is subject to a terminal disclaimer.

(21) Appl. No.: 18/796,488

(22) Filed: Aug. 7, 2024

(65) Prior Publication Data

US 2024/0390072 A1 Nov. 28, 2024

Related U.S. Application Data

(63) Continuation of application No. 17/728,129, filed on Apr. 25, 2022, which is a continuation of application
(Continued)

(51) Int. Cl.

| | |
|---|---|
| ***A61B 34/10*** | (2016.01) |
| ***A61B 17/17*** | (2006.01) |

(Continued)

(52) U.S. Cl.
CPC .......... *A61B 34/10* (2016.02); *A61B 17/1703* (2013.01); *A61B 90/361* (2016.02);
(Continued)

(58) Field of Classification Search
CPC ......... A61B 34/10; A61B 34/20; A61B 90/37; A61B 90/36; A61B 90/361; A61B 17/17; A61B 17/1703
See application file for complete search history.

(56) References Cited

U.S. PATENT DOCUMENTS

| | | |
|---|---|---|
| 4,356,624 A | 11/1982 | Coverstone et al. |
| 6,036,696 A | 3/2000 | Lambrecht et al. |

(Continued)

FOREIGN PATENT DOCUMENTS

| | | |
|---|---|---|
| CN | 102750418 B | 12/2015 |
| CN | 108186136 A | 6/2018 |

(Continued)

OTHER PUBLICATIONS

English language abstract and machine-assisted English translation for EP 1 470 791 B1 extracted from espacenet.com database on Nov. 17, 2021, 15 pages.

(Continued)

*Primary Examiner* — Christopher J Beccia
(74) *Attorney, Agent, or Firm* — Howard & Howard Attorneys PLLC

(57) ABSTRACT

A system for treating tissue of a patient's anatomy at a target site. A localizer generates location data associated with the anatomy. A display unit overlays visual content on the anatomy within a field of view observable by a user. A visualization program on a computing device generates a virtual reference frame, identifies viable and non-viable approaches for fixation elements to engage tissue and secure a stabilizer relative to the target site based on patient-specific
(Continued)

imaging data, arranges a virtual viability model within the virtual reference frame based on the location data and comprising viable portions associated with viable approaches and non-viable portions associated with non-viable approaches, and renders the virtual viability model in the visual content displayed by the display unit overlaid onto the anatomy within the field of view to assist the user in visualizing at least one of viable approaches and non-viable approaches.

20 Claims, 37 Drawing Sheets

Related U.S. Application Data

No. 16/784,414, filed on Feb. 7, 2020, now Pat. No. 11,337,761.

(60) Provisional application No. 62/802,265, filed on Feb. 7, 2019.

(51) Int. Cl.

| | |
|---|---|
| ***A61B 90/00*** | (2016.01) |
| *A61B 17/00* | (2006.01) |
| *A61B 17/56* | (2006.01) |

(52) U.S. Cl.

CPC ...... *A61B 90/37* (2016.02); *A61B 2017/0042* (2013.01); *A61B 2017/564* (2013.01); *A61B 2034/104* (2016.02); *A61B 2034/107* (2016.02); *A61B 2090/365* (2016.02)

(56) References Cited

U.S. PATENT DOCUMENTS

| | | | |
|---|---|---|---|
| 7,050,845 | B2 | 5/2006 | Vilsmeier |
| 7,077,847 | B2 | 7/2006 | Pusnik et al. |
| 7,147,643 | B2 | 12/2006 | Robioneck et al. |
| 7,311,710 | B2 | 12/2007 | Zander |
| 7,527,626 | B2 | 5/2009 | Lutz et al. |
| 7,648,508 | B2 | 1/2010 | Lutz et al. |
| 7,686,837 | B2 | 3/2010 | Gasser et al. |
| 7,799,062 | B2 | 9/2010 | Crozet |
| 8,118,810 | B2 | 2/2012 | Prien |
| 8,333,766 | B2 | 12/2012 | Edelhauser et al. |
| 8,675,939 | B2 | 3/2014 | Moctezuma de la Barrera |
| 8,709,014 | B2 | 4/2014 | Ammann |
| 8,834,467 | B2 | 9/2014 | Singh et al. |
| 8,864,802 | B2 | 10/2014 | Schwager et al. |
| 8,886,496 | B2 * | 11/2014 | Graumann ............ A61B 34/10 703/1 |
| 8,945,128 | B2 | 2/2015 | Singh et al. |
| 8,951,252 | B2 | 2/2015 | Steiner et al. |
| 9,008,757 | B2 | 4/2015 | Wu |
| 9,011,438 | B2 | 4/2015 | Steiner et al. |
| 9,050,151 | B2 | 6/2015 | Schilter |
| 9,107,678 | B2 | 8/2015 | Murner et al. |
| 9,107,709 | B2 | 8/2015 | Wieland et al. |
| 9,339,315 | B2 | 5/2016 | Schwager et al. |
| 9,508,149 | B2 | 11/2016 | Simon et al. |
| 9,855,104 | B2 | 1/2018 | Blau et al. |
| 9,987,093 | B2 | 6/2018 | Christian et al. |
| 9,993,273 | B2 | 6/2018 | Moctezuma de la Barrera et al. |
| 10,070,903 | B2 | 9/2018 | Blau |
| 10,082,384 | B1 | 9/2018 | Singh |
| 10,123,830 | B2 | 11/2018 | Von Wieding et al. |
| 10,194,993 | B2 * | 2/2019 | Roger ................ A61B 17/1757 |
| 10,548,667 | B2 | 2/2020 | Flett et al. |
| 10,702,343 | B2 | 7/2020 | Kozak et al. |
| 10,786,287 | B2 | 9/2020 | Beger et al. |
| 10,980,578 | B2 | 4/2021 | Beger et al. |
| 11,337,761 | B2 * | 5/2022 | Spaelter ................ A61B 34/10 |
| 2005/0137599 | A1 | 6/2005 | Masini |
| 2012/0130686 | A1 | 5/2012 | Graumann |
| 2013/0218007 | A1 * | 8/2013 | Petteys ................. A61B 34/20 600/424 |
| 2016/0143663 | A1 | 5/2016 | Schemitsch et al. |
| 2016/0166335 | A1 | 6/2016 | Roger et al. |
| 2016/0191887 | A1 | 6/2016 | Casas |
| 2017/0164987 | A1 | 6/2017 | Dominik et al. |
| 2017/0181780 | A1 | 6/2017 | Cremer et al. |
| 2017/0215931 | A1 | 8/2017 | Cremer et al. |
| 2017/0281233 | A1 | 10/2017 | Edelhauser et al. |
| 2018/0055573 | A1 | 3/2018 | Rueber et al. |
| 2018/0110545 | A1 | 4/2018 | Bush, Jr. |
| 2018/0168691 | A1 | 6/2018 | Singh |
| 2018/0199999 | A1 | 7/2018 | Syverson et al. |
| 2018/0214181 | A1 | 8/2018 | Mannanal |
| 2018/0221056 | A1 | 8/2018 | Edelhauser et al. |
| 2018/0228514 | A1 | 8/2018 | Mannanal et al. |
| 2018/0325566 | A1 | 11/2018 | Blau |
| 2018/0333207 | A1 | 11/2018 | Moctezuma De la Barrera |
| 2018/0344406 | A1 | 12/2018 | Frank et al. |
| 2020/0253666 | A1 | 8/2020 | Spaelter et al. |
| 2022/0241021 | A1 | 8/2022 | Spaelter et al. |

FOREIGN PATENT DOCUMENTS

| | | | |
|---|---|---|---|
| DE | 102015102768 | A1 | 9/2016 |
| DE | 102015102776 | A1 | 9/2016 |
| DE | 102016115605 | A1 | 3/2018 |
| EP | 1321105 | B1 | 8/2003 |
| EP | 1470791 | B1 | 2/2007 |
| EP | 3081184 | B1 | 1/2019 |
| EP | 3858280 | A1 | 8/2021 |
| WO | 9804203 | A2 | 2/1998 |
| WO | 9832388 | A2 | 7/1998 |
| WO | 2018049196 | A1 | 3/2018 |
| WO | 2019141704 | A1 | 7/2019 |
| WO | 2019204699 | A1 | 10/2019 |

OTHER PUBLICATIONS

English language abstract for EP 1 321 105 B1 extracted from espacenet.com database on Nov. 17, 2021, 2 pages.

Machine-assisted English language abstract for DE 10 2015 102 768 A1 extracted from espacenet.com database on Nov. 17, 2021, 3 pages.

Machine-assisted English language abstract for DE 10 2015 102 776 A1 extracted from espacenet.com database on Nov. 17, 2021, 4 pages.

Machine-assisted English language abstract for DE 10 2016 115 605 A1 extracted from espacenet.com database on Nov. 17, 2021, 2 pages.

Stryker, "AxSOS 3 Titanium Monoaxial Locking Plate System Brochure", 2015, 20 pages.

* cited by examiner

SURGICAL SYSTEMS AND METHODS FOR FACILITATING TISSUE TREATMENT

CROSS-REFERENCE TO RELATED APPLICATIONS

This application is a Continuation of U.S. patent application Ser. No. 17/728,129 filed on Apr. 25, 2022, which is a Continuation of U.S. patent application Ser. No. 16/784,414 filed on Feb. 7, 2020 and issued as U.S. Pat. No. 11,337,761 on May 24, 2022, which claims priority to and all the benefits of U.S. Provisional Patent Application No. 62/802,265 filed on Feb. 7, 2019, the disclosures of each of which are hereby incorporated by reference in their entirety.

TECHNICAL FIELD

The present disclosure relates, generally, to surgical systems and, more specifically, to surgical systems and methods for facilitating tissue treatment.

BACKGROUND

Conventional medical and surgical procedures routinely involve the stabilization of tissue at a target site in order to, among other things, limit or otherwise prevent relative movement between portions of a patient's anatomy to help promote tissue healing. By way of illustrative example, conventional orthopedic surgical interventions frequently involve securing adjacent portions of bone tissue to each other to heal fractures, correct deformities, and/or repair joints in order to help improve patient mobility, reduce pain, mitigate the risk of subsequent injury or damage, and the like. To this end, surgeon may utilize one or more types of surgical tools (e.g., saws, drills, milling devices, reduction instrumentation, and the like) to facilitate approaching, manipulating, or otherwise effecting treatment of the target site by inserting anchors, screws, pins, and/or wires into each of the portions of bone tissue and also to one or more rigid components such as plates, rods, implants, and/or frames in order to fix the portions of bone tissue relative to each other.

In many types of orthopedic surgical interventions, the surgeon orientates the portions of bone tissue relative to each other according to a preoperative surgical plan based on one or more types of patient-specific imaging of the target site (e.g., obtained via X-ray, CT-scan, MRI, ultrasonography, fluoroscopy, and the like). While preoperative imaging is generally used both for diagnosis and surgical planning, intraoperative imaging may also be used in order to refine and/or verify execution of one or more steps of the surgical plan. For example, the surgeon may rely on fluoroscopy during intraoperative fracture reduction, implant trialing, and/or tissue penetration in order to help visualize one or more unexposed portions of target site. Here too, the surgeon may rely on fluoroscopy to visualize surgical tools, implants, anchors, and the like relative to the target site which are otherwise obstructed from the surgeon's field of view by portions of the patient's anatomy. It will be appreciated that the use of fluoroscopy allows the surgeon to visualize tissue and objects at the target site in "near real-time" without necessitating that the surgeon make excessively large incisions that might otherwise be required to allow the surgeon to directly view the target site. However, it is also desirable to minimize the amount of radiation that the patient is exposed to during a surgical intervention.

In certain surgical procedures, a navigation system (or, "tracking system") may also be utilized during execution of the surgical plan in order to assist surgeons in, guiding, positioning, and/or moving surgical tools, instrumentation, prostheses, implants, anchors, hardware, and the like relative to the target site with enhanced accuracy and precision. To this end, the navigation system generally tracks states of the surgical tool and also tracks states of one or more patient trackers attached to the patient's anatomy relative to the target site, both of which may move during the surgical procedure. Navigation systems may comprise a number of different types and/or configurations, and are used in connection with both hand-held surgical tools and surgical tools which are coupled to robotic manipulators.

While the use of navigation systems generally affords opportunities for executing surgical procedures with enhanced accuracy and precision, it will be appreciated that certain types of surgical procedures are less suitable for their utilization, such as where the target site is difficult to approach, involves complex tissue geometry, involves a revision of a previous procedure, and/or involves an emergency surgical intervention. By way of non-limiting example, orthopedic surgical interventions that involve repairing comminuted fractures and/or periprosthetic fractures can significantly complicate the utilization of certain types of navigation systems during various steps of the surgical procedure. These types of orthopedic surgical interventions can also make tissue stabilization extremely difficult with certain types of implants, anchors, and the like based on their geometry relative to the arrangement of the bone tissue portions following and/or during fracture reduction.

Accordingly, there remains a need in the art to address at least the aforementioned issues.

SUMMARY

The present disclosure provides a surgical system for use in treating tissue of a patient's anatomy at a target site, with a stabilizer and a fixation element, based on patient-specific imaging data. The surgical system includes a localizer to generate patient location data associated with a location of at least a portion of the patient's anatomy. A display unit is provided to display visual content overlaid onto the patient's anatomy within a field of view observable by a user. A computing device is coupled to the localizer and the display unit. The computing device comprises one or more processors and a non-transitory storage medium having stored thereon a visualization program. When executed by the one or more processors, the visualization program is configured to generate a virtual reference frame. When executed by the one or more processors, the visualization program is further configured to identify a plurality of different fixation approaches for the fixation element to engage tissue and secure the stabilizer relative to the target site. The plurality of different fixation approaches are delineated between one or more viable fixation approaches and one or more non-viable fixation approaches based on the patient-specific imaging data. When executed by the one or more processors, the visualization program is further configured to arrange a virtual viability model within the virtual reference frame based on the patient location data. The virtual viability model comprises at least one of: one or more viable portions associated with the viable fixation approaches, and one or more non-viable portions associated with the non-viable fixation approaches. When executed by the one or more processors, the visualization program is further configured to render at least a portion of the virtual viability model in the visual content displayed by the display unit overlaid onto the patient's anatomy within the field of view to assist the user in visualizing at least one of: the one or more viable fixation approaches, and the one or more non-viable fixation approaches.

The present disclosure also provides a method of treating tissue of a patient's anatomy at a target site, with a stabilizer and a fixation element, based on patient-specific imaging data. The method comprises generating patient location data associated with a location of at least a portion of the patient's anatomy. The method also comprises identifying a plurality of different fixation approaches for the fixation element to engage tissue and secure the stabilizer relative to the target site, with the plurality of different fixation approaches delineated between one or more viable fixation approaches and one or more non-viable fixation approaches based on the patient-specific imaging data. The method also comprises arranging a virtual viability model within a virtual reference frame based on the patient location data, the virtual viability model comprising at least one of: one or more viable portions associated with the viable fixation approaches, and one or more non-viable portions associated with the non-viable fixation approaches. The method also comprises providing a display unit to display visual content overlaid onto the patient's anatomy within a field of view observable by a user. The method also comprises rendering at least a portion of the virtual viability model in the visual content displayed by the display unit overlaid onto the patient's anatomy within the field of view to assist the user in visualizing at least one of: the one or more viable fixation approaches, and the one or more non-viable fixation approaches.

Other features and advantages of the embodiments of the present disclosure will be readily appreciated, as the same becomes better understood, after reading the subsequent description taken in conjunction with the accompanying drawings.

DETAILED DESCRIPTION OF THE EMBODIMENTS

Figure 1:
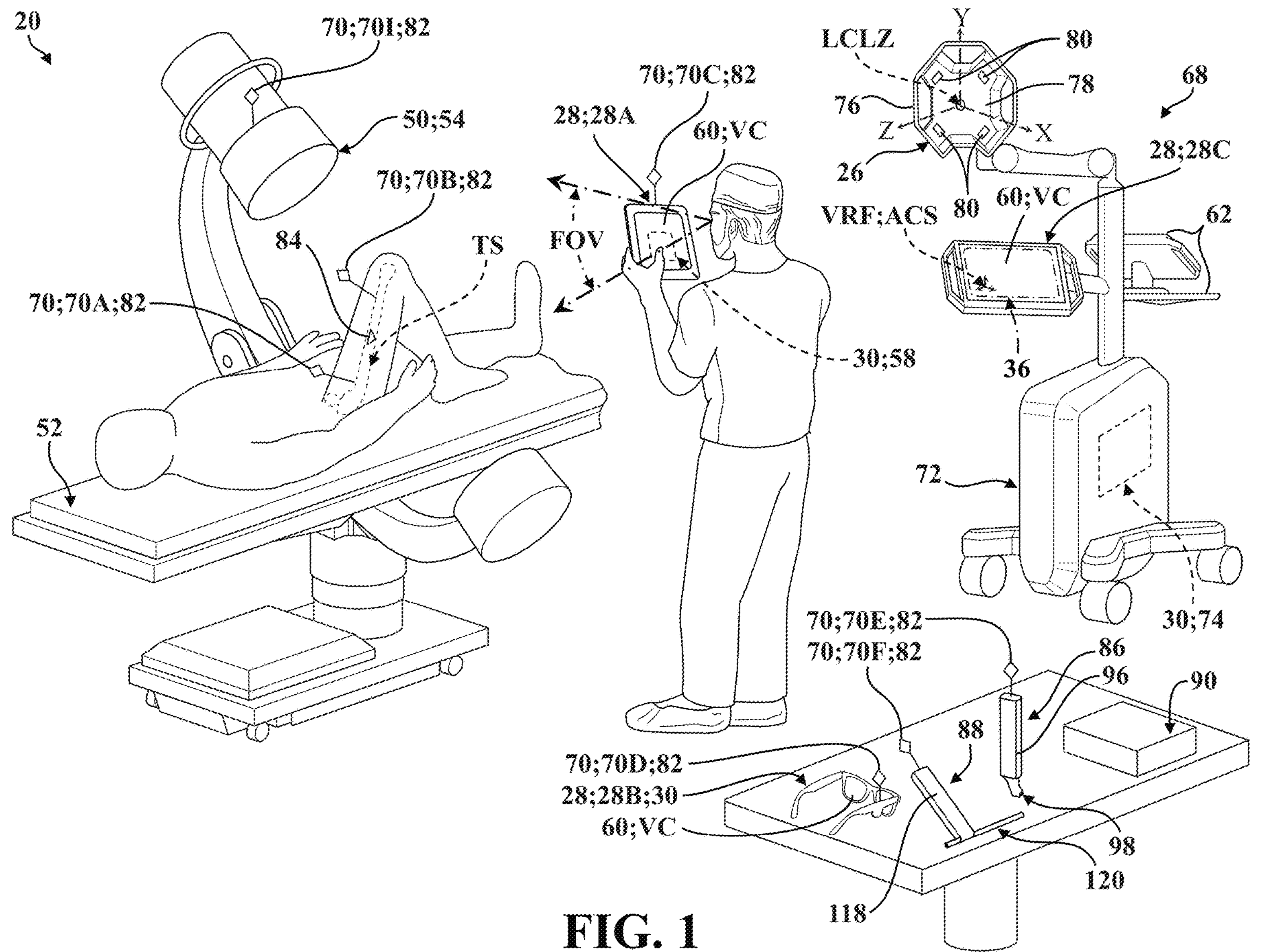
FIG. 1 is a perspective view of a surgical system for use in treating tissue of a patient's anatomy at a target site, shown depicting a computing device, a navigation system comprising a localizer and trackers, a plurality of display units to display visual content to a user, and a plurality of surgical instruments including a handle assembly, a guide assembly, and a stabilization kit.

With reference now to the drawings, wherein like numerals indicate like parts throughout the several views, embodiments of a surgical system 20 and computer-implemented techniques and methods associated with the surgical system 20 are generally shown in FIGS. 1-10F. The various embodiments of the present disclosure are directed toward assisting a user (e.g., a surgeon) in treating tissue of a patient's anatomy at a target site TS that is the subject of a surgical procedure, with at least one stabilizer 22 and at least one fixation element 24, based on patient-specific imaging data ID. To this end, and as is described in greater detail below, the representative embodiment of the surgical system 20 illustrated throughout the drawings generally comprises one or more localizers 26, display units 28, and computing devices 30 (see FIGS. 1-2). The localizer 26 is configured to generate patient location data PLD associated with a location of at least a portion of the patient's anatomy. The display unit 28 is configured to display visual content VC overlaid onto the patient's anatomy within a field of view FOV observable by the user. As is depicted schematically in FIG. 2, the computing device 30 is coupled to the localizer 26 and to the display unit 28, and comprises one or more processors 32 and a non-transitory storage medium, such as a memory device 34, on which a visualization program 36 is stored.

When executed by the one or more processors 32, the visualization program 36 is configured to, among other things, generate a virtual reference frame VRF and identify a plurality of different fixation approaches 38 for the fixation element 24 to engage tissue and secure the stabilizer 22 relative to the target site TS, with the plurality of different fixation approaches 38 delineated between one or more viable fixation approaches 40 and one or more non-viable fixation approaches 42 based on the patient-specific imaging data ID. The visualization program 36 is further configured to arrange a virtual viability model 44 within the virtual reference VRF based on the patient location data PLD. The virtual viability model comprises at least one of: one or more viable portions 46 associated with viable fixation approaches 40; and one or more non-viable portions 48 associated with non-viable fixation approaches 42. Here, the visualization program 36 is configured to render at least a portion of the virtual viability model 44 in the visual content VC displayed by the display unit 28 overlaid onto the patient's anatomy within the field of view FOV to assist the user in visualizing at least one of: one or more viable fixation approaches 40 represented by viable portions 46 of the virtual viability model 44; and one or more non-viable fixation approaches 42 represented by non-viable portions 48 of the virtual viability model 44. Each of the components of the surgical system 20 introduced above will be described in greater detail below.

Referring now to FIG. 1, an operating room is illustrated in which a patient is undergoing an exemplary surgical procedure performed using aspects of the surgical system 20, the visualization program 36, and the various methods and computer-implemented techniques of the present disclosure. In the representative examples described herein and illustrated throughout the drawings, the target site TS generally comprises portions of the patient's femur, including without limitation discrete portions of the femur delineated by comminuted fractures (see FIGS. 4A-4D), and discrete portions of the femur delineated by a diaphyseal periprosthetic fracture (see FIGS. 5A-10F). However, it will be appreciated that the target site TS could comprise any suitable portion of the patient's anatomy for a given surgical procedure, including portions of other bones, portions of one or more adjacent bones, and/or various other types of tissue, as described in greater detail below. Moreover, it will be appreciated that the surgical system 20, the visualization program 36, and the various methods and computer-implemented techniques of the present disclosure can be utilized to facilitate visualizing fixation approaches 38 in connection with a number of different types of medical and/or surgical procedures beyond orthopedic procedures directed toward treating fractured bone tissue at the target site TS. Other configurations are contemplated.

As used herein, the term "fixation approaches 38" refers to one or more discrete linear or non-linear paths (e.g., penetration trajectories PT) along which various types of fixation elements 24 may be installed, implanted, or otherwise moved along into engagement with tissue, with "viable fixation approaches 40" referring to fixation approaches 38 along which a particular fixation element 24 may be moved along into engagement with tissue, and with "non-viable fixation approaches 42" referring to fixation approaches 38 along which a particular fixation element 24 cannot be moved along into engagement with tissue. As will be appreciated from the subsequent description of FIGS. 5A-10F below, the visualization program 36 may delineate identified fixation approaches 38 into non-viable fixation approaches 42 based on a number of factors, including without limitation potential damage to certain types of tissue (e.g., soft tissue), potential collision with stabilizers 22, other fixation elements 24, other implants, and the like. Other configurations are contemplated.

Figure 2:
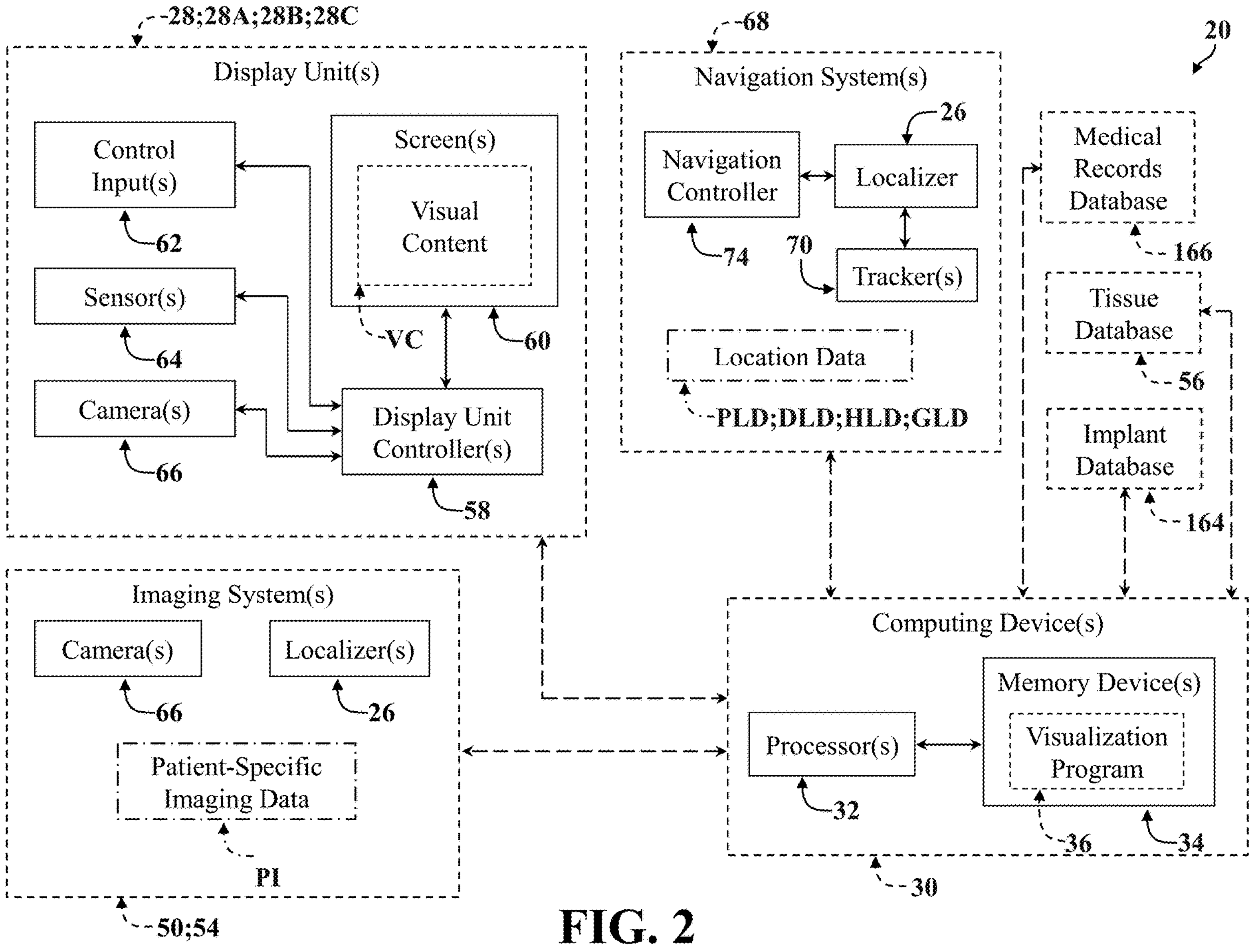
FIG. 2 is a block diagram illustrating general communication between the computing device and other components of the surgical system of FIG. 1, the computing device shown having a memory device with a visualization program stored thereon according to one embodiment of the present disclosure.

Referring now to FIGS. 1-2, as noted above, the surgical system 20, the visualization program 36, and the various methods and computer-implemented techniques of the present disclosure utilize patient-specific imaging data ID to, among other things, facilitate assisting the user in visualizing viable fixation approaches 40 and/or non-viable fixation approaches 42 represented by the virtual viability model 44 rendered in the visual content VC displayed, by the one or more display units 28, overlaid onto the patient's anatomy within the field of view FOV. To this end, and as is depicted schematically in FIG. 2, the patient-specific imaging data ID can be generated using one or more types of imaging systems 50 which are configured to perform medical imaging techniques such as radiography (e.g., static X-ray imaging and/or fluoroscopy), computed tomography (e.g., a "CT scan"), magnetic resonance imaging (MRI), ultrasonography, near-infrared (NIR) fluorescence, Terahertz radiation, and the like. Other configurations are contemplated.

It will be appreciated that the patient-specific imaging data ID may comprise various forms and/or formats, generated or otherwise collected from one or more imaging systems 50, preoperatively and/or intraoperatively. By way of illustrative example, FIG. 1 shows the patient positioned on a patient support apparatus 52 adjacent to an imaging system 50 realized as a C-arm imaging system 54 which is configured to intraoperatively collect images via fluoroscopy that may be used to, among other things, generate one or more types of patient-specific imaging data ID.

In some embodiments, images collected by the imaging system 50, either preoperatively or intraoperatively, may be translated, compiled, arranged, augmented, or otherwise put into a format that can be interpreted by the visualization program 36 (or one or more other components of the surgical system 20) as patient-specific imaging data ID. Here, for example, images collected with imaging systems 50 may be directly communicated to the computing device 30 such that the visualization program 36 (or another program stored on the memory device 34) could generate the patient-specific imaging data ID based on those images. However, it is also contemplated that the imaging system 50 (or another intermediary computing device) could at least partially translate images into other forms which define the patient-specific imaging data ID (e.g., represented by a 3D model generated by combining several image segments). Thus, the patient-specific imaging data ID could be generated directly by the visualization program 36 (e.g., by translating images received from the imaging system 50 into patient-specific imaging data ID) or could be generated externally and interpreted by the visualization program 36 (e.g., by receiving patient-specific imaging data ID pre-translated by the imaging system 50 or by another intermediary computing device). Other configurations are contemplated.

In some embodiments, the patient-specific imaging data ID may comprise one or more 2D images (e.g., via X-ray imaging) of the patient's anatomy, 3D renderings or models generated based on 2D images of the patient's anatomy (e.g., via MRI imaging segmentation), and/or point clouds or surface maps of the patient's anatomy (e.g., via ultrasonography). Other configurations are contemplated. As is described in greater detail below in connection with FIGS. 4A-4D, the patient-specific imaging data ID may be generated based on imaging (e.g., via the imaging system 50) of the target site TS and/or at other portions of the patient's anatomy. Furthermore, the patient-specific imaging data ID may be generated, refined, or otherwise based on one or more tissue databases 56 (see FIG. 2; depicted schematically) comprising one or more statistical models, datasets, and the like generated based on a sample population (e.g., complied from previously-generated data associated with a number of different patients). Here, the tissue database 56 may comprise "generalized" patient data that can be adjusted based on certain patient-specific attributes to generate or otherwise define the patient-specific imaging data ID. By way of illustrative example, measurements taken between anatomical landmarks of the patient's anatomy (e.g., measured preoperatively on an x-ray image or measured intraoperatively at the exposed target site TS) could serve as input variables that are compared against the tissue database 56 to generate a 3D model serving as the patient-specific imaging data ID based on only a limited number of patient-specific measurements. Other configurations are contemplated.

With continued reference to FIGS. 1-2, a total of three different types of display units 28 are shown as examples: a tablet display unit 28A, a head-mountable display unit 28B, and a navigation display unit 28C, each of which are described in greater detail below. As is depicted schematically in FIG. 2, the display units 28 may each comprise a display unit controller 58 disposed in communication with a screen 60 configured to display the visual content VC to assist the user in visualizing the fixation approaches 38, as noted above and as is described in greater detail below.

In some embodiments, the display unit controller 58 serves as or otherwise defines the computing device 30, the one or more processors 32, and the memory device 34 on which the visualization program 36 is stored. Irrespective of which component of the surgical system 20 defines the computing device 30, the processor 32 may include a microprocessor, a microcontroller, an integrated circuit, and the like. The memory device 34 is a non-transitory computer-readable storage medium that stores computer-readable and executable instructions embodied in one or more programs or modules. The memory device 34 may include, for example, non-volatile memory such as a hard disk or flash memory, and may also include random access memory (RAM), which can include non-volatile RAM (NVRAM), magnetic RAM (MRAM), ferroelectric RAM (FeRAM), or any other suitable memory.

The display units 28 may also comprise one or more control inputs 62 arranged for engagement by the user to, among other things, operate the visualization program 36 (e.g., via a graphical user interface rendered as a portion of the visual content VC displayed on the screen 60). It will be appreciated that control inputs 62 could be configured in a number of different ways sufficient to be actuated by the user (e.g., with buttons, triggers, switches, knobs, levers, touchscreens, and the like). In some embodiments, the display units may comprise one or more sensors 64 in communication with the display unit controller 58 (e.g., inertial sensors such as accelerometers, gyroscopes, and the like). In some embodiments, one or more of the display units 28 may comprise a camera 66 in communication with the display unit controller 58. Here, the sensors 64 and/or camera(s) 66 could be used to collect data during the surgical procedure which are utilized later (e.g., for report generation). By way of illustrative example, the sensors 64 and/or camera(s) 66 could record images, audio, and/or video to document the surgical procedure, to facilitate registering (or confirming registration of) article/lot numbers of various stabilizers 22 and/or fixation elements 24 used (e.g., for the patient's record), and overall promote improved logistics. Other configurations are contemplated.

Furthermore, the camera 66 may be configured to capture images, video, and the like, which may form portions of the visual content VC displayed on the screen 60. By way of non-limiting example, the tablet display unit 28A may be configured such that the camera 66 faces away from the screen 60 to capture video within the field of view FOV in "near real-time" to facilitate displaying the visual content VC overlaid onto the patient's anatomy with augmented reality and/or mixed reality (see FIGS. 3A-3C and 4B-4D), where the screen 60 itself is positioned within the user's field of view FOV. In some embodiments, the camera 66 may serve as one or more of an imaging system 50 and/or a localizer 26 (e.g., based on optical tracking methodologies) in order to, among other things, dynamically relate the pose of the display unit 28 to the pose of tracked objects imaged by the camera 66 (e.g., so as to generate the patient location data PLD). The head-mountable display unit 28B may be provided with a "semi-transparent" screen 60 configured such that the user can see through the screen 60 to facilitate displaying the visual content VC overlaid onto the patient's anatomy with augmented reality and/or mixed reality (see FIGS. 4D, 5B-7D, 8C-10A, and 10C-10E). It is contemplated that other types of display units 28 may be employed to display visual content VC overlaid onto the patient's anatomy within the field of view FOV, such as with a projector configured to display the visual content VS as light emitted onto the target site TS, other types of portable electronic devices (e.g., tablet computers, mobile phones), other types of head-mountable display units, and the like. Other configurations are contemplated.

As noted above, the localizer 26 is disposed in communication with the computing device 30 and is employed to generate the patient location data PLD associated with a location of at least a portion of the patient's anatomy in order to, among other things, facilitate rendering the virtual viability model 44 in the visual content VC displayed by the one or more display units 28 overlaid onto the patient's anatomy within the field of view FOV observable by the user. To this end, the representative embodiment of the localizer 26 illustrated in FIG. 1 forms part of a navigation system, generally indicated at 68, which is configured to sense, track, or otherwise monitor the position and/or orientation (e.g., the "pose") of one or more trackers 70 within a localizer coordinate system LCLZ based, for example, on the relative poses of respective tracker coordinate systems (not shown) in the localizer coordinate system LCLZ. In some embodiments, the localizer 26 monitors the trackers 70 to determine a state of each of the trackers 70 which corresponds to the state of the object respectively attached thereto. Here, the navigation controller 74 gathers data (e.g., location data) about tracked states of each tracker 70 monitored by the localizer 26 within the localizer coordinate system LCLZ. As used herein, the term "tracked state" includes, but is not limited to, data which represents or defines the position and/or orientation of a tracked object, and/or equivalents or derivatives of the position and/or orientation. For example, a tracked state may be a pose of the tracked object, and may include linear data, angular velocity data, and the like. Other configurations are contemplated.

For the illustrative purposes of clarity and consistency, trackers 70 are shown throughout the drawings as being firmly affixed to different objects that may be tracked by the navigation system 68 in certain embodiments, including first and second patient trackers 70A, 70B, first and second display unit trackers 70C, 70D, first and second instrument trackers 70E, 70F, first and second stabilizer trackers 70G, 70H (see FIGS. 10E-10F), and an imaging system tracker 70I, each of which will be discussed in greater detail below.

As is depicted in FIG. 1, the illustrated navigation system 68 includes a cart assembly 72 that houses a navigation controller 74 which is disposed in communication with the localizer 26, the one or more display units 28 (e.g., the navigation display unit 28C), the computing device 30, and the one or more control inputs 62. The navigation system 68 and/or trackers 70 could be configured in way similar to as is disclosed in one or more of: U.S. Pat. No. 9,008,757, entitled "Navigation System Including Optical and Non-Optical Sensors;" and U.S. Pat. No. 9,993,273, entitled "Bone Plate and Tracking Device Using a Bone Plate for Attaching to a Patient's Anatomy," the disclosures of each of which are hereby incorporated by reference. Other configurations are contemplated, including without limitation those disclosed in other publications referenced herein.

The navigation controller 74 may be of a number of different styles, types, or configurations, and may also be disposed in communication with other components of the surgical system 20. In some embodiments, the navigation controller 74 may comprise the computing device 30. Communication between the navigation controller 74 and the various other components of the surgical system 20 may be realized with one or more types of electrical communication, such as via physical electrical connections (e.g., a tethered wire harness) and/or via one or more types of wireless communication (e.g., with a WiFi™ network, Bluetooth®, a radio network, and the like). Other configurations are contemplated.

The control inputs 62 may also form part of the illustrated navigation system 68, such as to facilitate operating a navigation interface (not shown) via the navigation display unit 28C which, in some embodiments, may similarly be configured to facilitate operating the visualization program 36. To this end, control inputs 62 associated with the navigation system 68 depicted in FIG. 1 may comprise interactive touchscreens coupled directly to one or more navigation display units 28C, and may also include any one or more of a keyboard, a mouse, a microphone (e.g., for voice-activation), a gesture-based control device, and the like. Other configurations are contemplated.

In the illustrated embodiment, the navigation controller 74 communicates the tracked states of one or more of the trackers 70 to the computing device 30 implementing the visualization program 36 (depicted schematically in FIG. 2), which can be used to, among other things, arrange various virtual models within the virtual reference frame VRF based on data associated with different tracked objects, as described in greater detail below. In the representative embodiment illustrated herein, the tracked states of the one or more patient trackers 70A, 70B coupled to tissue adjacent to the target site TS comprise the patient location data PLD utilized to facilitate arranging the virtual viability model 44 within the virtual reference frame VRF. Here too, the tracked states of other trackers 70 may similarly be used to facilitate arranging other virtual models within the virtual reference frame VRF based on location data relating to other tracked objects.

In the illustrated embodiment, the localizer 26 is an optical localizer and includes a camera unit 76 with an outer casing 78 that houses one or more optical sensors 80 configured to sense movement of the various trackers 70. To this end, any one or more of the trackers 70 may include active markers 82 (not shown in detail). The active markers 82 may include light emitting diodes (LEDs). Alternatively, the trackers 70 may have passive markers, such as reflectors which reflect light emitted from the camera unit 76 or another predetermined light source. Other suitable markers not specifically described herein may be utilized.

Although one embodiment of the navigation system 68 is illustrated throughout the drawings, the navigation system 68 may have any other suitable configuration for monitoring trackers 70 which, as will be appreciated from the subsequent description below, may be of various types and configurations. For example, the navigation system 68 may comprise other types of localizers 26 and/or trackers 70.

In some embodiments, the navigation system 68 and/or the localizer 26 are radio frequency (RF) based. For example, the navigation system 68 may comprise an RF transceiver coupled to the navigation controller 74 and/or to the computing device 30. Here, the trackers 70 may comprise RF emitters or transponders, which may be passive or may be actively energized. The RF transceiver transmits an RF tracking signal, and the RF emitters respond with RF signals such that tracked states are communicated to (or interpreted by) the navigation controller 74. The RF signals may be of any suitable frequency. The RF transceiver may be positioned at any suitable location to track the objects using RF signals effectively. Furthermore, it will be appreciated that embodiments of RF-based navigation systems may have structural configurations that are different than the navigation system 68 illustrated throughout the drawings.

In some embodiments, the navigation system 68 and/or localizer 26 are electromagnetically (EM) based. For example, the navigation system 68 may comprise an EM transceiver coupled to the navigation controller 74 and/or to the computing device 30. Here, the trackers 70 may comprise EM components attached thereto (e.g., various types of magnetic trackers, electromagnetic trackers, inductive trackers, and the like), which may be passive or may be actively energized. The EM transceiver generates an EM field, and the EM components respond with EM signals such that tracked states are communicated to (or interpreted by) the navigation controller 74. The navigation controller 74 may analyze the received EM signals to associate relative states thereto. Here too, it will be appreciated that embodiments of EM-based navigation systems may have structural configurations that are different than the navigation system 68 illustrated throughout the drawings.

In some embodiments, the navigation system 68 and/or the localizer 26 could be based on one or more types of imaging systems 50 that do not necessarily require trackers 70 to be fixed to objects in order to determine location data associated therewith. For example, an ultrasound-based imaging system 50 coupled to the navigation controller 74 and/or to the computing device 30 could be provided to facilitate acquiring ultrasound images (e.g., of specific known structural features of tracked objects, of markers or stickers secured to tracked objects, and the like) such that tracked states are communicated to (or interpreted by) the navigation controller 74 based on the ultrasound images. The ultrasound images may be 2D, 3D, or a combination thereof. The navigation controller 74 may process ultrasound images in near real-time to determine the tracked states. The ultrasound imaging device may have any suitable configuration and may be different than the camera unit 76 as shown in FIG. 1. By way of further example, a fluoroscopy-based imaging system 50 (e.g., the C-arm imaging system 54 illustrated in FIG. 1) coupled to the navigation controller 74 and/or to the computing device 30 could be provided to facilitate acquiring X-ray images of radio-opaque markers 84 (e.g., stickers, tags, and the like with known structural features that are attached to tracked objects) such that tracked states are communicated to (or interpreted by) the navigation controller 74 based on the X-ray images. Put differently, various types of imaging systems 50 could define the localizer 26 and/or form a part of the navigation system 68 without departing from the scope of the present disclosure. Furthermore, it will be appreciated that various arrangements of trackers 70 are depicted throughout the drawings for illustrative purposes, and it is contemplated that the navigation system 68 (as well as various other parts of the surgical system 20) could track certain types of objects without necessarily requiring the use of each tracker 70 illustrated throughout the drawings.

Those having ordinary skill in the art will appreciate that the navigation system 68 and/or localizer 26 may have any other suitable components or structure not specifically recited herein. Furthermore, any of the techniques, methods, and/or components described above with respect to the camera-based navigation system 68 shown throughout the drawings may be implemented or provided for any of the other embodiments of the navigation system 68 described herein. For example, the navigation system 68 may utilize solely inertial tracking or any combination of tracking techniques.

As noted above, various trackers 70 are illustrated throughout the drawings as being secured to certain tracked objects monitored by the localizer 26. In FIGS. 1 and 5A-10F, the first patient tracker 70A and the second patient tracker 70B are shown attached to different tissue portions of the patient's anatomy (here, to different portions of the femur). Thus, the localizer 26 can determine the relative poses of different tissue portions based on tracked states of the first and second patient trackers 70A, 70B. Furthermore, in FIG. 1, the first display unit tracker 70C and the second display unit tracker 70D are shown attached, respectively, to the tablet display unit 28A and the head-mountable display unit 28B. Thus, the localizer 26 can determine the relative poses of the tablet display unit 28A and the head-mountable display unit 28B based on tracked states of the first and second display unit trackers 70C, 70D. Here, because tracked states of the first and second patient trackers 70A, 70B and the first and second display unit trackers 70C, 70D can all be determined within the localizer coordinate system LCLZ, the arrangement of one or both of the different tissue portions can be also determined relative to one or both of the tablet display unit 28A and the head-mountable display unit 28B. In this way, the computing device 30 can arrange the virtual viability model 44 within the virtual reference frame VRF relative to the pose of whichever display unit 28 is being used to display the visual content VC overlaid onto the patient's anatomy within the field of view FOV to assist the user in visualizing fixation approaches 38. Furthermore, as described in greater detail below, the computing device 30 can facilitate arranging virtual objects associated with different tissue portions within the virtual reference frame VRF which, when rendered in the visual content VC, can assist the user in visualizing various aspects of the target site that might not otherwise be observable within the field of view FOV.

In FIGS. 1, 6A-6E, and 8A-8E, the first instrument tracker 70E is shown attached to a handle assembly 86 which, as described in greater detail below, is configured to releasably attach to certain types of stabilizers 22 to afford the user with improved handling of the stabilizer 22. Thus, the localizer 26 can determine the relative pose of the handle assembly 86 (and, thus, an attached stabilizer 22) based on tracked states of the first instrument tracker 70E. Here too, because the tracked states of the first instrument tracker 70E and other monitored trackers 70 (e.g., the first and second patient trackers 70A, 70B) can be determined within the localizer coordinate system LCLZ, the arrangement of the handle assembly 86 can also be determined relative to other tracked objects. In this way, and as is described in greater detail below, the computing device 30 can facilitate arranging virtual objects associated with the handle assembly 86 within the virtual reference frame VRF which, when rendered in the visual content VC, can assist the user in visualizing various aspects of the handle assembly 86 that might not otherwise be observable within the field of view FOV.

In FIGS. 1 and 9A-9C, the second instrument tracker 70F is shown attached to a guide assembly 88 which, as described in greater detail below, may be employed by the user to help installing fixation elements 24 into engagement with tissue along viable fixation approaches 40. Thus, the localizer 26 can determine the relative pose of the guide assembly 88 based on tracked states of the second instrument tracker 70F. Here too, because the tracked states of the second instrument tracker 70F and other monitored trackers 70 (e.g., the first and second patient trackers 70A, 70B) can be determined within the localizer coordinate system LCLZ, the arrangement of the guide assembly 88 can also be determined relative to other tracked objects. In this way, and as is described in greater detail below, the computing device 30 can facilitate arranging virtual objects associated with the guide assembly 88 within the virtual reference frame VRF which, when rendered in the visual content VC, can assist the user in visualizing various aspects of the guide assembly 88 that might not otherwise be observable within the field of view FOV.

Figure 10A:
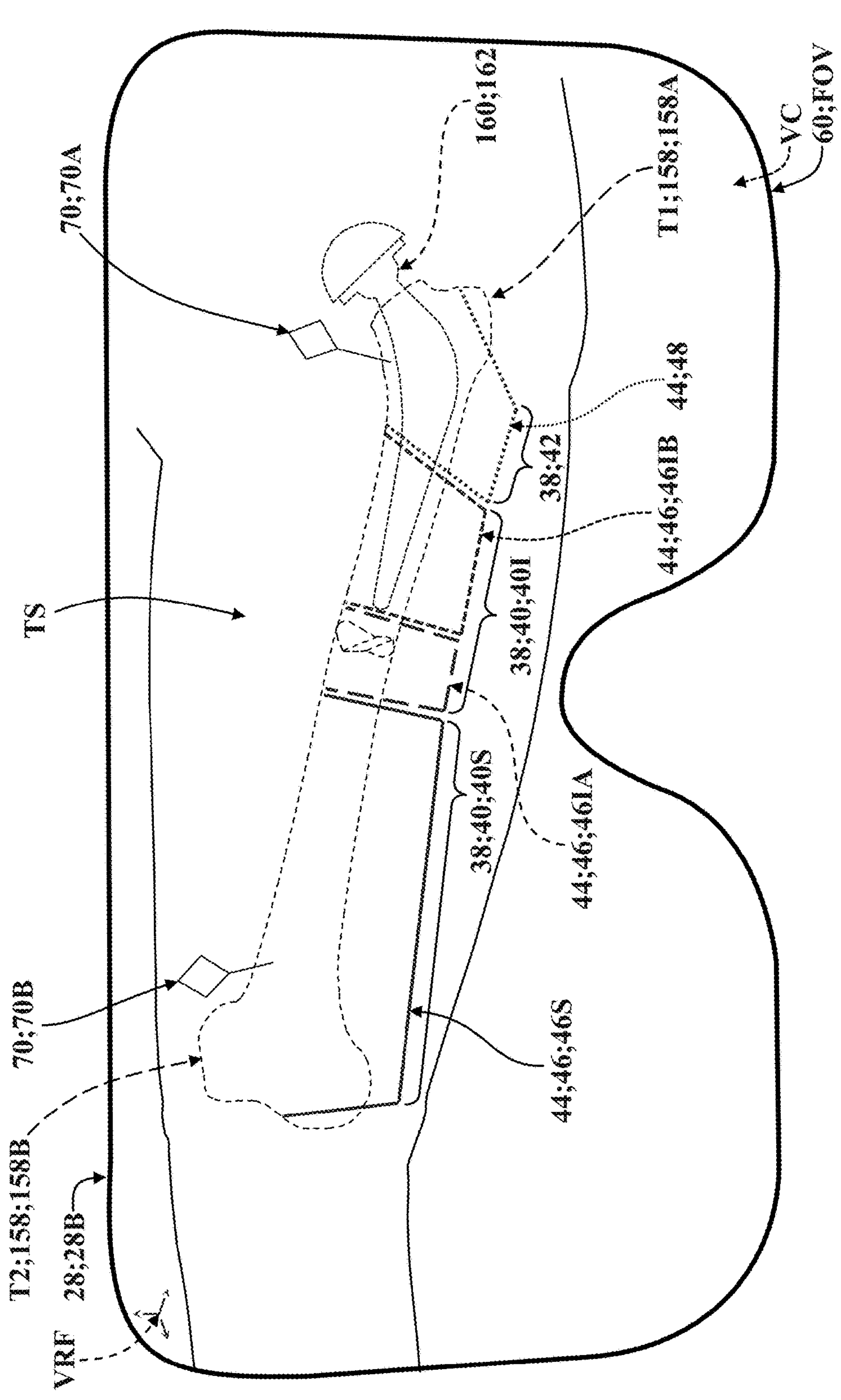
FIG. 10A is a partial perspective view of a patient's anatomy adjacent to a target site defined by portions of the patient's left femur, depicting patient trackers of the navigation system of FIG. 1 attached to different portions of the patient's anatomy, and shown as viewed through a head-mountable display unit displaying visual content comprising virtual patient models, a virtual implant model overlaid onto an unexposed portion of the patient's anatomy to illustrate a reduced diaphyseal periprosthetic fracture at the target site, and a virtual viability model comprising viable portions and non-viable portions, with the viable portions of the virtual viability model displayed as proposed regions associated with viable fixation approaches, and with the non-viable portions of the virtual viability model displayed as proposed regions associated with non-viable fixation approaches.
Figure 10B:
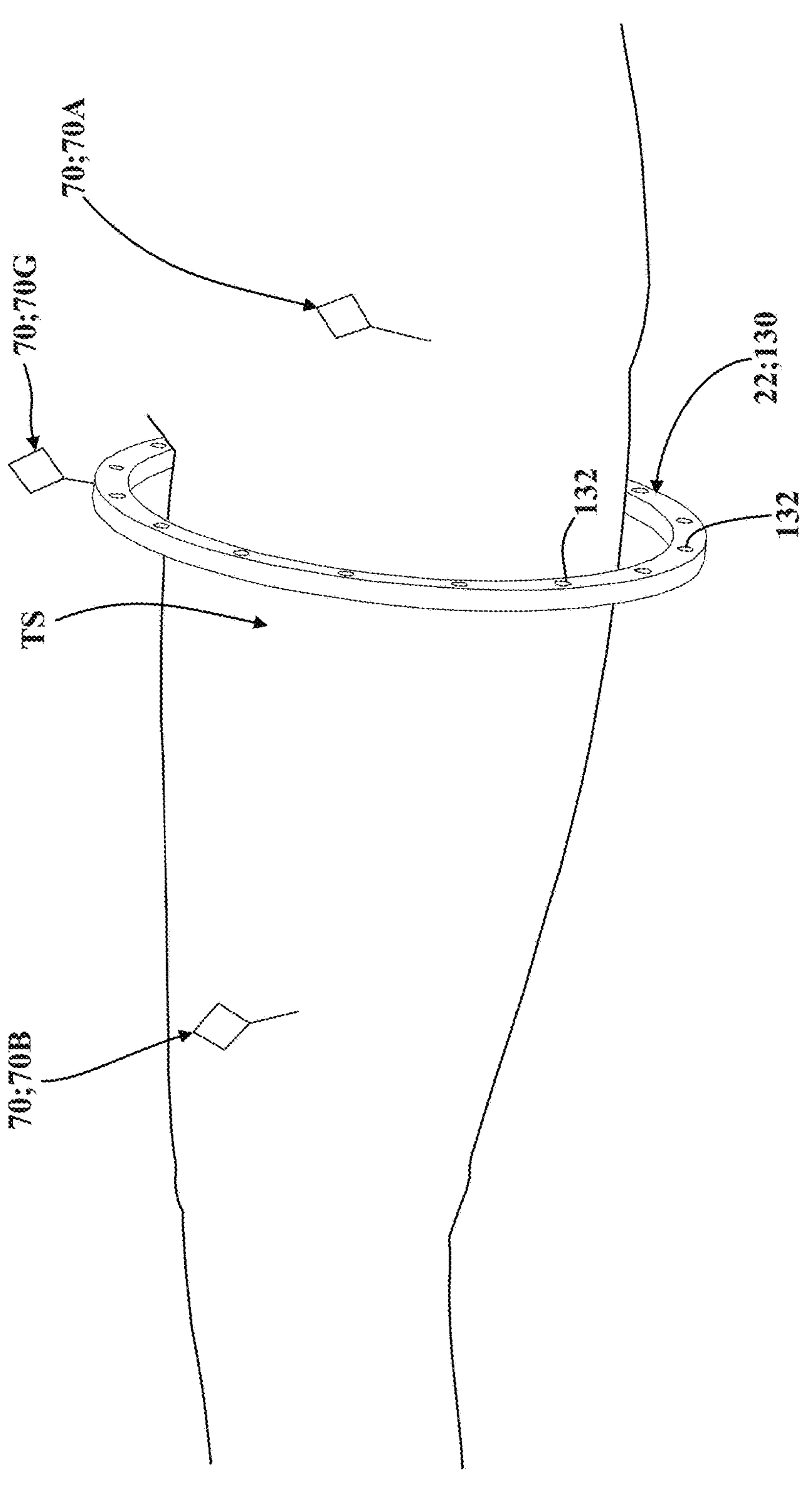
FIG. 10B is another partial perspective view of the patient's anatomy orientated as depicted in FIG. 10A, shown with a first stabilizer positioned along the patient's left thigh adjacent to the target site, and depicting a tracker of the navigation system of FIG. 1 attached to the first stabilizer.
Figure 10C:
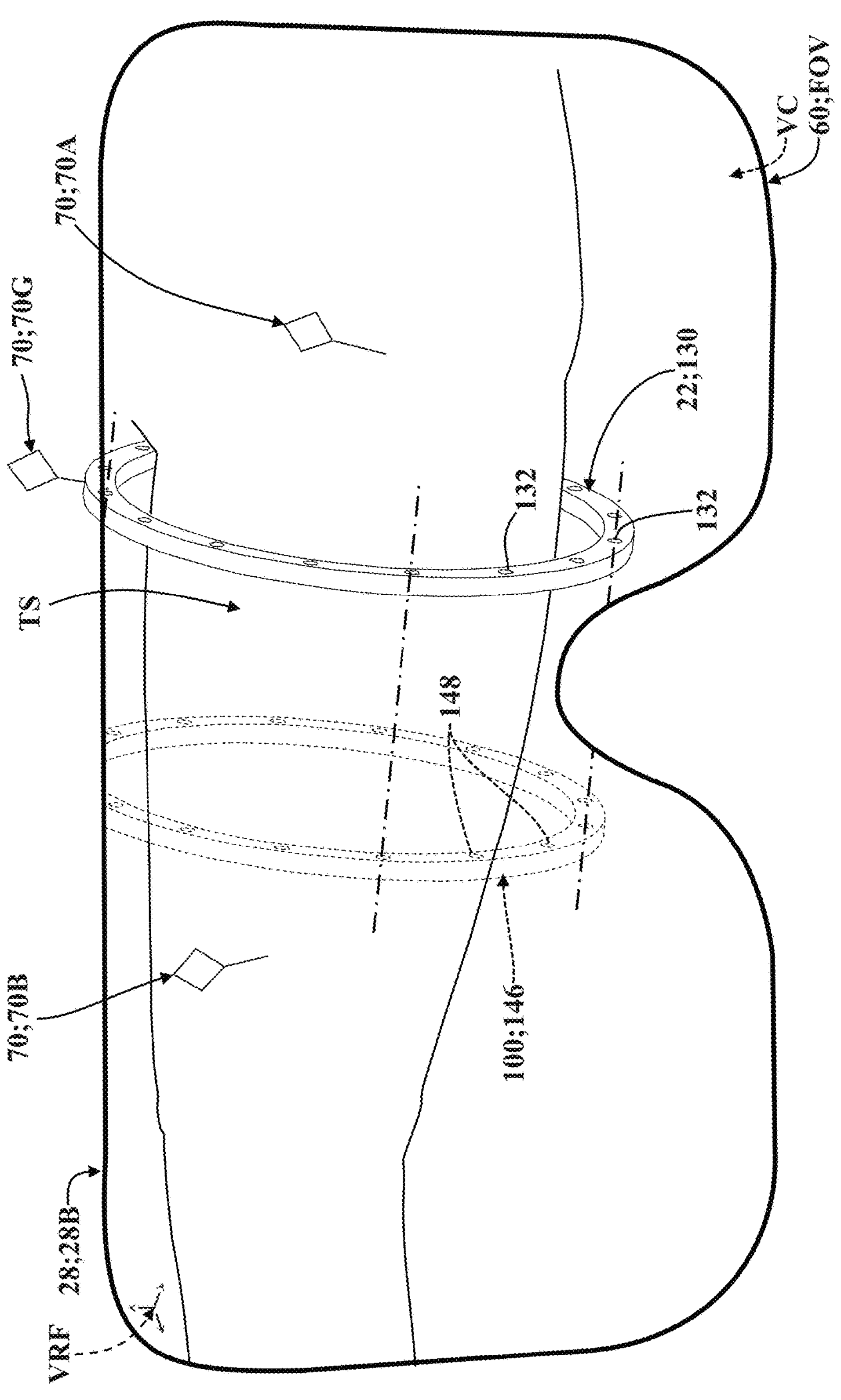
FIG. 10C is another partial perspective view of the patient's anatomy orientated as depicted in FIGS. 10A-10B, shown as viewed through the head-mountable display unit displaying visual content comprising a virtual stabilizer model arranged offset from the first stabilizer positioned along the patient's left thigh to illustrate a configuration for constructing an external stabilizer frame relative to the target site.
Figure 10D:
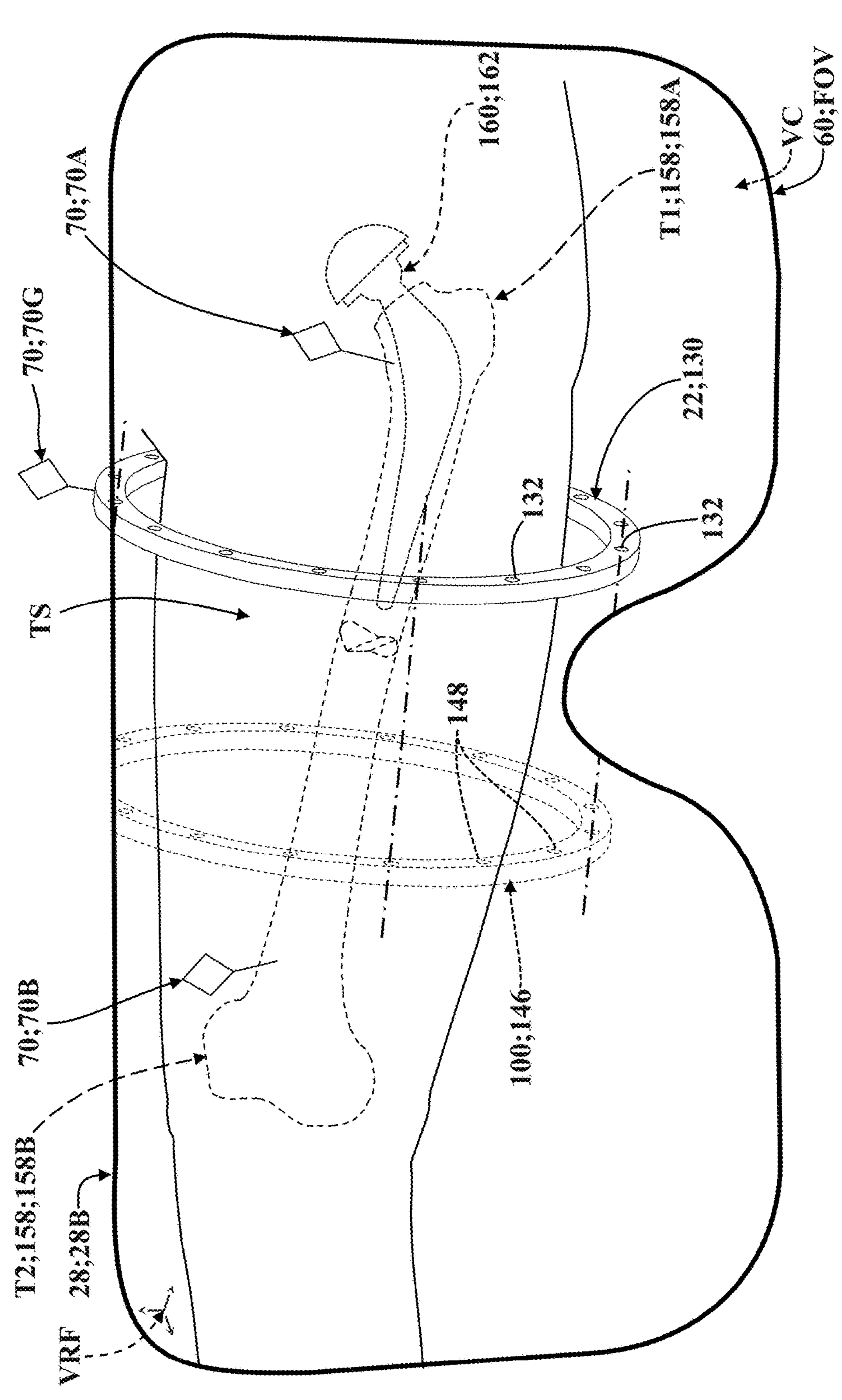
FIG. 10D is another partial perspective view of the patient's anatomy orientated as depicted in FIGS. 10A-10C, shown as viewed through the head-mountable display unit displaying the visual content of FIG. 10C along with portions of the visual content of FIG. 10A to illustrate the arrangement of the first stabilizer and the virtual stabilizer model relative to the virtual patient models and the virtual implant model.
Figure 10E:
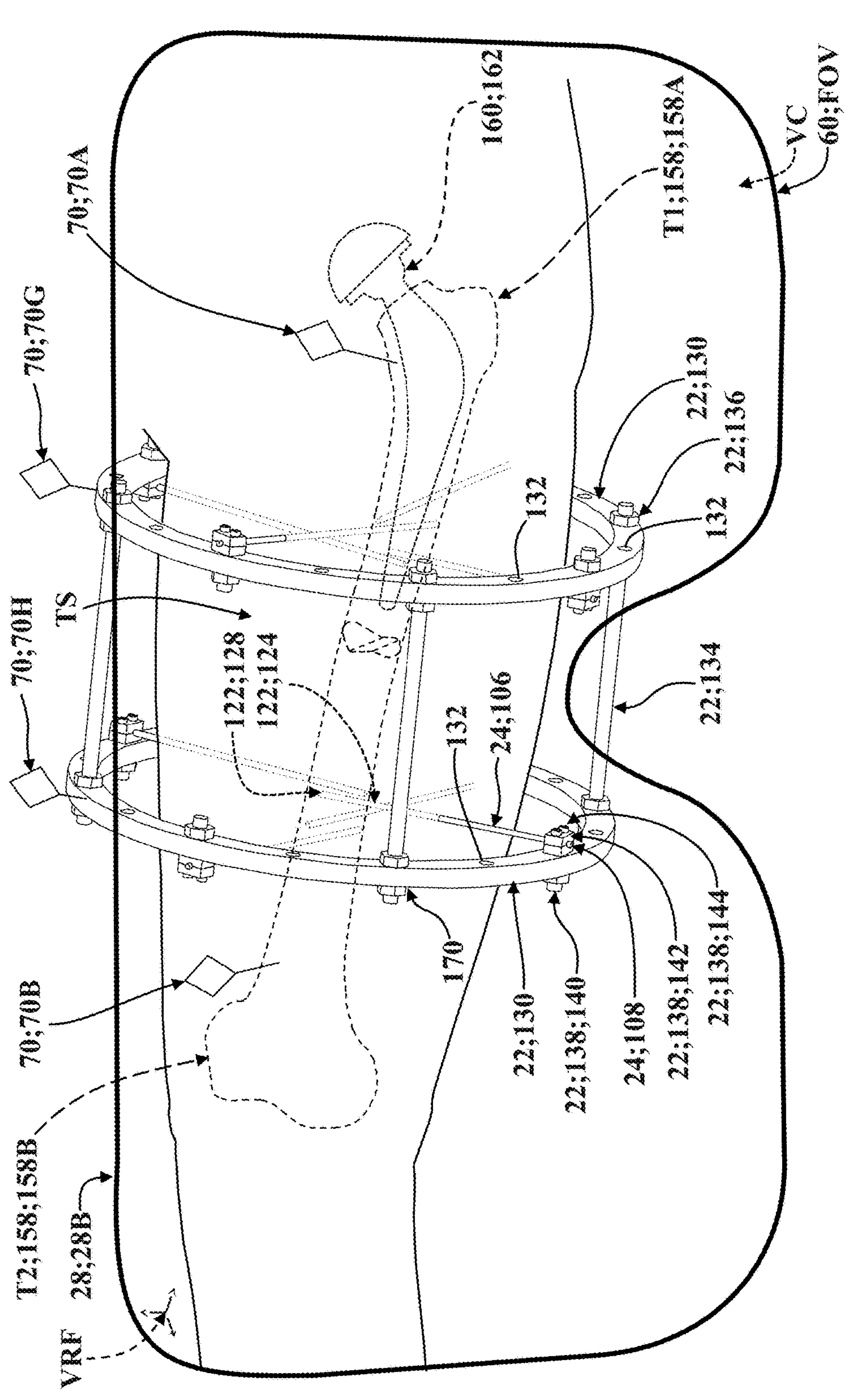
FIG. 10E is another partial perspective view of the patient's anatomy orientated as depicted in FIGS. 10A-10D, depicting a second stabilizer secured to the first stabilizer to define an external stabilizer frame constructed based on the arrangement of the virtual stabilizer model depicted in FIG. 10C with a plurality of fixation elements secured to the external stabilizer frame, shown as viewed through the head-mountable display unit displaying portions of the visual content of FIG. 10D along with a plurality of virtual fixation element models arranged corresponding to the plurality of fixation elements to illustrate engagement of the fixation elements with tissue at the target site.
Figure 10F:
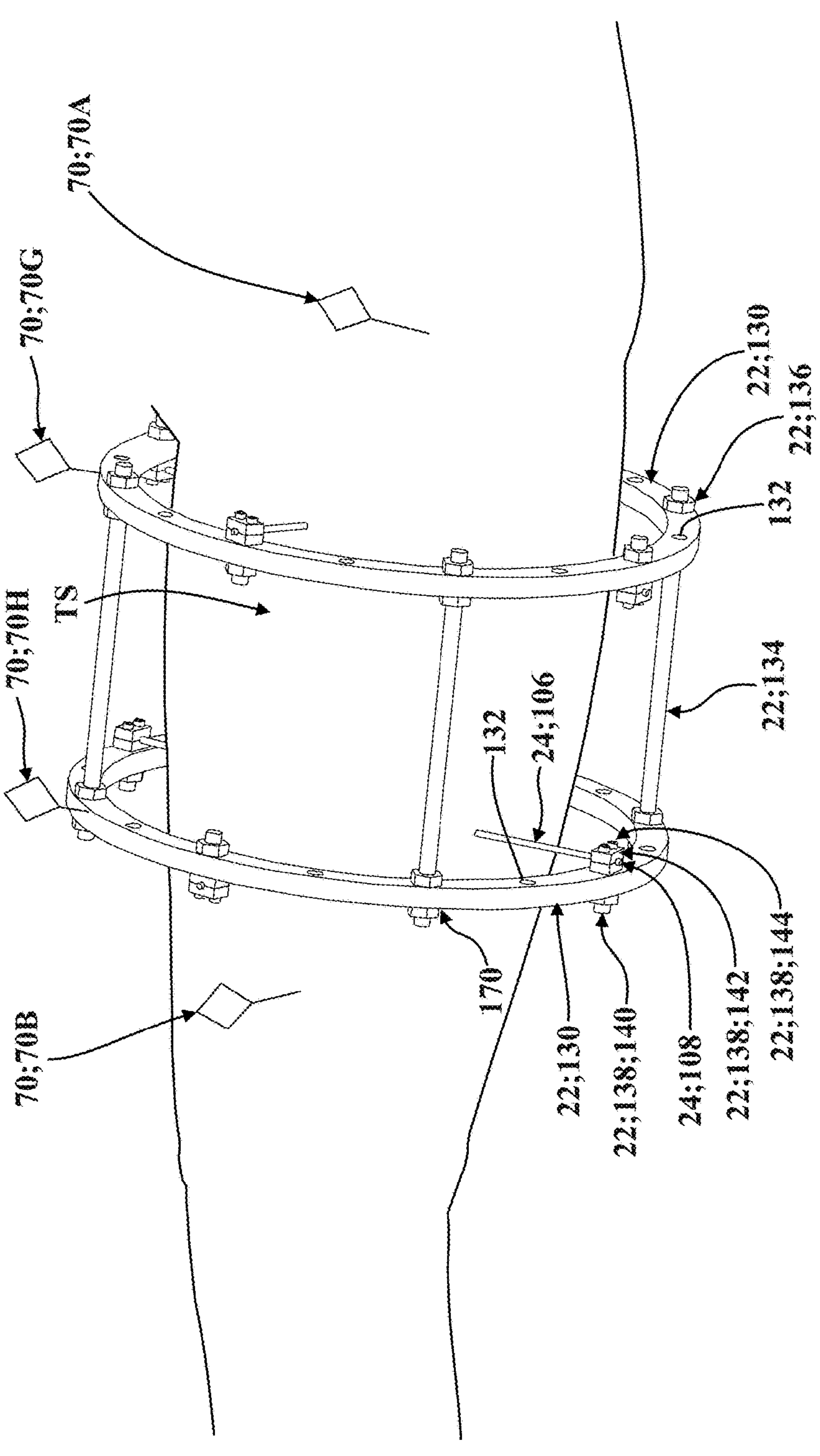
FIG. 10F is another partial perspective view of the patient's anatomy orientated as depicted in FIGS. 10A-10E, shown with the external stabilizer frame and the plurality of fixation elements arranged as depicted in FIG. 10E.

In FIGS. 10E-10F (see also FIGS. 10B-10D), the first and second stabilizer trackers 70G, 70H are shown attached to respective stabilizers 22 which, as described in greater detail below, are configured to be secured relative to each other. Thus, the localizer 26 can determine the relative pose of certain stabilizers 22 based on tracked states of the first and second stabilizer trackers 70G, 70H. Here too, because the tracked states of the first and second stabilizer trackers 70G, 70H and other monitored trackers 70 (e.g., the first and second patient trackers 70A, 70B) can be determined within the localizer coordinate system LCLZ, the arrangement of certain stabilizers 22 can also be determined relative to other tracked objects. In this way, and as is described in greater detail below, the computing device 30 can facilitate arranging virtual objects associated with certain stabilizers 22 within the virtual reference frame VRF which, when rendered in the visual content VC, can assist the user in visualizing various aspects of stabilizers that might not otherwise be observable within the field of view FOV.

In FIG. 1, the imaging system tracker 70I is shown attached to the C-arm imaging system 54 which, as noted above, may be employed to intraoperatively generate patient-specific imaging data ID used by the computing device 30 and, thus, may serve as a portion of the navigation system 68. Furthermore, in certain embodiments, the C-arm imaging system 54 could define the localizer 26, such as by imaging of radio-opaque markers 84 attached to the patient's anatomy instead of (or in addition to) the illustrated first and second patient trackers 70A, 70B, whereby one or more portions of patient-specific imaging data ID, and/or one or more portions of the patient location data PLD, could be generated intraoperatively based on imaging of radio-opaque markers 84 attached to portions of the patient's anatomy.

In the representative embodiment illustrated in FIG. 1, the localizer 26 coupled to the cart assembly 72 could be utilized to determine the relative pose of the C-arm imaging system 54 within the localizer coordinate system LCLZ based on tracked states of the imaging system tracker 70I, and the C-arm imaging system 54 itself could be utilized to determine the relative pose of radio-opaque markers 84 within its own coordinate system (not shown). Here, because the tracked states of the imaging system tracker 70I can be determined within the localizer coordinate system LCLZ, and because the tracked states of the radio-opaque markers 84 can be determined within a coordinate system defined by the C-arm imaging system (not shown), the tracked states of the radio-opaque markers 84 can be transformed into the localizer coordinate system LCLZ such that the arrangement of the radio-opaque markers 84 can be determined relative to objects tracked by the localizer 26. Put differently, the arrangement of objects tracked in one coordinate system can also be determined relative to the arrangement of objects tracked in a different coordinate system where there is a known relation between the coordinate systems (e.g., based on predetermined geometric relationships that are known, are determined by registration techniques, and the like).

In applications where multiple trackers 70 can be monitored within a common coordinate system (e.g., the localizer coordinate system LCLZ), relative movement occurring between the tracked objects results in corresponding relative movement occurring between their poses in the common coordinate system (e.g., represented by individual tracker coordinate systems). It will be appreciated that data associated with the pose of one or more of the trackers 70 within the localizer coordinate system LCLZ (e.g., location data) may be translated (e.g., with the navigation controller 74, with the computing device 30, and the like) into an arbitrary coordinate system (see FIG. 1, not shown in detail) defined by the virtual reference frame VRF of the visualization program 36, and/or vice-versa, using any suitable transformation technique. Thus, in some embodiments, each tracked object in the localizer coordinate system LCLZ may comprise X,Y,Z coordinates within the arbitrary coordinate system ACS, which may be stored in a database, table, list, and the like (e.g., on the memory device 34). The arbitrary coordinate system ACS could be defined in a number of different ways, based such as on the localizer coordinate system LCLZ or another coordinate system common to two or more tracked objects. Examples of the translation or transformation of data between coordinate systems is disclosed in one or more of: U.S. Pat. No. 8,675,939, entitled "Registration of Anatomical Data Sets;" and U.S. Patent Application Publication No. 2018/0333207, entitled "Surgical Systems and Methods for Facilitating Ad-hoc Intraoperative Planning of Surgical Procedures," the disclosures of each of which are hereby incorporated by reference. Other configurations are contemplated, including without limitation those disclosed in other publications referenced herein.

Referring now to FIGS. 1 and 3A-3C, various portions of a stabilization kit 90 are shown. The term "stabilization kit 90" is used herein to refer to one or more stabilizers 22 and/or one or more fixation elements 24 that cooperate to facilitate tissue stabilization at the target site TS. While a number of different styles, types, and/or configurations of stabilizers 22 and fixation elements 24 are contemplated by the present disclosure and are described in greater detail below, those having ordinary skill in the art will appreciated that tissue stabilization can generally be performed using stabilization kits 90 that are configured for use with internal fixation FI and/or external fixation FE methodologies.

For the purposes of clarity and consistency, the term "internal fixation FI" is used herein to refer to tissue stabilization facilitated by the use of stabilizers 22 that are configured to be "implanted" inside the patient's body at the target site TS (e.g., plates, brackets, struts, rods, and the like), such as is described below in connection with FIGS. 5A-9D. Conversely, the term "external fixation FE" is used herein to refer to tissue stabilization facilitated by the use of stabilizers 22 that are configured to remain outside the patient's body adjacent to the target site TS (e.g., frames, jigs, fixtures, linkages, fasteners, spacers, and the like), such as is described below in connection with FIGS. 10A-10F.

For internal fixation FI as well as for external fixation FE, the fixation elements 24 are configured to engage and secure to tissue, and are at least partially "implanted" inside the patient's body (e.g., anchors, screws, nails, pins, wires, cables, and the like). In the present disclosure, fixation elements 24 used in connection with internal fixation FI are generally configured to be "completely implanted" inside the patient's body, whereas fixation elements 24 used in connection with external fixation FE are generally configured to be "partially implanted" inside the patient's body and also extend outside of the patient's body. However, it will be appreciated that the aforementioned characterizations are provided for non-limiting, exemplary, and illustrative purposes. Furthermore, the surgical system 20 of the present disclosure is not limited to stabilization kits 90, stabilizers 22, and/or fixation elements 24 of any specific type and/or configuration, and may be used in connection with surgical procedures that involve tissue stabilization based on internal fixation FI methodologies, external fixation FE methodologies, and/or combinations of both.

Figure 3A:
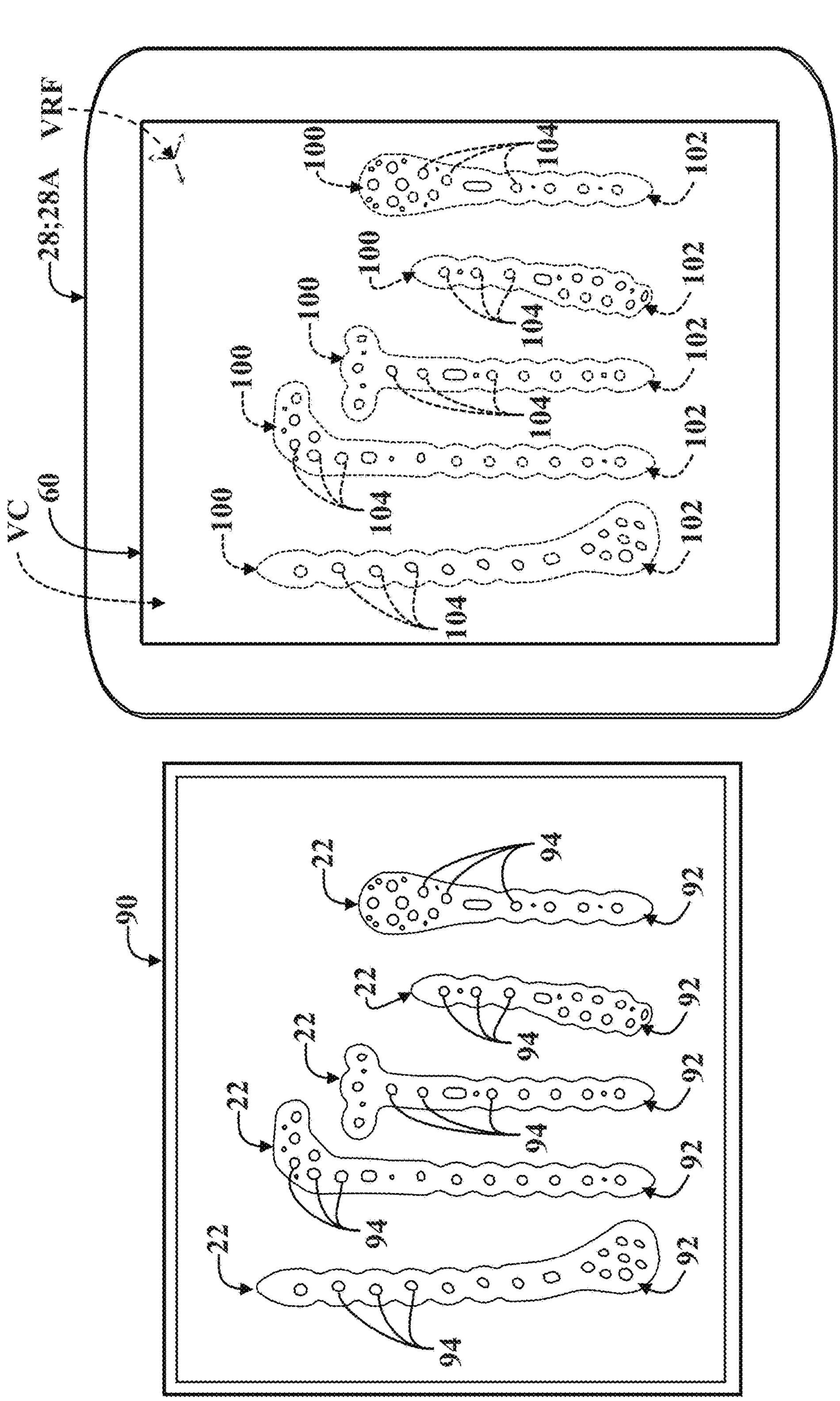
FIG. 3A is a top-side plan view of a tablet display unit and a portion of the stabilization kit of FIG. 1, the illustrated portion of the stabilization kit shown comprising stabilizers realized as implants for internal fixation, and the tablet display unit shown displaying virtual stabilizer models corresponding to the stabilizers.

In FIG. 3A, a portion of the stabilization kit 90 is shown which includes various exemplary types of stabilizers 22 realized as "implantable plates" that are generally configured to facilitate tissue stabilization via internal fixation FI. Each of the stabilizers 22 illustrated in FIG. 3A comprises a stabilizer body 92 that is contoured or otherwise provided with a profile that helps optimize contact with tissue of specific bones. However, certain types of stabilizers 22 may comprise stabilizer bodies 92 with a relatively generic profile that can be used with multiple, different bones. Furthermore, certain types of stabilizers 22 may be configured at least partially based on patient-specific aspects (e.g., based on measurements between anatomical landmarks, and/or the patient's age, gender, height, weight, medical history, pathology, and the like). It will be appreciated that the stabilizers 22 could be configured in a number of different ways, including similar to as is disclosed in one or more of: U.S. Pat. No. 8,864,802, entitled "Implant for Bone Fixation;" U.S. Pat. No. 10,123,830, entitled "Hybrid Bone Plate;" U.S. Patent Application Publication No. 2017/0164987, entitled "Bone Plate with Polyaxial Locking Mechanism;" U.S. Patent Application Publication No. 2017/0181780, entitled "Bone Plate with Elongated Guiding Channels;" and U.S. Patent Application Publication No. 2017/0215931, entitled "Bone Plate with Alternating Chamfers," the disclosures of each of which are hereby incorporated by reference. Other configurations are contemplated, including without limitation those disclosed in other publications referenced herein.

Irrespective of the specific configurations of their profiles, each of the stabilizers 22 depicted in FIG. 3A defines a plurality of apertures 94 formed extending through its stabilizer body 92 that are shaped to receive a respective fixation element 24 therethrough. It will be appreciated that the apertures 94 are generally arranged to provide the surgeon with multiple fixation approaches 38 for a single stabilizer 22 (e.g., one or more trajectories associated with each aperture 94). While not illustrated in detail herein, certain apertures 94 may be configured so as to receive only certain types of fixation elements 24 based, for example, on size, shape, and/or structural features (e.g., internal threads such as those described in greater detail below in connection with FIG. 3B). On the other hand, certain apertures 94 may be configured to receive more than one type of fixation element 24. Similarly, certain apertures 94 may be slotted, threaded, angled, tapered, or otherwise configured to afford the user with different options for a given surgical procedure. Other configurations are contemplated. Furthermore, certain apertures 94 may be configured to facilitate releasable attachment of the stabilizer 22 to the handle assembly 86 as noted above.

As shown in FIG. 1 (see also FIGS. 8A-8E), the handle assembly 86 generally comprises a handle grip 96 configured for engagement by the user, and a coupler 98 to facilitate releasable attachment of the stabilizer 22. Here, it will be appreciated that the coupler 98 could be configured in a number of different ways sufficient to facilitate releasable attachment to one or more types of stabilizers 22. By way of non-limiting example, the coupler 98 may be configured to indirectly attach to the stabilizer 22 via an aiming block (not shown) provided with alignment features that interlock with corresponding alignment features formed in the stabilizer 22 and/or with one or more retention apertures aligned to apertures 94 of the stabilizer 22. To this end, the handle assembly 86 could be configured similar to as is disclosed in one or more of: U.S. Pat. No. 7,648,508, entitled "Bone Plating Implants, Instruments and Methods;" U.S. Pat. No. 8,709,014, entitled "Device Kit, and Method for Handling a Medical Implant;" and U.S. Patent Application Publication No. 2018/0325566, entitled "Stereotactic Computer Assisted Surgery Method and System," the disclosures of each of which are hereby incorporated by reference. Other configurations are contemplated, including without limitation those disclosed in other publications referenced herein.

Referring again to FIG. 3A, the tablet display unit 28A (e.g., a tablet computer, mobile phone, or another type of portable electronic device) is shown displaying visual content VC including virtual stabilizer models 100. More specifically, the visual content VC displayed by the tablet display unit 28A in FIG. 3A comprises a plurality of virtual stabilizer models 100, each of which corresponds to a respective one of the plurality of stabilizers 22 also depicted in FIG. 3A. Each of the virtual stabilizer models 100 comprises a respective virtual stabilizer body 102 which defines a plurality of virtual apertures 104 arranged relative to the corresponding plurality of apertures 94 formed in the stabilizer body 92 of its respective stabilizer 22.

As is described in greater detail below in connection with FIGS. 6A-9D, in some embodiments, the surgical system 20 may be configured to enable selection of one or more virtual stabilizer models 100 for arrangement within the virtual reference frame VRF via the visualization program 36. Here, FIG. 3A illustrates that the size, shape, profile, and aperture 94 arrangement of each stabilizer 22 in the stabilization kit 90 is represented by a respective virtual stabilizer model 100 that can be arranged within the virtual reference frame VRF. Thus, the visualization program 36 may also be configured to identify one or more of the plurality of different fixation approaches 38 based at least partially on the arrangement of the plurality of virtual apertures 104 of a selected virtual stabilizer model 100 within the virtual reference frame VRF, and may construct, generate, or otherwise arrange the virtual viability model 44 within the virtual reference frame based at least partially on the arrangement of the plurality of virtual apertures 104 of the selected virtual stabilizer model 100. Additional aspects of the tablet display unit 28A and the virtual stabilizer models 100 will be described in greater detail below.

Figure 3B:
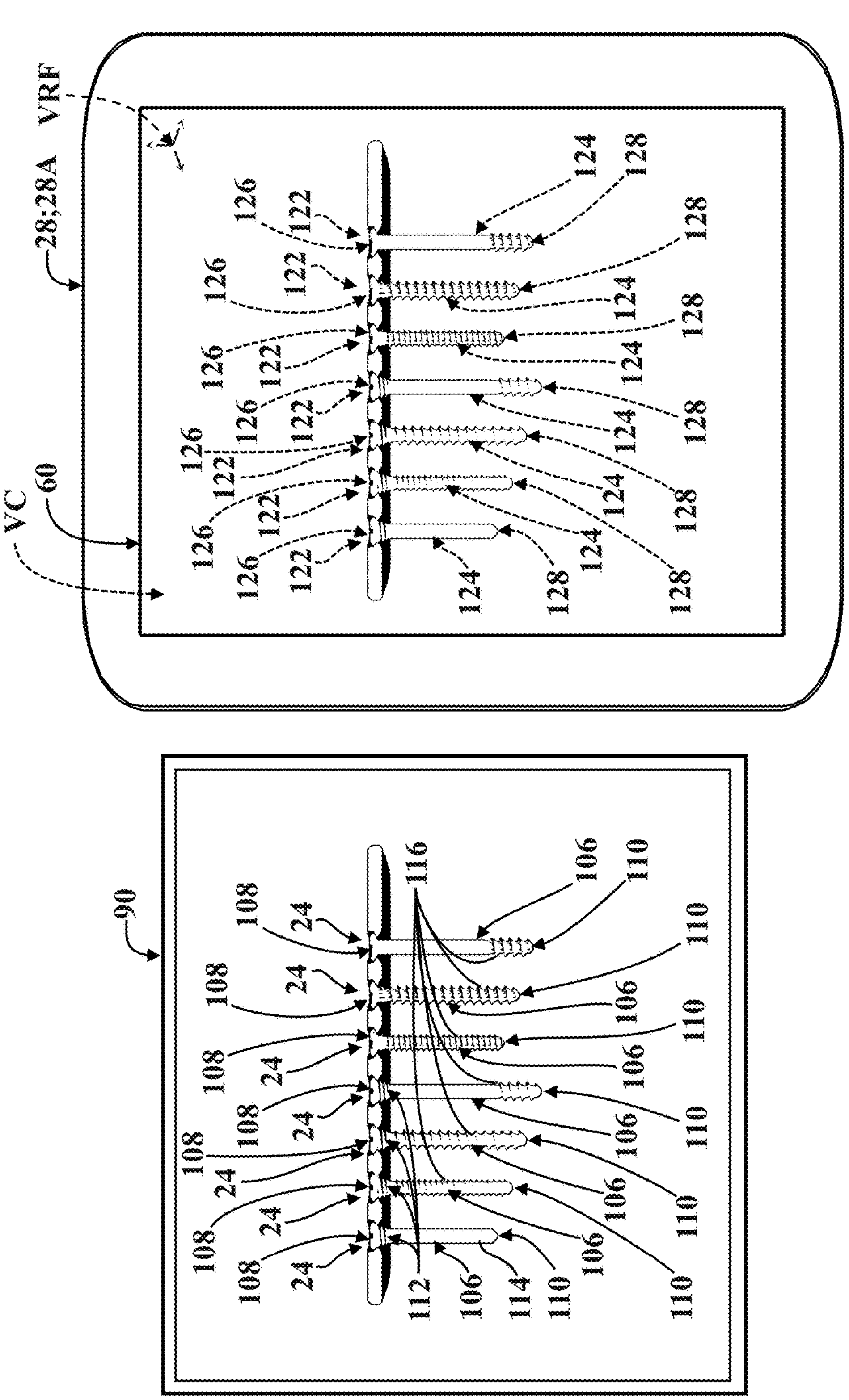
FIG. 3B is a top-side plan view of a tablet display unit and another portion of the stabilization kit of FIG. 1, the illustrated portion of the stabilization kit shown comprising fixation elements for engaging implants, and the tablet display unit shown displaying virtual fixation element models corresponding to the fixation elements.

In FIG. 3B, another portion of the stabilization kit 90 is shown which includes various exemplary types of fixation elements 24 realized as "implantable screws" that are generally configured to facilitate tissue stabilization via internal fixation FI. The representative fixation elements 24 illustrated in FIG. 3B each comprise a fixation element body 106 which extends between an interface end 108 and an engagement end 110. The interface end 108 of the fixation element 24 is generally configured for engagement by a surgical instrument, tool, driver, and the like (e.g., to facilitate concurrent rotation), and also configured to be received in or otherwise adjacent to one of the plurality of apertures 94 defined by the stabilizer 22. The engagement end 110 of the fixation element 24 is generally configured for engagement with tissue at the target site TS.

Some of the representative fixation elements 24 illustrated in FIG. 3B include locking features 112 (e.g., external threads) arranged along the fixation element body 106 adjacent to the interface end 108. Here, the locking features 112 are configured to engage with or otherwise lock to apertures 94 formed in certain types of stabilizers 22 (e.g., apertures 94 with corresponding internal threads). One of the representative fixation elements 24 illustrated in FIG. 3B employs an engagement end 110 realized with a smooth peg 114, while the other representative fixation elements 24 illustrated in FIG. 3B employ engagement ends 110 realized with threaded teeth 116 of various arrangements, profiles, and the like. It will be appreciated that different types of fixation elements 24 may be utilized with the same stabilizer 22 (e.g., with fixation element bodies 106 of different lengths, with threaded teeth 116 configured to engage different types of tissue or different portions of the same tissue, and the like). Furthermore, it will be appreciated that the fixation elements 24 could be configured in a number of different ways, including similar to as is disclosed in one or more of: U.S. Pat. No. 7,686,837, entitled "Polyaxial Locking Implantable Orthopedic Fixation Device;" U.S. Pat. No. 7,799,062, entitled "Self-Guiding Threaded Fastener;" U.S. Pat. No. 9,107,678, entitled "Locking Screw with Synchronized Thread;" U.S. Pat. No. 9,339,315, entitled "Bone Fixation System with Curved Profile Threads;" U.S. Patent Application Publication No. 2016/0143663, entitled "Strut Plate and Cabling System;" and U.S. Patent Application Publication No. 2018/0110545, entitled "Biased Angle Screws," the disclosures of each of which are hereby incorporated by reference. Other configurations are contemplated, including without limitation those disclosed in other publications referenced herein.

Those having ordinary skill in the art will appreciate that certain types of fixation elements 24 may be configured for direct engagement with tissue (e.g., "k-wires" driven by a wire driver, "self-tapping" screws driven by a rotary instrument, and the like), while other types of fixation elements 24 may be configured for engagement with tissue by being driven into a pilot hole (not shown in detail) drilled into or otherwise formed in tissue along a viable fixation approach 40 (e.g., via a drill bit driven by a rotary instrument). To this end, and as is shown in FIG. 1 (see also FIGS. 9A-9C), a guide assembly 88 may be utilized to help facilitate drilling or forming pilot holes and/or to help facilitate driving fixation elements 24 into pilot holes or directly into engagement with tissue (e.g., a "self-tapping" screw supported by the guide assembly 88 along a viable fixation approach 40). To this end, the guide assembly 88 generally comprises a guide grip 118 configured for engagement by the user, and a bore element 120 defining a penetration trajectory PT to be aligned with one or more viable fixation approaches 40, as described in greater detail below in connection with FIGS. 9A-9C. It will be appreciated that the guide assembly 88 could be configured in a number of different ways, including similar to as is disclosed in one or more of: U.S. Pat. No. 6,036,696, entitled "Guide-pin Placement Device and Method of Use;" U.S. Pat. No. 7,077,847, entitled "Targeting Device for Locking Nails;" U.S. Pat. No. 7,311,710, entitled "Targeting Device for a Locking Nail;" U.S. Pat. No. 7,147,643, entitled "Implantation System and Aiming Device for the Same;" U.S. Pat. No. 8,118,810, entitled "Targeting Device for Bone Implant;" U.S. Pat. No. 9,050,151, entitled "Bone Plate and Aiming Block;" and U.S. Pat. No. 9,107,709, entitled "Targeting Adjustment," the disclosures of each of which are hereby incorporated by reference. Other configurations are contemplated, including without limitation those disclosed in other publications referenced herein.

Referring again to FIG. 3B, the tablet display unit 28A is shown displaying visual content VC including virtual fixation element models 122. More specifically, the visual content VC displayed by the tablet display unit 28A in FIG. 3B comprises a plurality of virtual fixation element models 122, each of which corresponds to a respective one of the plurality of fixation elements 24 also depicted in FIG. 3B. Each of the illustrated virtual fixation element models 122 comprises a virtual fixation element body 124 which extends between a virtual interface end 126 and a virtual engagement end 128 arranged relative to the corresponding interface end 108 and engagement end 110 of the fixation element body 106 of its respective fixation element 24.

In some embodiments, the surgical system 20 may be configured to enable selection of one or more virtual fixation element models 122 for arrangement within the virtual reference frame VRF via the visualization program 36. Here, FIG. 3B illustrates that the size, shape, and configuration of each fixation element 24 in the stabilization kit 90 is represented by a respective virtual fixation element model 122 that can be arranged within the virtual reference frame VRF. Thus, the visualization program 36 may also be configured to identify one or more of the plurality of different fixation approaches 38 based at least partially on the arrangement of the plurality of virtual apertures 104 of a selected virtual fixation element model 122 within the virtual reference frame VRF, and may generate, construct, or otherwise the virtual viability model 44 based at least partially on the configurations of and/or the arrangement between the virtual interface end 126 and the virtual engagement end 128 of the virtual fixation element body 124.

Additional aspects of the virtual fixation element models 122 will be described in greater detail below.

Figure 3C:
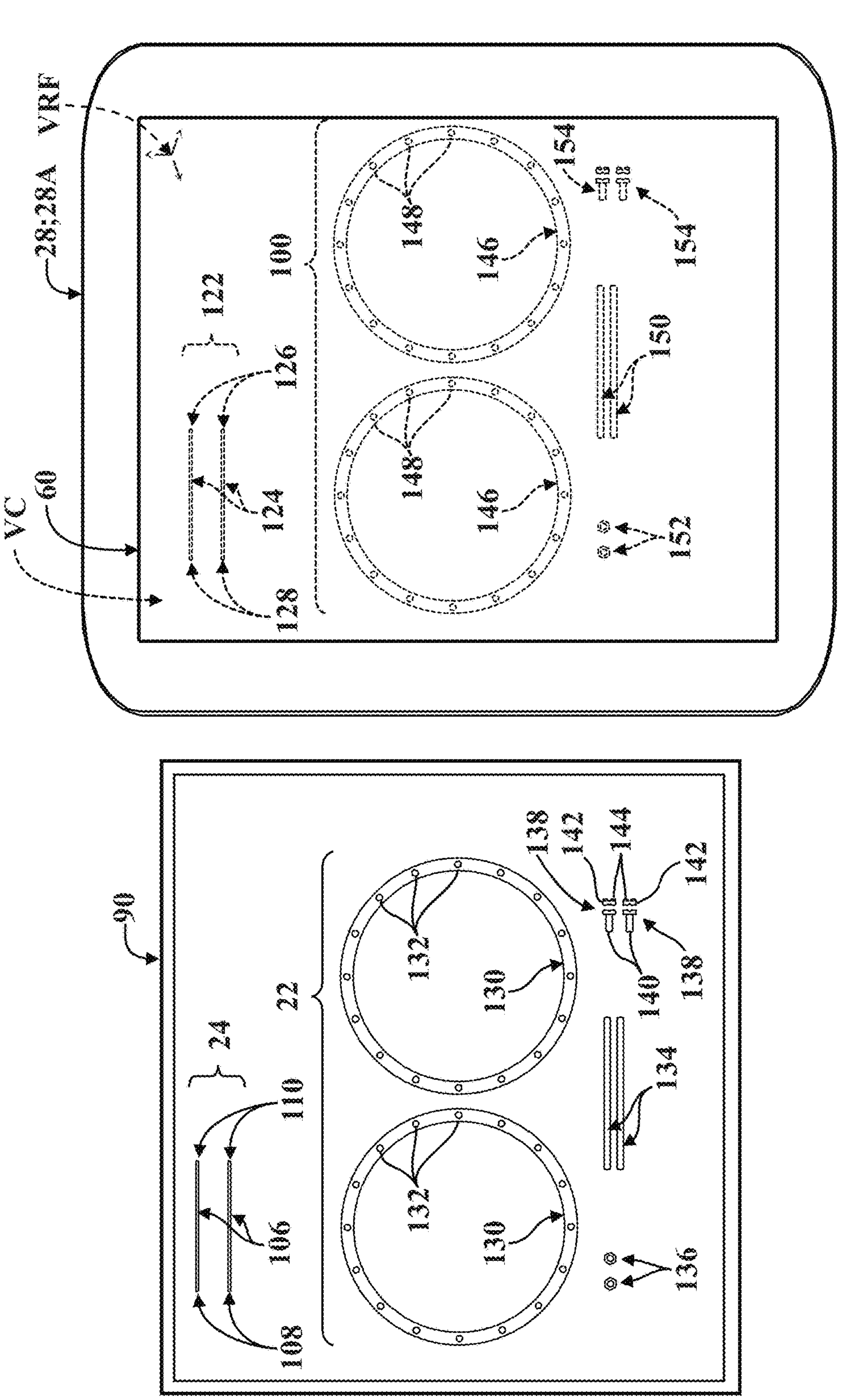
FIG. 3C is a top-side plan view of a tablet display unit and a yet another portion of the stabilization kit of FIG. 1, the illustrated portion of the stabilization kit shown comprising stabilizers realized as frame components for external fixation and fixation elements for engaging the frame components, and the tablet display unit shown displaying virtual stabilizer models corresponding to the stabilizers and virtual fixation element models corresponding to the fixation elements.

In FIG. 3C, yet another portion of the stabilization kit 90 is shown which includes fixation elements 24 realized as "pins" and stabilizers 22 realized as "frame components" (e.g., used to construct external fixation frames according to the Ilizarov technique). The fixation elements 24 shown in FIG. 3C (and also in FIGS. 10E-10F) are depicted generically, and comprise cylindrical fixation element bodies 106. However, it will be appreciated that other configurations are contemplated. The stabilizers 22 shown in FIG. 3C (and also in portions of FIGS. 10B-10F) are also depicted generically, and comprise ring members 130 defining mounts 132, connecting rods 134, fasteners 136, and locks 138. The ring members 130 are fixed relative to each other via connecting rods 134 inserted into the mounts 132 and secured with fasteners 136 (e.g., via threaded engagement; not shown). The locks 138 each comprise a positioning member 140 and a locking member 142 which releasably attach to each other via locking fasteners 144 to secure to the interface end 108 of the fixation element 24 (see FIGS. 10E-10F). The positioning members 140, in turn, are inserted through the mounts 132 and are secured thereto with fasteners 136.

It will be appreciated that a number of different arrangements of the ring members 130, the connecting rods 134, the fasteners 136, and the locks 138 of the exemplary portion of the stabilization kit 90 illustrated in FIG. 3C can be utilized to construct external fixation frames which secure fixation elements 24 in various orientations, positions, and the like relative to the target site TS. Those having ordinary skill in the art will appreciate that external fixation frames can be constructed in numerous ways according to various external fixation FE methodologies, such as from other and/or different components which interlock or are otherwise configured for modular construction in ways other than those specifically illustrated and described herein, including similar to as is disclosed in one or more of: U.S. Pat. No. 4,365,624, entitled "External Bone-anchoring Element;" U.S. Pat. No. 7,527,626, entitled "External Fixation Element;" U.S. Pat. No. 8,333,766, entitled "External Fixation System;" U.S. Pat. No. 8,834,467, entitled "External Fixator System;" U.S. Pat. No. 8,945,128, entitled "External Fixator System;" U.S. Pat. No. 8,951,252, entitled "External Fixation System;" U.S. Pat. No. 9,011,438, entitled "Radiolucent Orthopedic Fixation Plate;" U.S. Patent Application Publication No. 2018/0168691, entitled "Methods and Systems for Adjusting an External Fixation Frame;" U.S. Patent Application Publication No. 2018/0214181, entitled "Strut Attachments for External Fixation Frame;" U.S. Patent Application Publication No. 2018/0221056, entitled "Ring Hole Planning for External Fixation Frames;" and U.S. Patent Application Publication No. 2018/0228514, entitled "Gear Mechanisms for Fixation Frame Struts," the disclosures of each of which are hereby incorporated by reference. Other configurations are contemplated, including without limitation those disclosed in other publications referenced herein.

With continued reference to FIG. 3C, the tablet display unit 28A is shown displaying visual content VC including virtual stabilizer models 100 and virtual fixation element models 122. More specifically, the visual content VC displayed by the tablet display unit 28A in FIG. 3C comprises a plurality of virtual stabilizer models 100, including virtual ring member models 146 with virtual mounts 148, virtual connecting rod models 150, virtual fastener models 152, and virtual lock models 154 which respectively correspond to the ring members 130 with the mounts 132, the connecting rods 134, the fasteners 136, and the locks 138 of the stabilizers 22 also depicted in FIG. 3C. Here too, the visual content VC displayed by the tablet display unit 28A in FIG. 3C comprises a plurality of virtual fixation element models 122, each of which corresponds to a respective one of the plurality of fixation elements 24 also depicted in FIG. 3C.

In some embodiments, the surgical system 20 may be configured to enable selection of one or more virtual fixation element models 122 and/or virtual stabilizer models 100 for arrangement within the virtual reference frame VRF via the visualization program 36 to, among other things, optimize or assist in the visualization of frame construction with external fixation FE with tissue stabilization methodologies. Here FIG. 3C illustrates that the size, shape, and configuration of each fixation element 24 in the stabilization kit 90 is represented by a respective virtual fixation element model 122 that can be arranged within the virtual reference frame VRF. Similarly, FIG. 3C illustrates that the size, shape, and configuration of each stabilizer 22 (and subcomponents thereof as depicted in FIG. 3C) in the stabilization kit 90 is represented by a respective virtual stabilizer model 100 that can likewise be arranged within the virtual reference frame VRF. Thus, the visualization program 36 may also be configured to identify one or more of the plurality of different fixation approaches 38 based at least partially on the arrangement of one or more selected virtual fixation element models 122 and/or one or more selected virtual stabilizer models 100 within the virtual reference frame VRF, and may generate, construct, or otherwise arrange the virtual viability model 44 based at least partially on the configurations thereof and/or the arrangements therebetween. Other configurations are contemplated.

As noted above, the computing device 30 receives the patient location data PLD generated by the localizer 26 that is associated with a location of at least a portion of the patient's anatomy. In order to overlay visual content VC rendered within the virtual reference frame VRF (e.g., the virtual viability model 44) such that it can be displayed overlaid onto the patient's anatomy within the field of view to assist the user in visualizing fixation approaches 38, the computing device 30 may also receive display location data DLD generated by the localizer 26 that is associated with a location of at least a portion of whichever display unit 28 is being utilized to display the visual content VC (e.g., based on tracked states of the first and/or second display unit trackers 70C, 70D).

Because the patient location data PLD and the display location data DLD are based in or can otherwise be transformed into a common coordinate system (e.g., the localizer coordinate system LCLZ), the computing device 30 can dynamically adjust arrangement of the virtual viability model 44 within the virtual reference frame VRF such that the visual content VC is displayed overlaid onto the patient's anatomy within the field of view FOV in a correspondingly-dynamic fashion in order to compensate for relative movement occurring between the tracked portion of the patient's anatomy and the display unit 28. As noted above, the navigation system 68 can track states of the first and/or second patient trackers 70A, 70B to generate the patient location data PLD relative to the localizer coordinate system LCLZ, and can similarly track states of the first and/or second display unit trackers 70C, 70D to generate the display location data DLD relative to the localizer coordinate system LCLZ. However, it will be appreciated that the display location data DLD can be related to other tracked objects in a common coordinate system in different ways, such as where the camera 66 of the display unit 28 serves as the localizer 26 and location data generated by the camera 66 is based on a coordinate system that moves with the display unit 28. Other configurations are contemplated.

In some embodiments, the computing device 30 may also receive handle location data HLD generated by the localizer 26 that is associated with a location of at least a portion of the handle assembly 86 (e.g., based on tracked states of the first instrument tracker 70E). Here, because the patient location data PLD, the display location data DLD, and the handle location data HLD are each based in or can otherwise be transformed into a common coordinate system (e.g., the localizer coordinate system LCLZ), and because the configurations of the various types of stabilizers 22 in the stabilization kit 90 that can releasably attach to the handle assembly 86 are known based, among other things, on their geometry and/or based on the geometry of their corresponding virtual stabilizer models 100, the computing device 30 can dynamically adjust the arrangement of virtual stabilizer models 100 within the virtual reference frame VRF such that the visual content VC is displayed in a correspondingly-dynamic fashion in order to compensate for relative movement occurring between the tracked portion of the patient's anatomy and the handle assembly 86 secured to the stabilizer 22. Here too, the navigation system 68 can track states of the first instrument tracker 70E to generate the handle location data HLD relative to the localizer coordinate system LCLZ which, in turn, can be used to arrange the virtual stabilizer models 100 within the virtual reference frame VRF. Alternatively, the navigation system 68 can track states of the first and/or second stabilizer trackers 70G, 70H to generate location data relative to the coordinate system LCLZ which can be used to arrange the virtual stabilizer models 100 within the virtual reference frame VRF. Moreover, it will be appreciated that handle location data HLD can be related to other tracked objects in a common coordinate system in different ways, such as where the tablet display unit 28A is fixed to the handle assembly 86 (not shown) and its camera 66 serves as the localizer 26 such that location data generated by the camera 66 is based on a coordinate system that moves with the tablet display unit 28A and, thus with, the handle assembly 86 fixed thereto. Other configurations are contemplated.

In some embodiments, the computing device 30 may also receive guide location data GLD generated by the localizer 26 that is associated with a location of at least a portion of the guide assembly 88 (e.g., based on tracked states of the second instrument tracker 70F). Here, because the patient location data PLD, the display location data DLD, the handle location data HLD, and the guide location data GLD are each based in or can otherwise be transformed into a common coordinate system (e.g., the localizer coordinate system LCLZ), and because the configuration of the guide assembly 88 is known based, among other things, on its geometry, the computing device 30 can dynamically adjust the arrangement of a virtual axis 156 (see FIGS. 9A-9C) within the virtual reference frame VRF such that the visual content VC is displayed in a correspondingly-dynamic fashion in order to compensate for relative movement occurring between the guide assembly 88 and other tracked objects. Here too, the navigation system 68 can track states of the second instrument tracker 70F to generate the guide location data GLD relative to the localizer coordinate system LCLZ. Moreover, it will be appreciated that guide location data GLD can be related to other tracked objects in a common coordinate system in different ways, such as where the tablet display unit 28A is fixed to the guide assembly 88 (not shown) and its camera 66 serves as the localizer 26 such that location data generated by the camera 66 is based on a coordinate system that moves with the tablet display unit 28A and, thus with, the guide assembly 88 fixed thereto. Other configurations are contemplated.

Figure 9A:
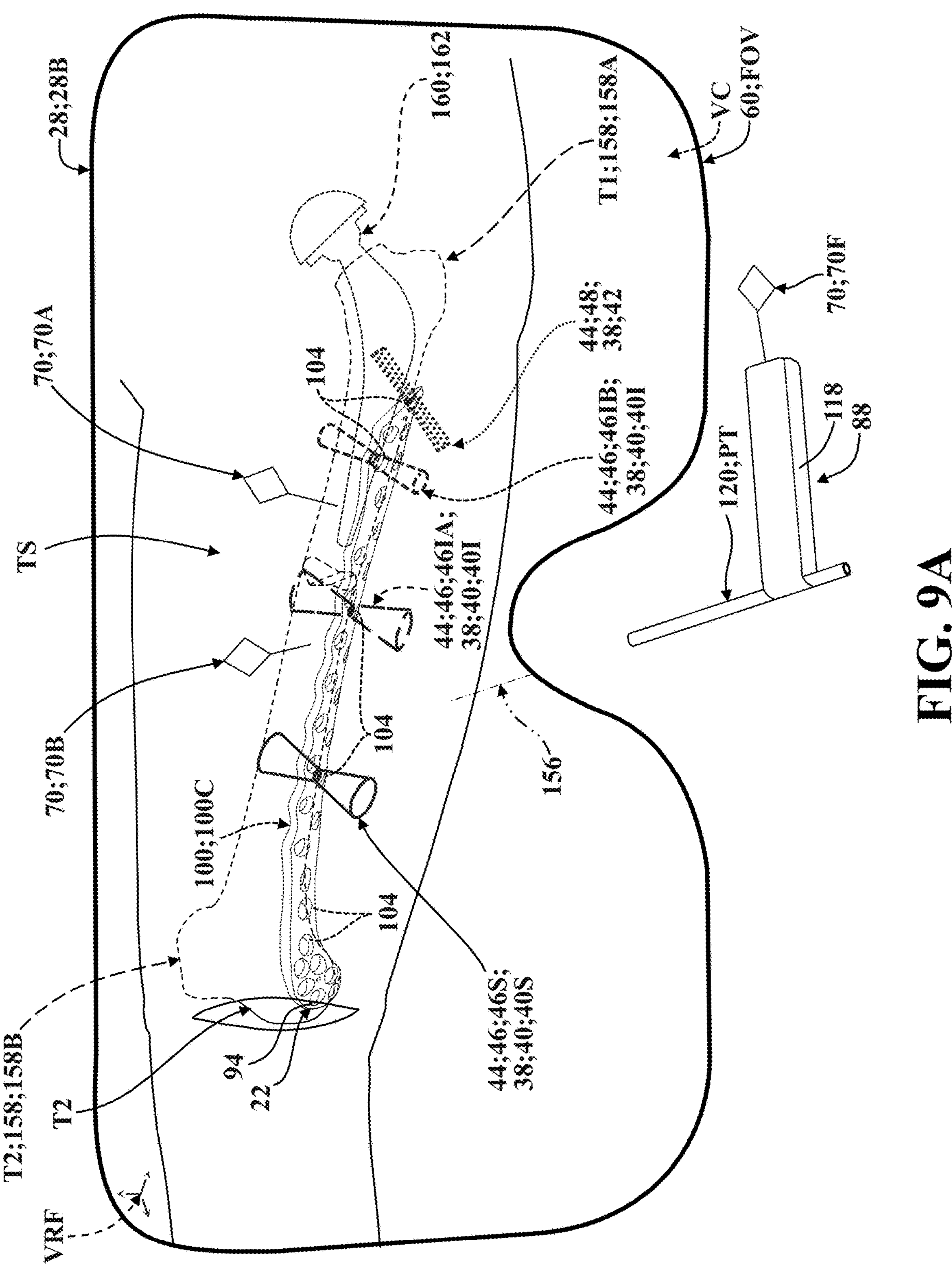
FIG. 9A is another partial perspective view of the patient's anatomy orientated as depicted in FIGS. 8A-8F, with the stabilizer arranged as depicted in FIGS. 8E-8F after being released from the handle assembly, with the guide assembly of FIG. 1 positioned spaced from the patient's anatomy, and shown as viewed through the head-mountable display unit displaying the visual content of FIG. 8F along with a virtual axis arranged fixed relative to the guide assembly and along with a virtual viability model comprising viable portions and non-viable portions, with the viable portions of the virtual viability model displayed as corridors associated with viable fixation approaches passing through virtual apertures of the virtual stabilizer model, and with the non-viable portions of the virtual viability model displayed as barrier indicia associated with non-viable fixation approaches adjacent to virtual apertures of the virtual stabilizer model.
Figure 9B:
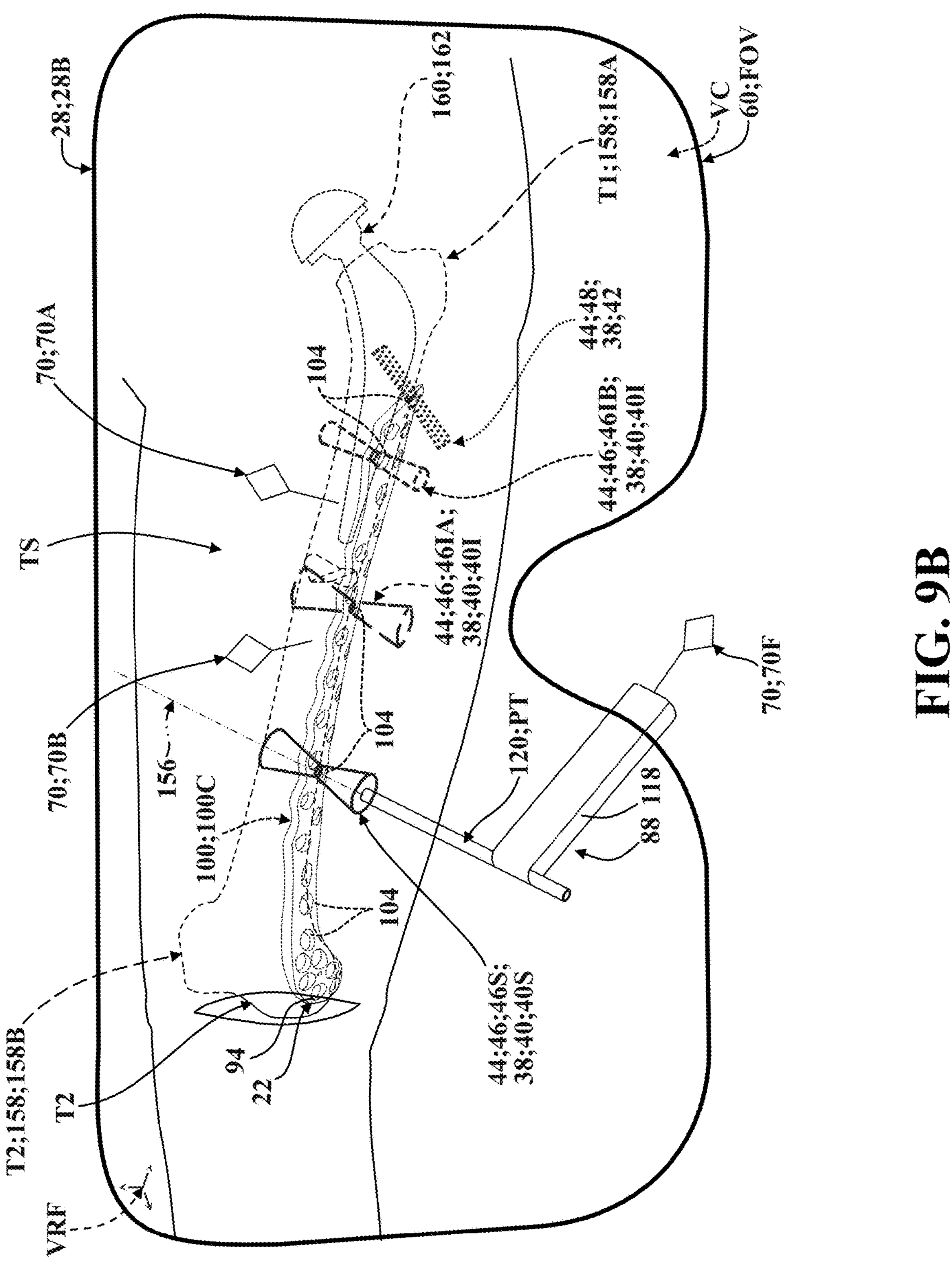
FIG. 9B is another partial perspective view of the patient's anatomy orientated as depicted in FIG. 9A, with a bore element of the guide assembly positioned engaging the patient's skin, shown as viewed through the head-mountable display unit displaying the visual content of FIG. 9A to illustrate the virtual axis extending through a first corridor and passing through one of the virtual apertures of the virtual stabilizer model.
Figure 9C:
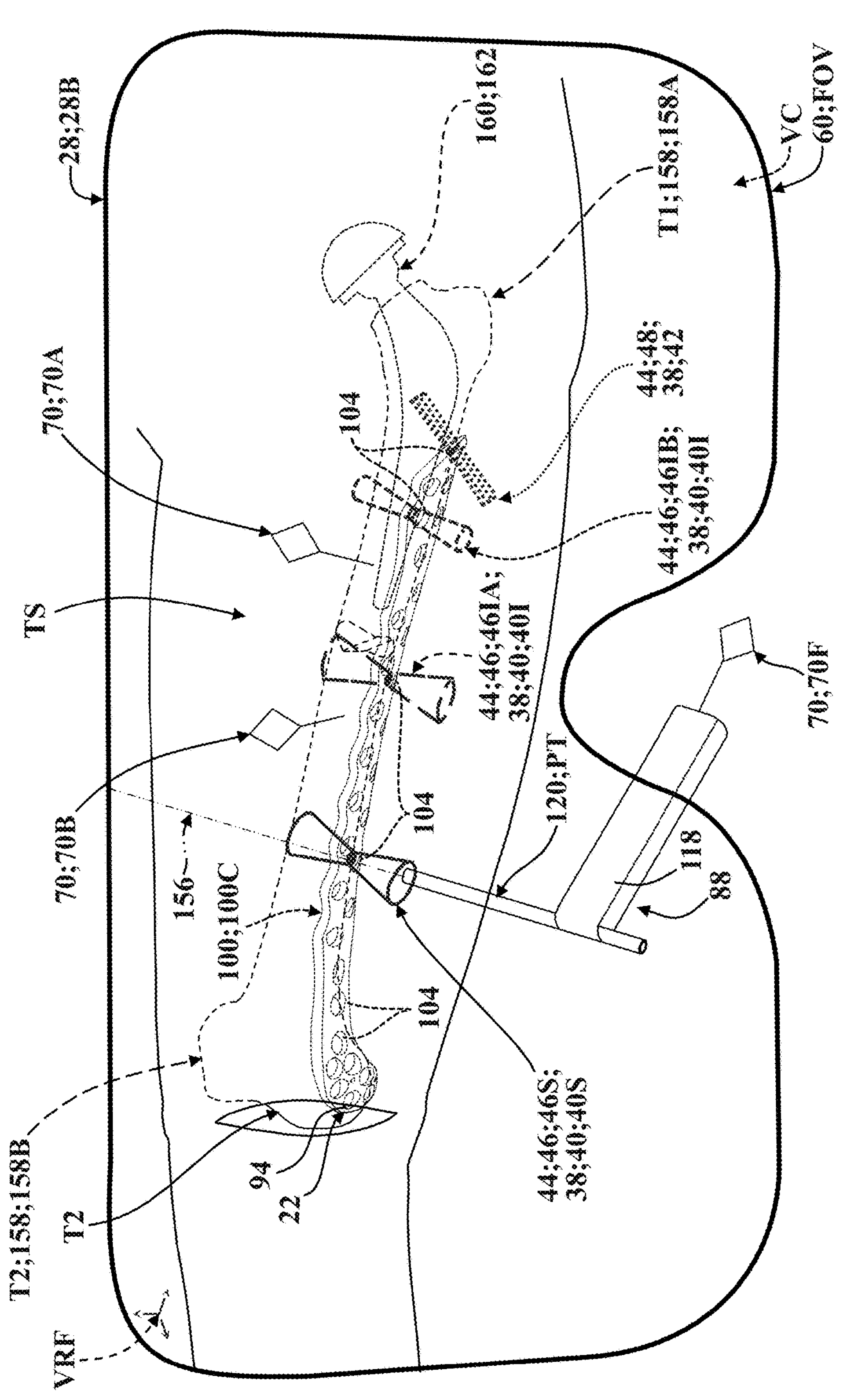
FIG. 9C is another partial perspective view of the patient's anatomy orientated as depicted in FIGS. 9A-9B, with the bore element of the guide assembly repositioned but still engaging the patient's skin, shown as viewed through the head-mountable display unit displaying the visual content of FIG. 9B to illustrate the virtual axis extending differently through the first corridor and still passing through the same virtual aperture of the virtual stabilizer model.

As noted above, in certain embodiments, the visualization program 36 is configured to arrange various virtual objects within the virtual reference frame VRF including, for example, the virtual viability model 44 (see, for example, FIGS. 7B-7D), the virtual stabilizer models 100 and the virtual fixation element models 122 (see, for example, FIGS. 3A-3C), and the virtual axis 156 (see FIGS. 9A-9C). Furthermore, and as is described in greater detail below, the visualization program 36 may also be configured to arrange one or more virtual patient models 158 (see, for example, FIG. 5C) and/or one or more virtual implant models 160 (see, for example, FIGS. 5B-7D) within the virtual reference frame VRF.

Referring now to FIGS. 4A-4D, the target site TS is shown orientated according to an anteroposterior view of a patient's anatomy that represents patient-specific imaging data ID that could have been generated either preoperatively or intraoperatively. In each of these views, the patient-specific imaging data ID is considered to be observable within the view FOV to help illustrate various aspects of the present disclosure. In this representative example, the target site TS is defined by portions of the patient's left femur which present comminuted fractures to bone tissue. According to various embodiments of the present disclosure, the visualization program 36 may be configured to arrange one or more virtual patient models 158 within the virtual reference frame VRF based on the patient location data PLD, and render at least a portion of the one or more virtual patient models 158 in the visual content VC displayed by the display unit 28 overlaid onto the patient's anatomy within the field of view FOV to assist the user in visualizing the one or more virtual patient models 158 adjacent to an unexposed portion of the target site TS (compare FIGS. 4A-4D).

In addition to displaying visual content VC overlaid onto portions of the patient's actual anatomy (e.g., as is depicted and described in greater detail below in connection with FIGS. 5A-10F), FIGS. 4A-4D illustrate that visual content VC (e.g., virtual patient models 158) can also be displayed overlaid onto portions of the patient's anatomy that are rendered or otherwise displayed (either statically and/or dynamically) as patient-specific imaging data ID but can nevertheless be registered and tracked relative to display units 28 in a common coordinate system. To this end, the patient-specific imaging data ID can be registered within the virtual reference frame VRF in various ways. For example, the user could employ a pointer device (not shown) to relate anatomical landmarks of the patient's anatomy to the tracker 70 fixed thereto, could identify anatomical landmarks via the patient-specific imaging data ID, and the like. Other configurations are contemplated.

Figure 4A:
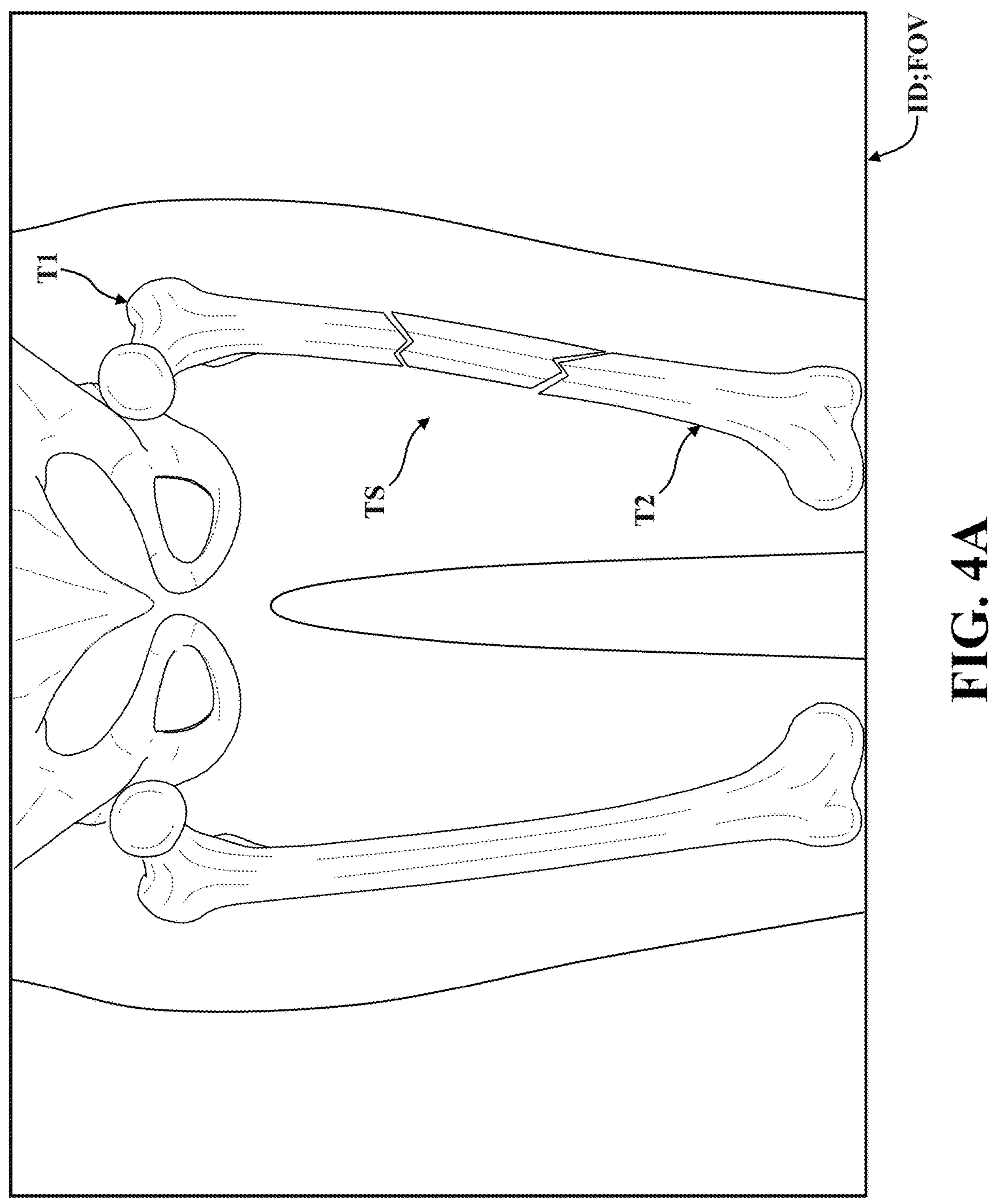
FIG. 4A illustrates an anteroposterior view of a patient's anatomy at a target site defined by portions of the patient's left femur shown with comminuted fractures to bone tissue.
Figure 4B:
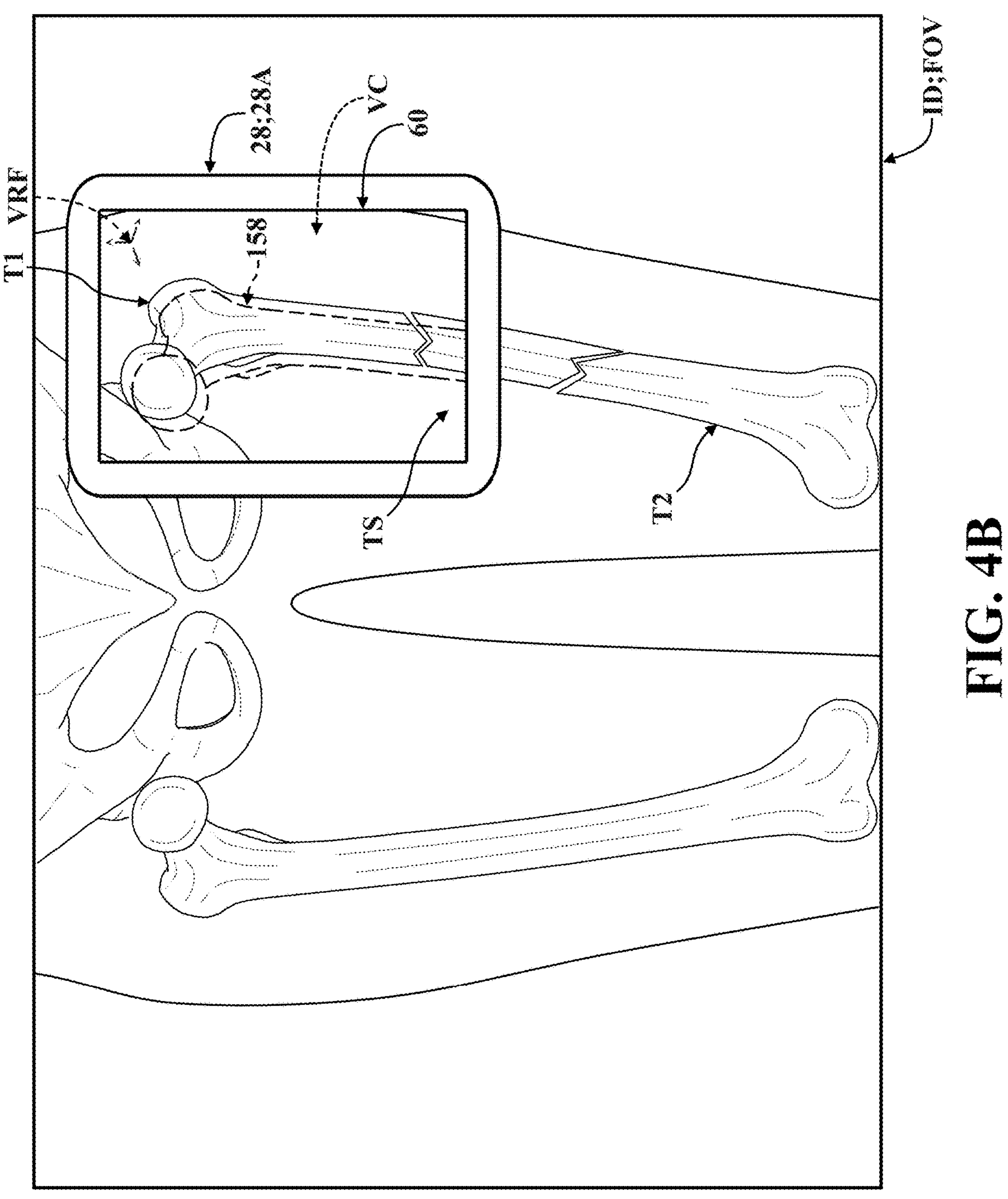
FIG. 4B illustrates another anteroposterior view of a patient's anatomy orientated as depicted in FIG. 4A, shown with a tablet display unit positioned adjacent to the target site and displaying a virtual patient model representing a non-fractured femur overlaid onto the fractured femur.
Figure 4C:
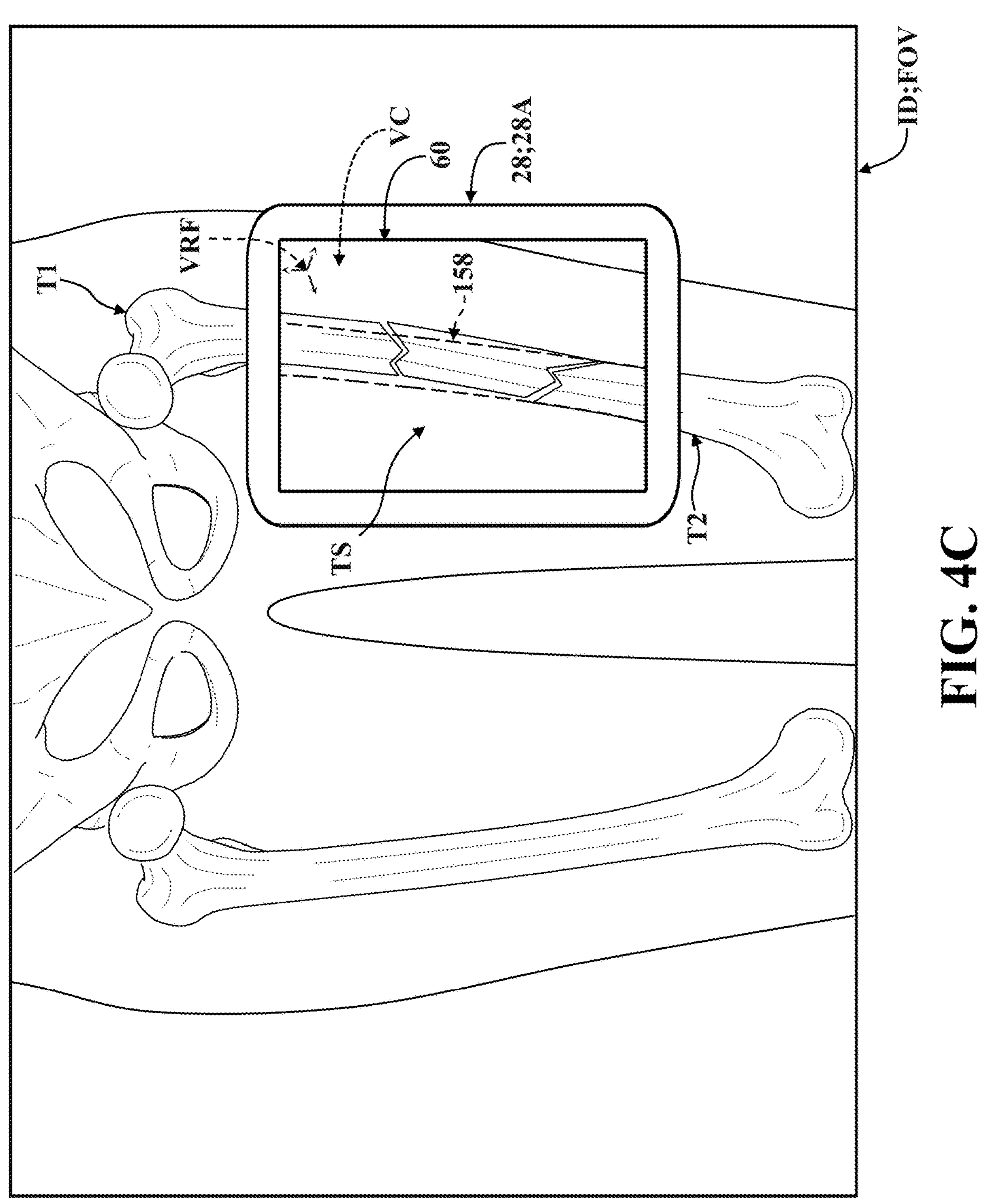
FIG. 4C illustrates another anteroposterior view of a patient's anatomy orientated as depicted in FIGS. 4A-4B, shown with the tablet repositioned adjacent to the target site and displaying the virtual patient model representing the non-fractured femur overlaid onto the fractured femur.
Figure 4D:
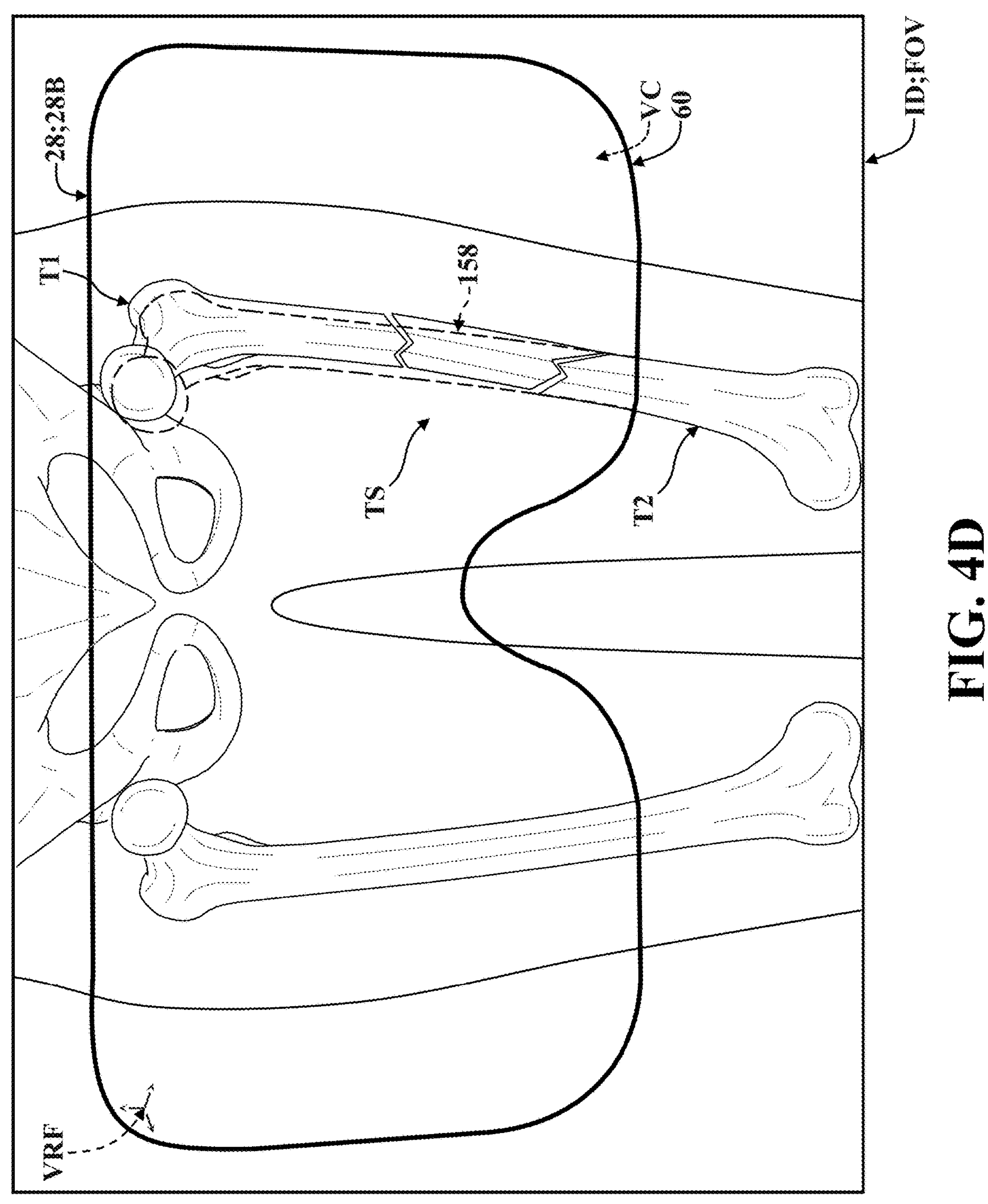
FIG. 4D illustrates another anteroposterior view of a patient's anatomy orientated as depicted in FIG. 4A-4C, shown as viewed through a head-mountable display unit displaying the virtual patient model representing the non-fractured femur overlaid onto the fractured femur.

In FIG. 4A, the patient-specific image data ID are represented with an anteroposterior view of a patient's anatomy at the target site TS defined by the patient's left femur shown with comminuted fractures to bone tissue. Here, in some embodiments, the surgical system 20 may be configured to arrange a virtual patient model 158 of the patient's left femur which represents an ideal postoperative result (e.g., a healthy femur) which can be overlaid onto the patient-specific imaging data ID to, among other things, aid in preoperative planning, intraoperative fracture reduction, general visualization of an unexposed portion of the target site TS in near-real time displayed overlaid onto the patient's anatomy (see FIGS. 4B-4D), and the like. To this end, the visualization program 36, or another portion of the surgical system 20, could construct the virtual patient model 158 depicted in FIGS. 4B-4D in a number of different ways. For example, patient-specific imaging data ID of tissue adjacent to the target site TS (e.g., each portion of the fractured left femur) could be utilized to construct separate 3D models for each portion of the fractured femur and then assemble those models into an assembly which represents the femur after fracture reduction, with the assembly serving as the virtual patient model 158 overlaid onto the patient's anatomy based on alignment with one or more portions of the fractured femur at the target site TS (see FIGS. 4B-4D). By way of further example, patient-specific imaging data ID of tissue arranged contralateral to the target site TS (e.g., the patient's right femur) could be used to construct a "mirrored" version of another part of the patient's actual anatomy to serve as the virtual patient model 158 (e.g., a healthy version of the patient's left femur). Furthermore, models of the tissue database 56 could be used to help generate the virtual patient model 158 in some embodiments. Here, it is contemplated that patient-specific imaging data ID of tissue adjacent to the target site TS could be combined with (or otherwise considered in view of) data from the tissue database 56 (e.g., models) and/or other surgical planning databases, systems, and the like (as well as other components of the surgical system 20) in various ways in order to generate or otherwise serve as the virtual patient model 158. By way of non-limiting example, if the surgical procedure involves correction of a bone deformity, the tissue database 56 could be used to generate the virtual patient model 158 in a way which represents a desired postoperative result after correcting the bone deformity reflected in the patient-specific imaging data ID of tissue adjacent to the target site TS. Other configurations are contemplated. Virtual patient models 158 could be constructed, generated, and/or arranged in ways similar to as is disclosed in one or more of: U.S. Pat. No. 9,508,149, entitled "Virtual 3D Overlay as Reduction Aid for Complex Fractures;" U.S. Pat. No. 10,070,903, entitled "Stereotactic Computer Assisted Surgery Method and System;" and U.S. Patent Application Publication No. 2018/0055573, entitled "Technique for Generating a Bone Plate Design," the disclosures of each of which are hereby incorporated by reference. Other configurations are contemplated, including without limitation those disclosed in other publications referenced herein.

Figure 5A:
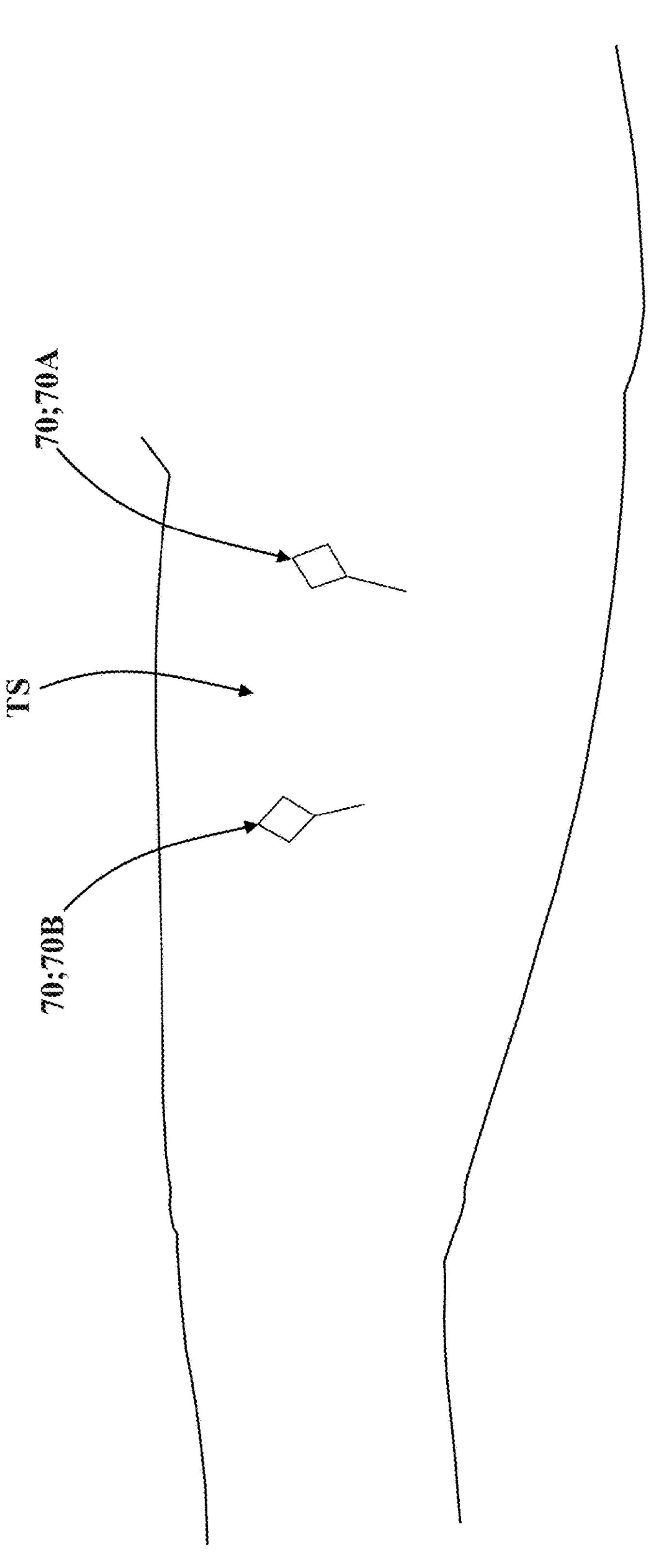
FIG. 5A is a partial perspective view of a patient's anatomy adjacent to a target site defined by portions of the patient's left femur, depicting patient trackers of the navigation system of FIG. 1 attached to different portions of the patient's anatomy.
Figure 5A:
Figure 5B:
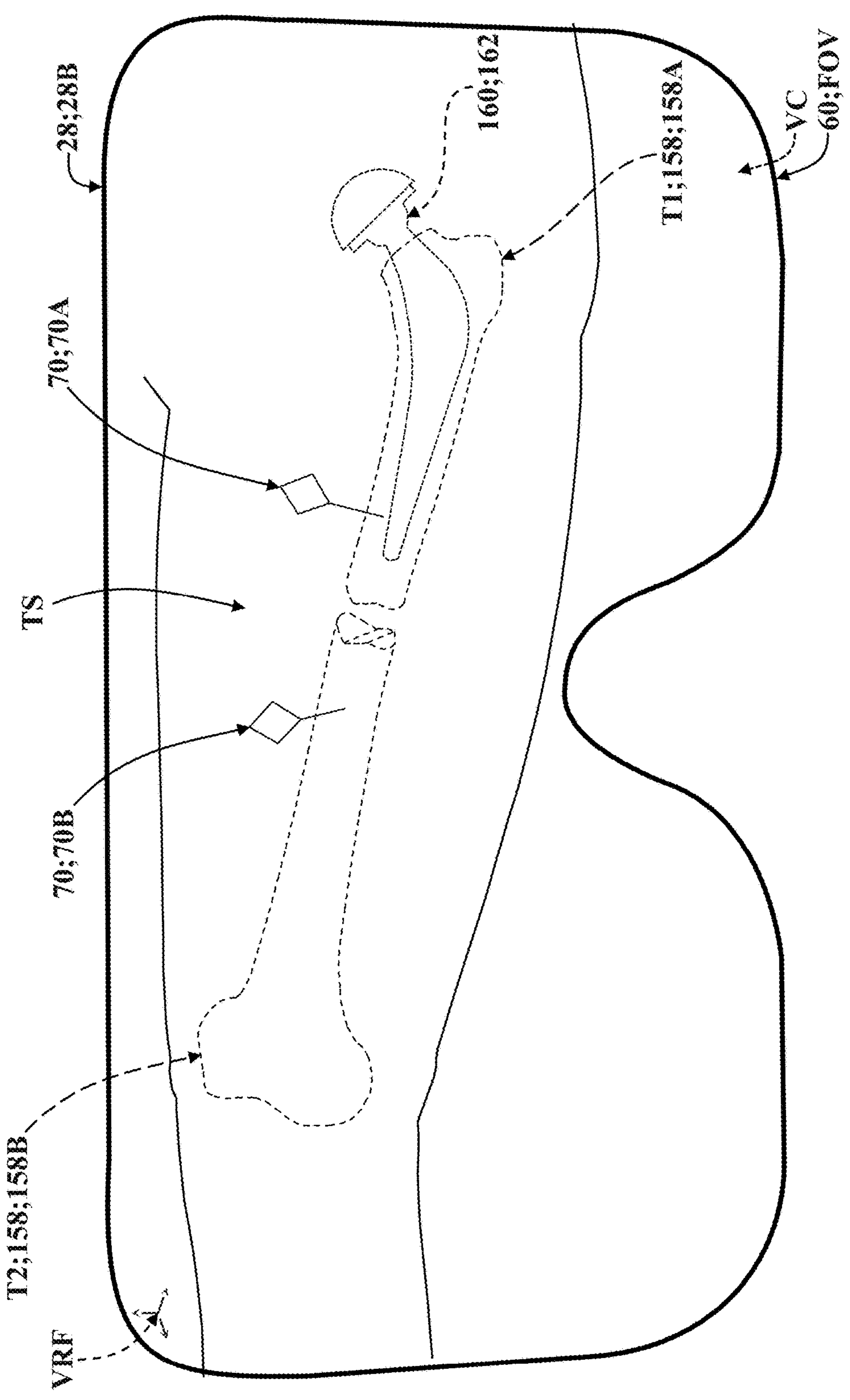
FIG. 5B is another partial perspective view the patient's anatomy orientated as depicted in FIG. 5A, shown as viewed through a head-mountable display unit displaying visual content comprising virtual patient models and a virtual implant model overlaid onto an unexposed portion of the patient's anatomy to illustrate a diaphyseal periprosthetic fracture at the target site.
Figure 5C:
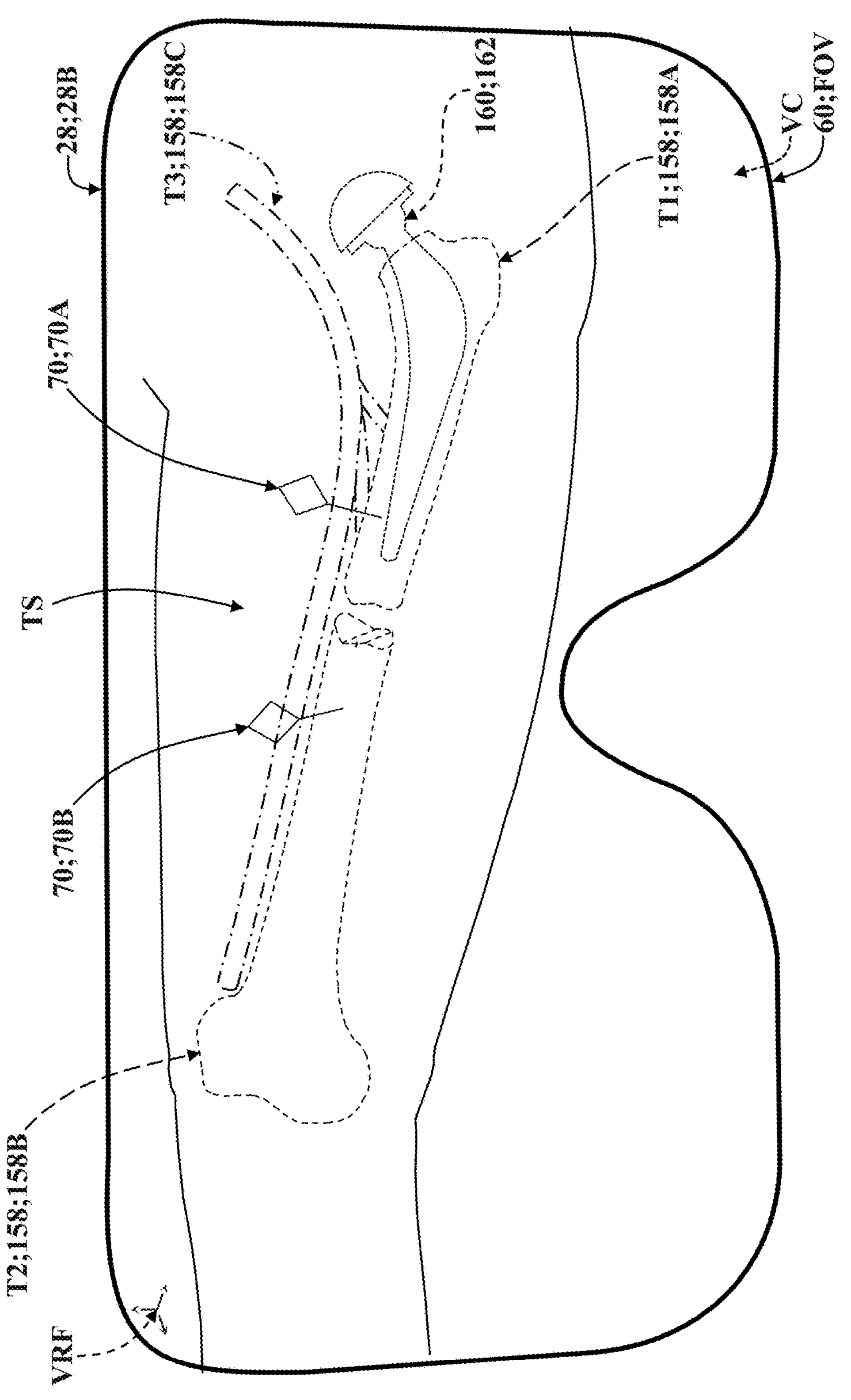
FIG. 5C another partial perspective view of the patient's anatomy orientated as depicted in FIGS. 5A-5B, shown as viewed through the head-mountable display unit displaying the visual content of FIG. 5B along with another virtual patient model to illustrate arterial tissue adjacent to the target site.

Referring now to FIGS. 5A-5C, partial perspective views of the patient's left leg are shown adjacent to the target site TS, here too defined by the patient's left femur. However, in this illustrative example, the patient's left femur presents a diaphyseal periprosthetic fracture, which is depicted in FIG. 5B by visual content VC of the virtual reference frame VRF displayed via the head-mountable display unit 28B onto an unexposed portion of the patient's anatomy at the target site TS (e.g., via augmented reality and/or mixed reality). More specifically, in FIG. 5B, the visual content VC comprise a first virtual patient model 158A representing a first tissue portion T1 of the patient's left femur (defined here by attachment to the first patient tracker 70A), a second virtual patient model 158B representing a second tissue portion T2 of the patient's left femur (defined here by attachment to the second patient tracker 70B), and a virtual implant model 160 shown fixed to the second tissue portion T2.

In this illustrative example, the virtual implant model 160 shown in FIG. 5B (and in other drawing views) also represents a corresponding implanted component 162 that was attached to the patient's left femur during a previous surgical procedure. Here, the virtual implant model 160 may be constructed, generated, or otherwise identified by the visualization program 36 (or another part of the surgical system 20) in a number of different ways. By way of illustrative example, patient-specific imaging data ID of the target site TS could be used to identify the specific configuration and/or pose of the implanted component 162 based on its geometry, markers, or other indicia, and could generate and arrange a corresponding virtual implant model 160 arranged in the virtual reference frame VRF.

Here, the visualization program 36 could comprise or otherwise have access to an implant database 164 and/or to a medical records database 166 associated with the patient's surgical history (see FIG. 2) to aid in the identification of the implanted component 162. Here, for example, the user could manually input data associated with the implanted component 162 (e.g., a make, model, and/or serial number), and the visualization program 36 could compare the inputted data against one or more of the patient's records in the medical records database 166, and/or could compare measured geometry of the implanted component 162 depicted in the patient-specific imaging data ID against geometry data stored in the implant database 164. Other configurations are contemplated. Once identified by the visualization program 36, one or more virtual implant models 160 could be arranged within the virtual reference frame VRF based on the patient location data PLD, with at least a portion of the one or more virtual implant models 160 rendered in the visual content VC displayed by the display unit 28 overlaid onto the patient's anatomy within the field of view FOV to assist the user in visualizing the one or more virtual implant models 160 (and, thus, the corresponding implanted component 162) adjacent to an unexposed portion of the target site TS (e.g., with augmented reality and/or mixed reality via the head-mountable display unit).

In addition to being able to identify tissue portions at the target site TS which comprise portions of fractured bone and generate corresponding virtual patient models which represent those portions of fractured bone within the virtual reference frame VRF, in some embodiments the visualization program 36 (or another part of the surgical system 20) could also identify other types of tissue and construct or otherwise generate corresponding virtual patient models 158 in the virtual reference frame VRF. For example, soft tissues could be identified and related to the target site TS within the virtual reference frame VRF (and, in some embodiments, rendered as visual content VC) based such as on patient-specific imaging data ID generated via computed tomography (e.g., a "CT scan"), magnetic resonance imaging (MRI), ultrasonography, near-infrared (NIR) fluorescence, Terahertz radiation, and the like. This concept is illustrated in FIG. 5C, which depicts a third virtual patient model 158C representing a third tissue portion T3 defined as arterial tissue arranged adjacent to the target site TS. Thus, it will be appreciated that the visualization program 36 could identify a plurality of different tissue portions T1, T2, T3, of the same or different types of tissue, adjacent to the target site TS based on the patient-specific imaging data ID. Moreover, it will be appreciated that a number of different types of tissue could be represented in or otherwise form part of the virtual patient model 158, including without limitation various types of bone, marrow, muscle, nerve, epithelial, and/or connective tissue.

As will be appreciated from the subsequent description below, the identification of fixation approaches 38 and/or the delineation between viable fixation approaches 40 and non-viable fixation approaches 42 may be based on a number of different considerations, factors, and the like. By way of illustrative example, the visualization program 36 may be configured to identify fixation approaches 38 for generating and/or arranging the virtual viability model 44 based on the relative geometry and arrangement (or proposed arrangement) of different virtual objects within the virtual reference frame VRF (whether rendered in the displayed visual content VC or not). This may include one or more virtual patient models 158, one or more virtual implant models 160, one or more virtual stabilizer models 100, and/or one or more virtual fixation element models 122.

By way of illustrative example, the visualization program 36 may be configured to initially identify a set of fixation approaches 38 based on geometry of a selected virtual stabilizer model 100 (e.g., each fixation approach 38 being associated with a virtual aperture 104), and may delineate fixation approaches 38 based at least partially on the arrangement between different tissue portions T1, T2, T3 (and, in some embodiments, the relative arrangements of regions thereof, as described in greater detail below). Put differently, fixation approaches 38 that would likely result in damage to soft tissue may be delineated as non-viable fixation approaches 42. By way of similar illustrative example, the visualization program 36 may be configured to delineate fixation approaches 38 based at least partially on the arrangement of the one or more implanted components 162. Put differently, fixation approaches 38 that would likely result in collision with an existing, identified implanted component 162 may be delineated as non-viable fixation approaches 42. By way of further illustrative example, and according to certain embodiments described in greater detail below, the visualization program 36 may be configured to further delineate viable fixation approaches 40 between superior fixation approaches 40S and inferior fixation approaches 40I based, among other things, on the patient-specific imaging data ID. This allows tissue stabilization to be optimized by "ranking" viable fixation approaches 40 based on a number of different parameters, variables, and the like, as is described in connection with FIGS. 7A-10F. Other configurations are contemplated.

Referring now to FIGS. 6A-6E, the handle assembly 86 is shown adjacent to an unexposed portion of the target site TS of the patient's anatomy to illustrate how the surgical system 20 can be employed to facilitate "virtual trialing" of different stabilizers 22. To this end, and in some embodiments of the present disclosure, the visualization program 36 is configured to enable selection of one or more virtual stabilizer models 100 for arrangement within the virtual reference frame VRF with at least one of the one or more virtual stabilizer models 100 defining a plurality of virtual apertures 104 arranged relative to the corresponding plurality of apertures 94 defined by the respective stabilizer 22 which corresponds to the selected virtual stabilizer model 100. Put differently, the user can select a virtual representation of any of the stabilizers 22 available in a stabilization kit 90 (e.g., as described above in connection with FIGS. 3A-3C), and its corresponding virtual stabilizer model 100 can be arranged within the virtual reference frame VRF based on the handle location data HLD. Thus, the selected virtual stabilizer model 100 can be rendered in the visual content VC displayed by the display unit 28 overlaid onto the patient's anatomy within the field of view FOV to assist the user in visualizing the selected virtual stabilizer model 100 relative to, among other things, one or more virtual patient models 158, one or more virtual implant models 160, or other virtual objects within the virtual reference frame VRF (e.g., the virtual viability model 44).

Figure 6A:
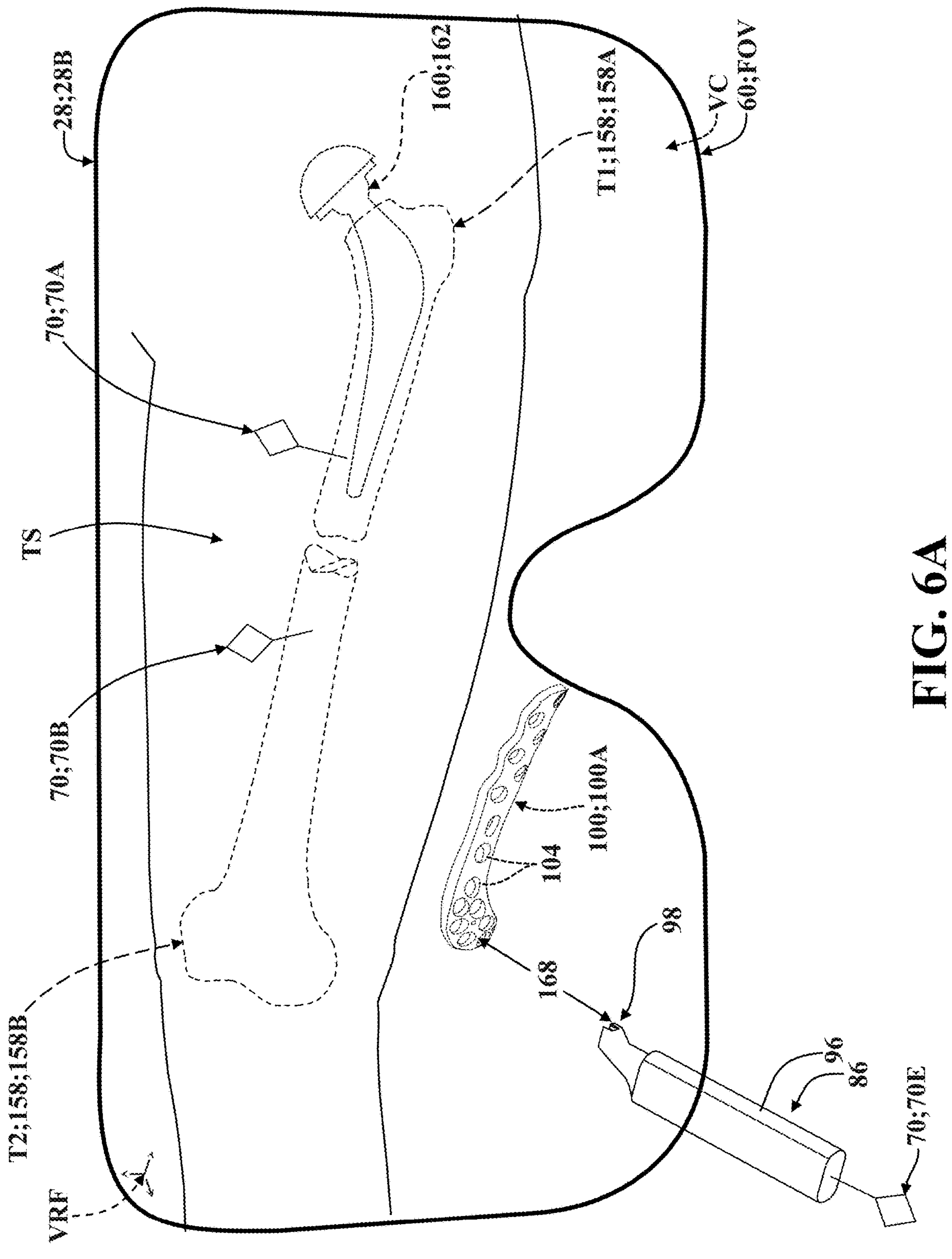
FIG. 6A is another partial perspective view of the patient's anatomy orientated as depicted in FIGS. 5A-5C, with the handle assembly of FIG. 1 positioned spaced from the patient's anatomy, and shown as viewed through the head-mountable display unit displaying the visual content of FIG. 5B along with a first virtual stabilizer model displayed offset from the handle assembly.
Figure 6B:
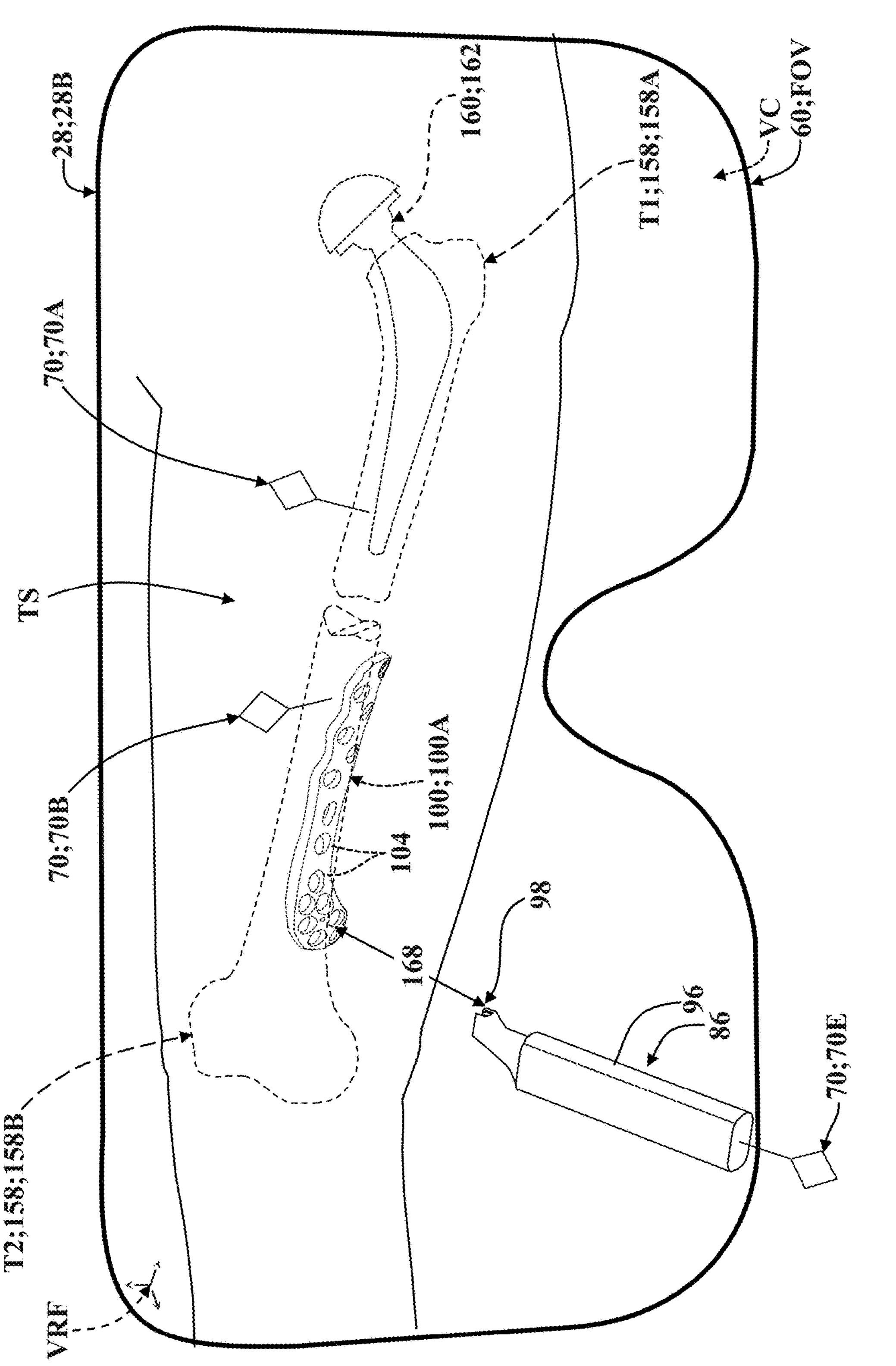
FIG. 6B is another partial perspective view of the patient's anatomy orientated as depicted in FIGS. 5A-6A, with the handle assembly of FIG. 6A repositioned but still spaced from the patient's anatomy, and shown as viewed through the head-mountable display unit displaying the visual content of FIG. 6A with the first virtual stabilizer model displayed offset from the handle assembly.
Figure 6C:
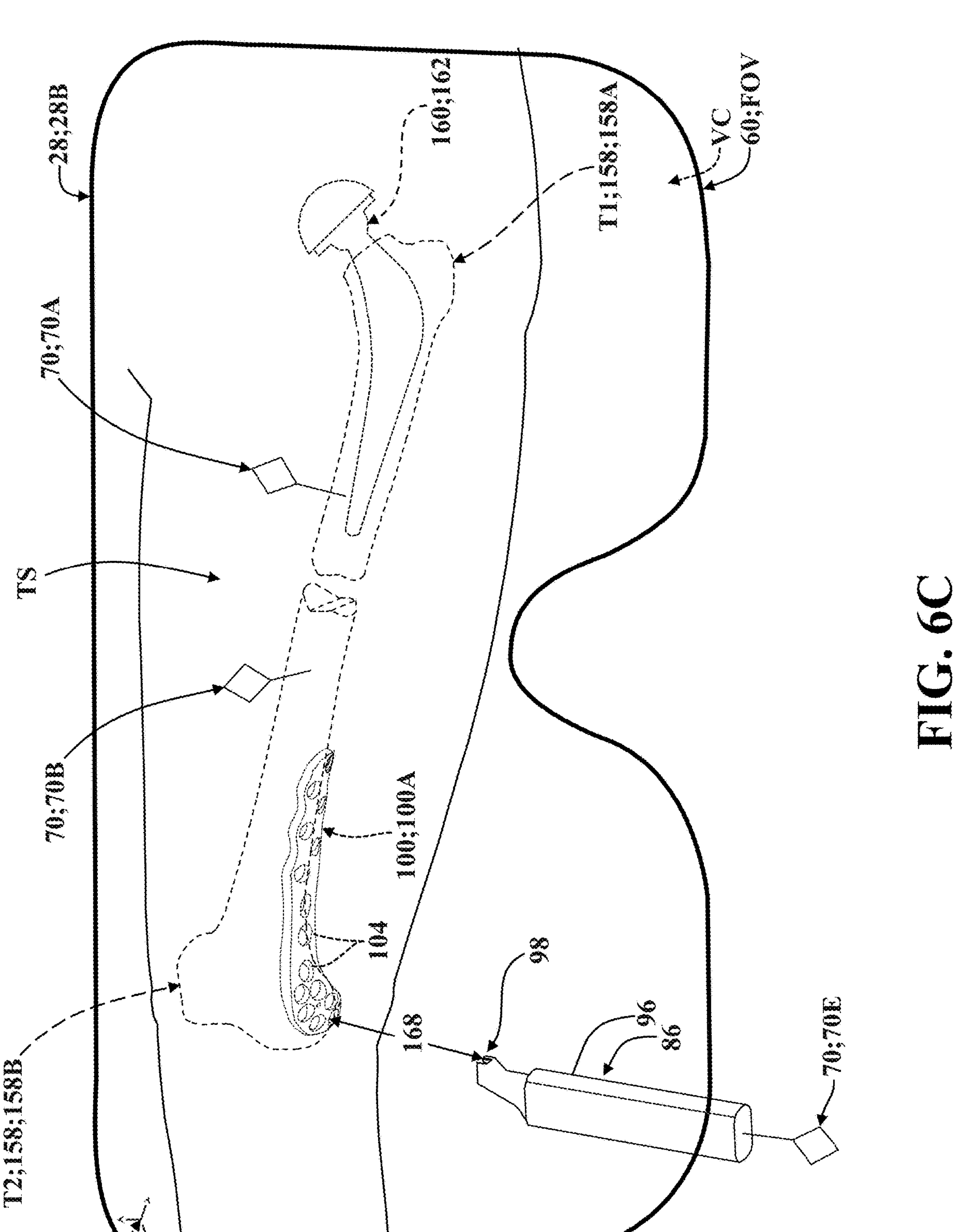
FIG. 6C is another partial perspective view of the patient's anatomy orientated as depicted in FIGS. 5A-6B, with the handle assembly of FIGS. 6A-6B again repositioned but still spaced from the patient's anatomy, and shown as viewed through the head-mountable display unit displaying the visual content of FIGS. 6A-6B with the first virtual stabilizer model displayed offset from the handle assembly.

In the illustrative example depicted in FIGS. 6A-6C, the user has selected a first virtual stabilizer model 100A using the visualization program 36, which is arranged within the virtual reference frame VRF based on the handle location data HLD in an offset relation RO at an offset distance 168 (e.g., as may be adjusted by the user via the visualization program 36) such that the selected first virtual stabilizer model 100A is rendered in the visual content VC displayed by the display unit 28 as offset from the coupler 98 of the handle assembly 86 within the field of view FOV to assist the user in visualizing the stabilizer 22 which corresponds to the selected first virtual stabilizer model 100A as offset from the coupler 98 of the handle assembly 86. This allows the user dynamically visualize the selected first virtual stabilizer model 100A at the unexposed target site TS in various positions and orientations by adjusting the position of the handle assembly 86, and visualize the corresponding position and orientation of the first virtual stabilizer model 100A relative to other objects within the virtual reference frame VRF, such as the first and second virtual patient models 158A, 158B and the virtual implant model 160 depicted in FIGS. 6A-6C.

Here in this illustrative example, FIG. 6A depicts the user having initially selected the first virtual stabilizer model 100A, and FIG. 6B depicts the user adjusting the pose of the handle assembly 86 relative to the target site TS to effect a corresponding adjustment in the pose of the selected first virtual stabilizer model 100A in offset relation RO at the offset distance 168. FIG. 6C depicts the user having further adjusted the pose of the handle assembly 86 relative to the target site TS to effect a corresponding further adjustment in the pose of the selected first virtual stabilizer model 100A in offset relation RO at the offset distance 168. Here in FIG. 6C, the visual comparison between the selected first stabilizer model 100A and the first and second virtual patient models 158A, 158B provide the user with a visualization which represents "virtual trialing" of the stabilizer 22 corresponding to the selected first stabilizer model 100A. Here, the user can readily appreciate that the stabilizer 22 corresponding to the selected first stabilizer model 100A will be insufficient to stabilize the first and second tissue portions T1, T2 of the patient's femur based on the similarly corresponding arrangement of the first and second virtual patient models 158A, 158B which correspond to the first and second tissue portions T1, T2.

Figure 6D:
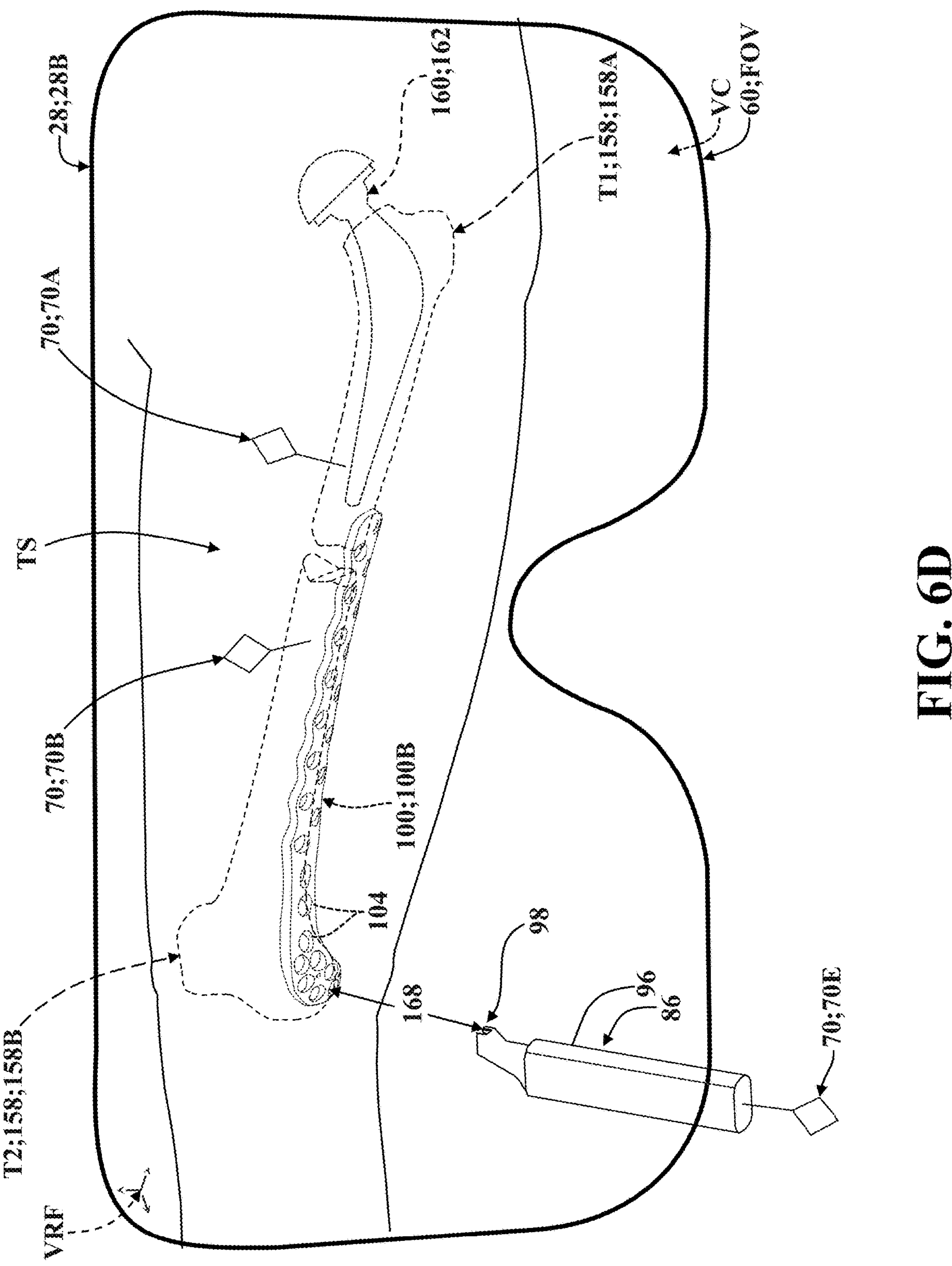
FIG. 6D is another partial perspective view of the patient's anatomy orientated as depicted in FIGS. 5A-6C, with the handle assembly arranged as depicted in FIG. 6C, and shown as viewed through the head-mountable display unit displaying the visual content of FIG. 5B along with a second virtual stabilizer model displayed offset from the handle assembly.
Figure 6E:
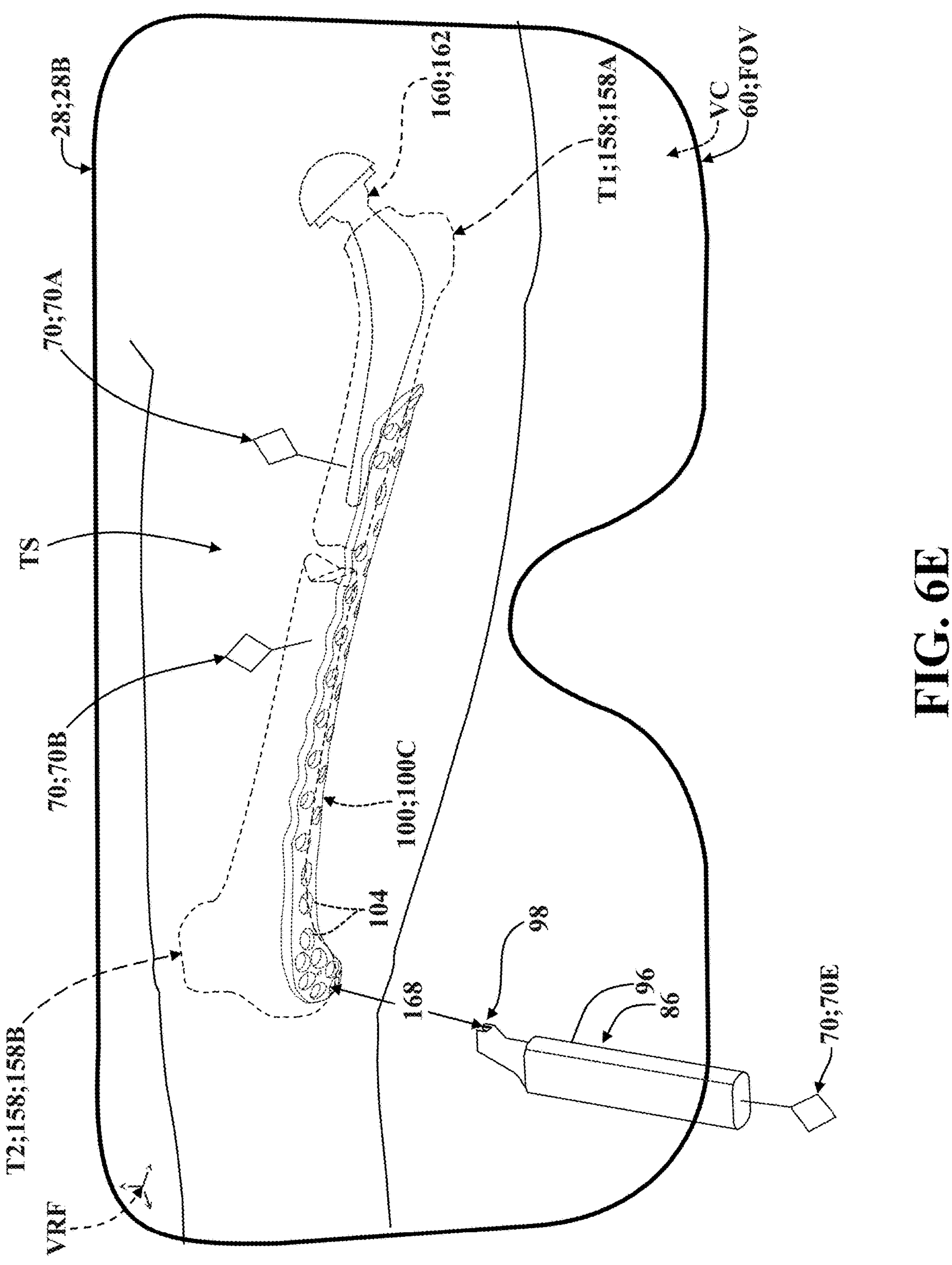
FIG. 6E is another partial perspective view of the patient's anatomy orientated as depicted in FIGS. 5A-6D, with the handle assembly arranged as depicted in FIG. 6C, and shown as viewed through the head-mountable display unit displaying the visual content of FIG. 5B along with a third virtual stabilizer model displayed offset from the handle assembly.

Because the selected first virtual stabilizer model 100A depicted in FIG. 6C does not sufficiently extend between the first and second tissue portions T1, T2 of the femur represented by the first and second virtual patient models 158A, 158B, the user subsequently selects a second virtual stabilizer model 100B as depicted in FIG. 6D. Here too, the user can readily visualize the selected second virtual stabilizer model 100B relative to the first and second virtual patient models 158A, 158B to effect "virtual trialing" of the stabilizer 22 which corresponds to the second virtual stabilizer model 100B. Because the selected second virtual stabilizer model 100B depicted in FIG. 6D does not sufficiently extend between the first and second tissue portions T1, T2 of the femur represented by the first and second virtual patient models 158A, 158B, the user subsequently selects a third virtual stabilizer model 100C as depicted in FIG. 6E. Here too, the user can readily visualize the selected second virtual stabilizer model 100B relative to the first and second virtual patient models 158A, 158B to effect "virtual trialing" of the stabilizer 22 which corresponds to the second virtual stabilizer model 100B. Those having ordinary skill in the art will appreciate that the ability to effect "virtual trialing" via the embodiments of the present disclosure affords significant advantages in connection with a variety of different types of medical and surgical procedures, including without limitation reduced intervention time and significantly minimized exposure of the target site TS to potential contaminants, infection, and the like.

Figure 7A:
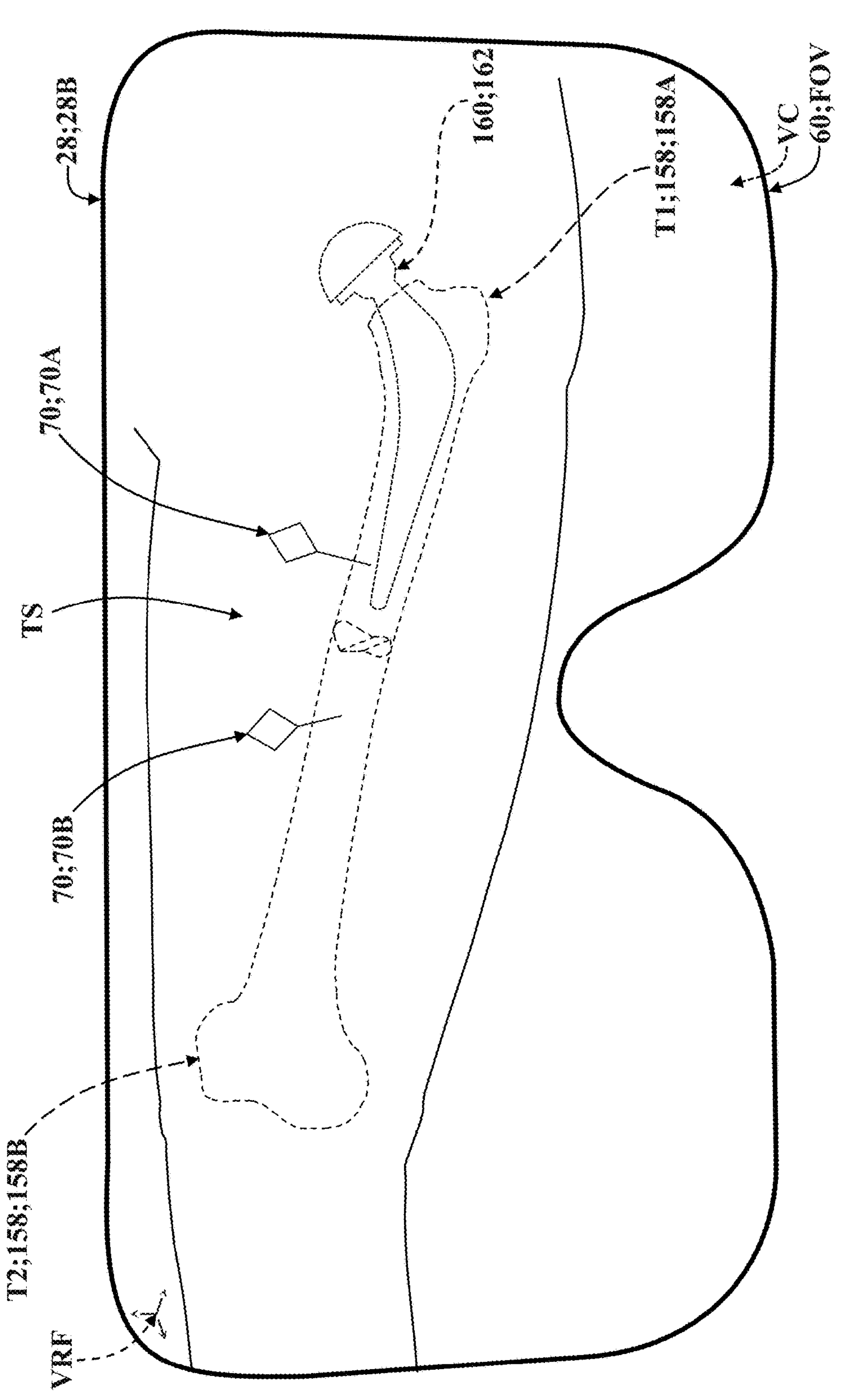
FIG. 7A is a partial perspective view of a patient's anatomy adjacent to a target site defined by portions of the patient's left femur, depicting patient trackers of the navigation system of FIG. 1 attached to different portions of the patient's anatomy, and shown as viewed through a head-mountable display unit displaying visual content comprising virtual patient models and a virtual implant model overlaid onto an unexposed portion of the patient's anatomy to illustrate a reduced diaphyseal periprosthetic fracture at the target site.
Figure 7B:
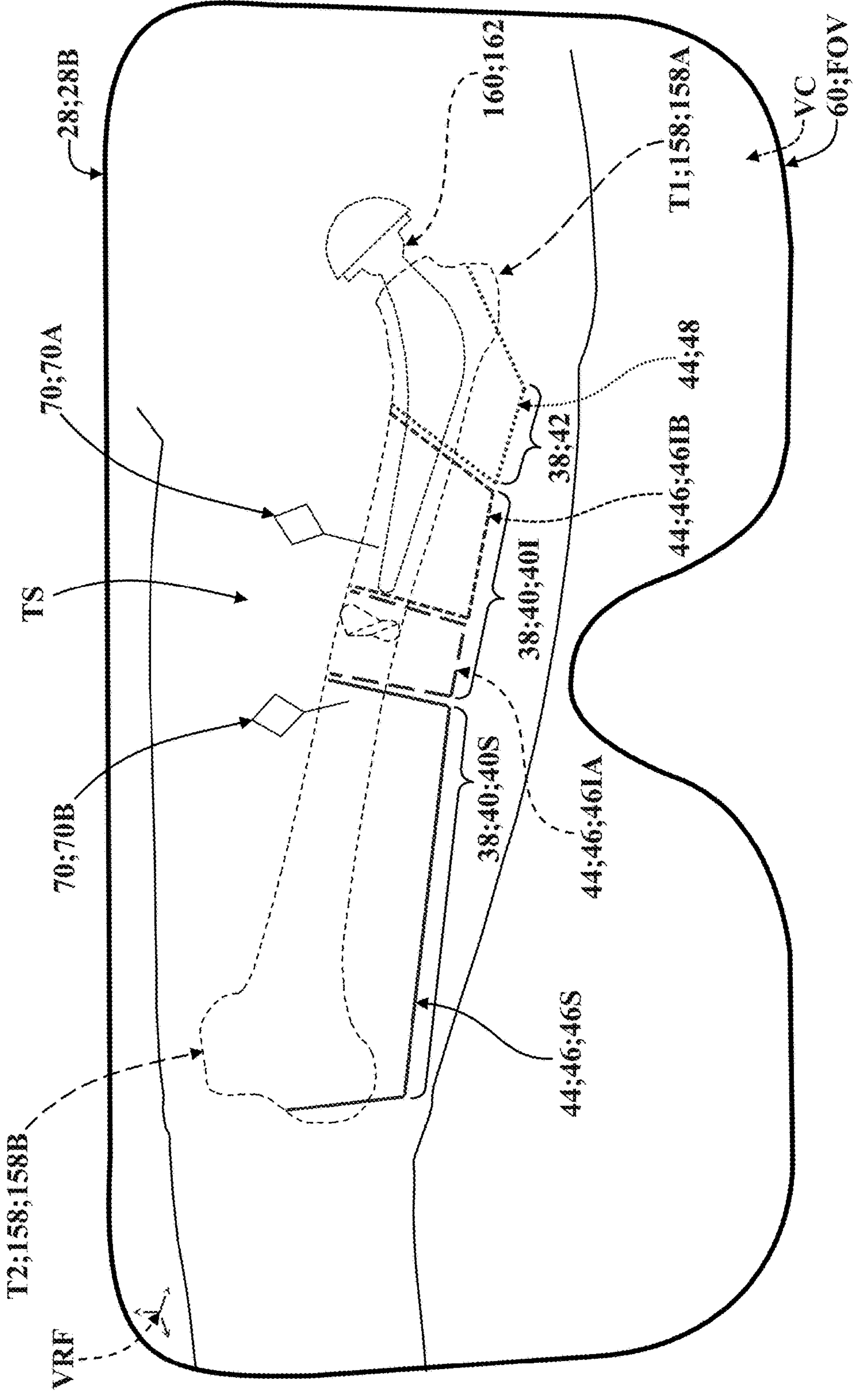
FIG. 7B is another partial perspective view of the patient's anatomy orientated as depicted in FIG. 7A, shown as viewed through the head-mountable display unit displaying the visual content of FIG. 7A along with a virtual viability model comprising viable portions and non-viable portions, with the viable portions of the virtual viability model displayed as proposed regions associated with viable fixation approaches, and with the non-viable portions of the virtual viability model displayed as proposed regions associated with non-viable fixation approaches.

Referring now to FIGS. 7A-7D, the target site TS is shown visualized through the head-mountable display unit 28B to depict a reduced diaphyseal periprosthetic fracture at the unexposed target site TS. More specifically, FIG. 7A depicts visual content VC comprising the first and second virtual patient models 158A, 158B corresponding to the first and second tissue portions T1, T2 of the patient's left femur, and the virtual implant model 160 corresponding to the implanted component 162 (e.g., prosthetics, stabilizers, fixation elements, and the like from a previous total hip joint replacement). FIG. 7B is similar to FIG. 7A, but also depicts a rendered virtual viability model 44 depicting viable portions 46 and non-viable portions 48 as regions (or "areas") delineated from each other according to one embodiment of the present disclosure. More specifically, FIG. 7B depicts the virtual viability model 44 as comprising a total of four exemplary portions, including three viable portions 46 associated with viable fixation approaches 40, and one non-viable portion 48 associated with non-viable fixation approaches 42. Here, one of the viable portions 46 comprises a superior viability portion 46A associated with one or more superior fixation approaches 40S, while the other two viable portions 46 comprise first and second inferior viability portions 46IA, 46IB associated with one or more inferior fixation approaches 40I, each of which are described in greater detail below.

In the illustrative example shown in FIG. 7B, the superior viability portion 46A of the virtual viability model 44 is depicted as a region of the first tissue portion T1 which is not within close proximity to either the fracture location (e.g., between the first and second tissue portions T1, T2 represented by the first and second virtual patient models 158A, 158B) or the implanted component 162 (e.g., the implant represented by the virtual implant model 160). Put differently, the superior viability portion 46A may be represented by an area or volume through which one or more discrete superior fixation approaches 40S pass (e.g., linear penetration trajectories PT; not shown in detail). On the other hand, the first inferior viability portion 46IA in FIG. 7B is depicted by regions of the first and second tissue portions T1, T2 which are adjacent to the fracture location, but still represent one or more inferior viable fixation approaches 40I (which, as noted above, are nevertheless viable fixation approaches 40). Similarly, the second inferior viability portion 46IB in FIG. 7B is depicted by a region of the second tissue portion T2 which is adjacent to the implanted component 162, but still represents one or more inferior viable fixation approaches 40I. On the other hand, the non-viable portion 48 of the virtual viability model 44 shown in FIG. 7B is depicted by a region of the second tissue portion T2 which is adjacent to the implanted component 162 and only represents non-viable fixation approaches 42. It will be appreciated that the forgoing is intended to be an illustrative and non-limiting example of one way in which the virtual viability model 44 can be delineated into viable portions 46 and non-viable portions 48, and also how viable portions 46 can be "ranked" or otherwise differentiated from each other based on superior fixation approaches 40S and/or inferior fixation approaches 40I.

Furthermore, those having ordinary skill in the art will appreciate that fixation approaches 38 could be delineated in a number of different ways, including without limitation one or more of: the geometry of the stabilizer 22 and/or fixation elements 24 being used, the location of one or more fractures at the target site TS, the geometry of one or more implanted components 162 or other material (e.g., bone cement), the proximity to soft tissue (e.g., arteries, veins, nerves, and the like), and/or patient-specific tissue characteristics (e.g., bone density, the presence of bone cement, and the like). Thus, it will also be appreciated that changing certain criteria, variables, parameters, and the like may result in corresponding changes in how a fixation approach 38 is identified or delineated. By way of illustrative example, a superior fixation approach 40S could be defined based on a fixation element 24 of a particular type and length being inserted through a specific aperture 94 of a selected stabilizer 22, but that same fixation approach 38 may become an inferior viable fixation approach 40I if a slightly longer fixation element 24 is selected, and may even become a non-viable fixation approach 42 if an even longer fixation element 24 is selected. Here too, the above example is intended to be illustrative and non-limiting.

Figure 7C:
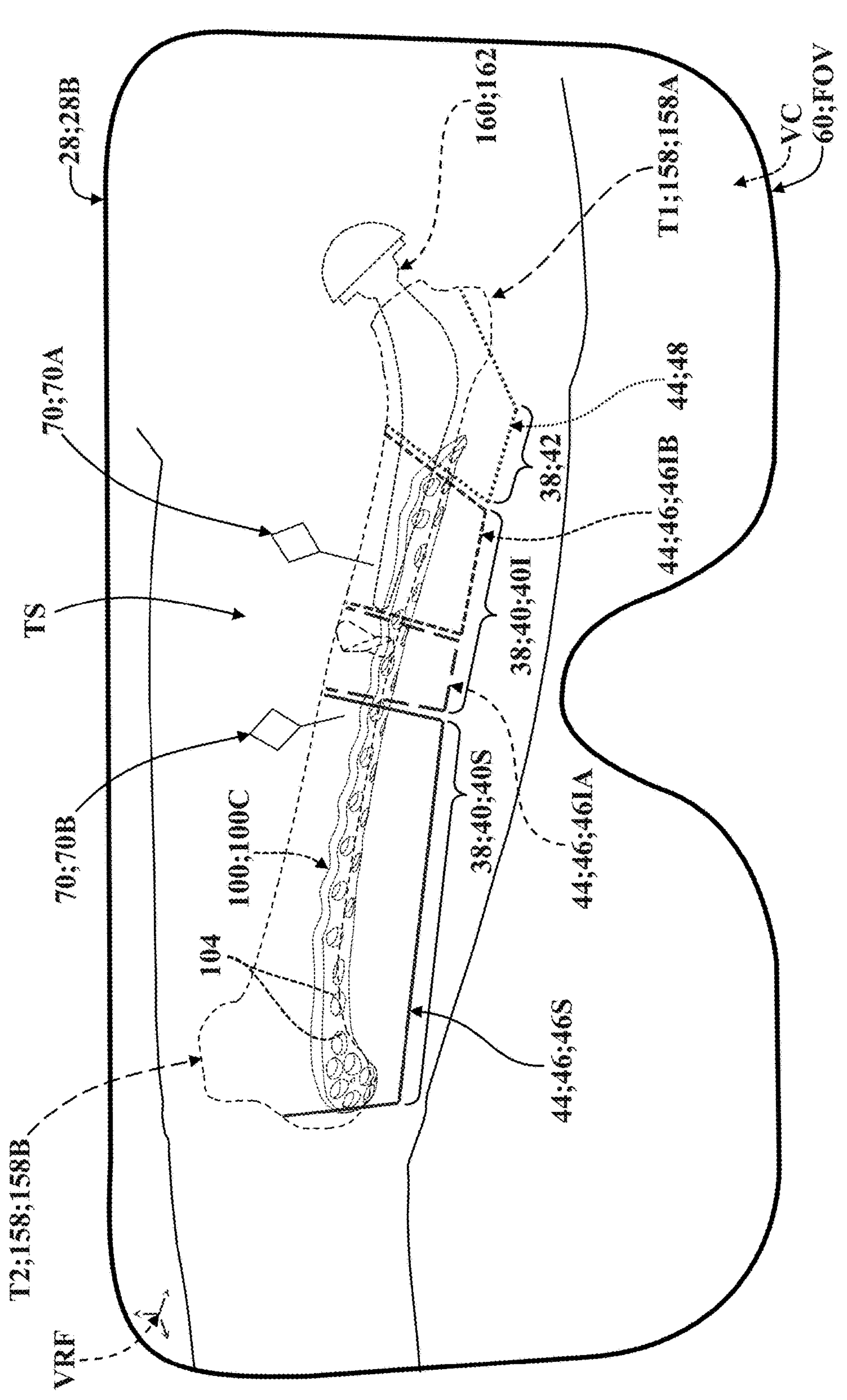
FIG. 7C is another partial perspective view of the patient's anatomy orientated as depicted in FIGS. 7A-7B, shown as viewed through the head-mountable display unit displaying the visual content of FIG. 7B along with a virtual stabilizer model comprising virtual apertures arranged relative to the viable and non-viable portions of the virtual viability model.

Referring now to FIG. 7C, the visual content VC is similar to as is depicted in FIG. 7B but also shows the selected third virtual stabilizer model 100C positioned as depicted in FIG. 6D. This illustrates that the visualization program 36 may be configured to identify the different fixation approaches 38 based at least partially on the arrangement of the plurality of virtual aperture 104 of the selected stabilizer model 100C arranged within the virtual reference frame VRF. Here in FIG. 7C, at least one virtual aperture 104 is disposed within each of the regions of the virtual viability model 44 depicted as the superior viability portion 46S, the first and second inferior viability portions 46IA, 46IB, and the non-viable portion 48. This concept is also depicted in FIG. 7D, which shows the virtual viability model 44 presented differently, using discrete trajectories each passing through specific virtual apertures 104 instead of regions to depict the viable portions 46, and using a "barrier indicia" passing through one of the virtual apertures 104 to depict the non-viable portion 48.

Figure 7D:
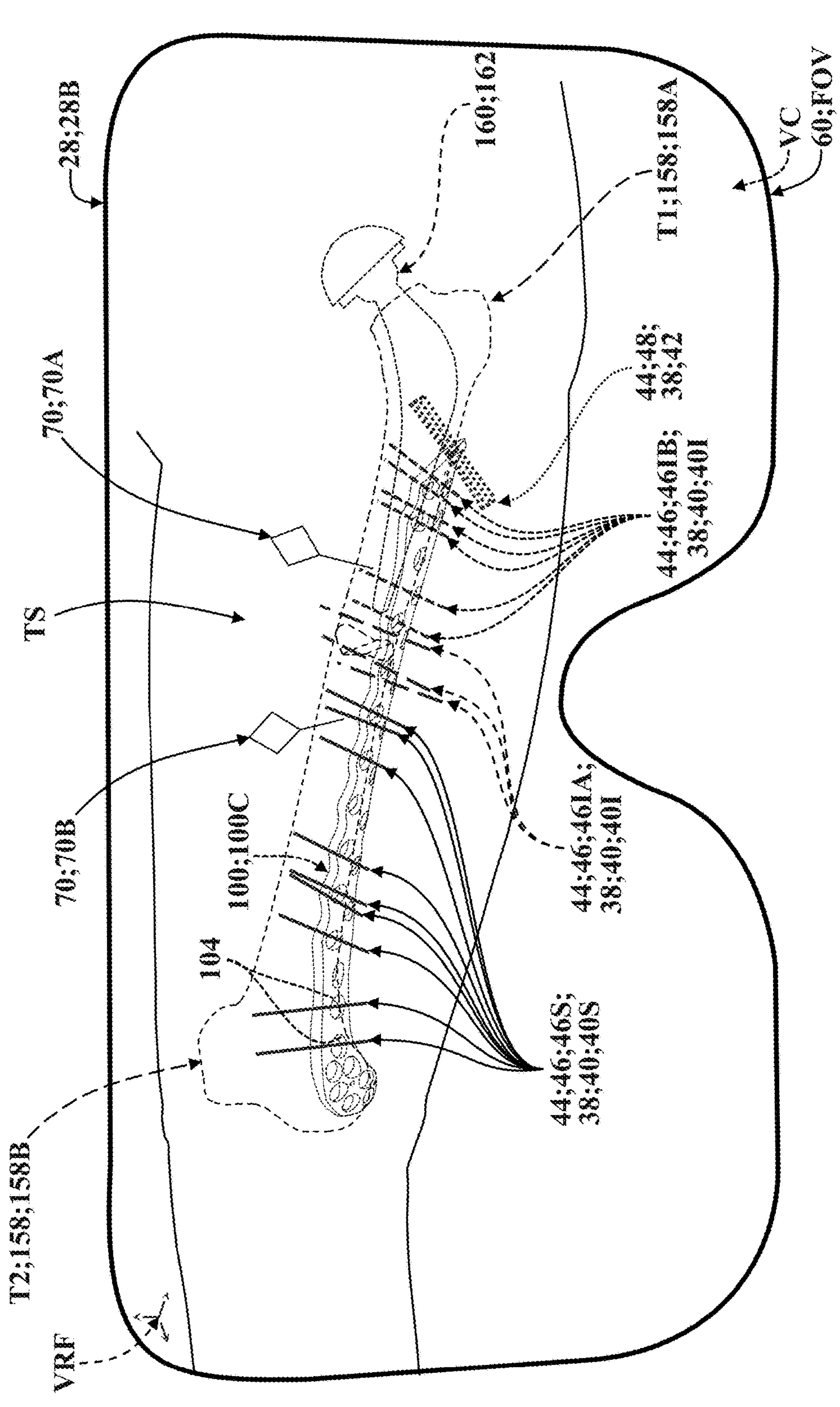
FIG. 7D is another partial perspective view of the patient's anatomy orientated as depicted in FIGS. 7A-7C, shown as viewed through the head-mountable display unit displaying portions of the visual content of FIG. 7C, with the viable portions of the virtual viability model displayed as trajectories associated with viable fixation approaches passing through virtual apertures of the virtual stabilizer model, and with the non-viable portions of the virtual viability model displayed as barrier indicia associated with non-viable fixation approaches adjacent to virtual apertures of the virtual stabilizer model.

Thus, it will be appreciated that in some embodiments (e.g., as depicted in FIG. 7D) the visualization program 36 is configured to arrange the virtual viability model 44 within the virtual reference frame VRF such that at least one of the one or more viable portions 46 of the virtual viability model 44 aligns with one of the plurality of virtual apertures 104 of the selected virtual stabilizer model 100 (here, the third virtual stabilizer model 100C). Here, the visualization program 36 may be further configured to render at least a portion of the selected virtual stabilizer model 100 in the visual content VC displayed by the display unit 28 overlaid onto the patient's anatomy within the field of view FOV to assist the user in visualizing one or more of the plurality of virtual apertures 104 of the selected stabilizer model 100, with at least one virtual aperture 104 defining a viable portion 46 of the virtual viability model 44 and/or with at least one virtual aperture 104 defining a non-viable portion 48 of the virtual viability model 44.

In some embodiments, the visualization program 36 may be configured to render the virtual viability model 44 in the visual content VC displayed by the display unit 28 overlaid onto the patient's anatomy within the field of view FOV to assist the user in visually distinguishing between one or more of: one or more superior fixation approaches 40S rendered as superior viability portions 46S of the virtual viability model, one or more inferior fixation approaches 40I rendered as inferior viability portions 46IA, 46IB of the virtual viability model 44, and one or more non-viable fixation approaches 42 rendered as non-viable portions 48 of the virtual viability model 44. Other configurations are contemplated, and it will be appreciated that the virtual viability model 44 could be configured in a number of different ways to differentiate between viable portions 46 and/or non-viable portions 48, including rendering or otherwise presenting visual content VC in different colors, shapes, shadings, outlines, arrows or other indicia representing direction and/or distance, and the like. By way of non-limiting example, green-colored superior viability portions 46S could indicate where fixation elements 24 can be placed without specific restrictions, orange-colored inferior viability portions 46IA, 46IB could indicate where fixation elements 24 can be placed conditionally (e.g., with limited lengths or in certain directions), and red-colored non-viable portions 48 could indicate where fixation elements 24 should not be placed due to collisions with implanted components 162. It will be appreciated that the configuration of the virtual viability model 44 could also be based on or otherwise complimented by information associated with the virtual patient models 158, such as where a virtual patient model 158 of a bone is textured as a "heat map" with different colors indicative of bone density or other characteristics that could be determined using patient-specific imaging data ID. Other configurations are contemplated.

Figure 8A:
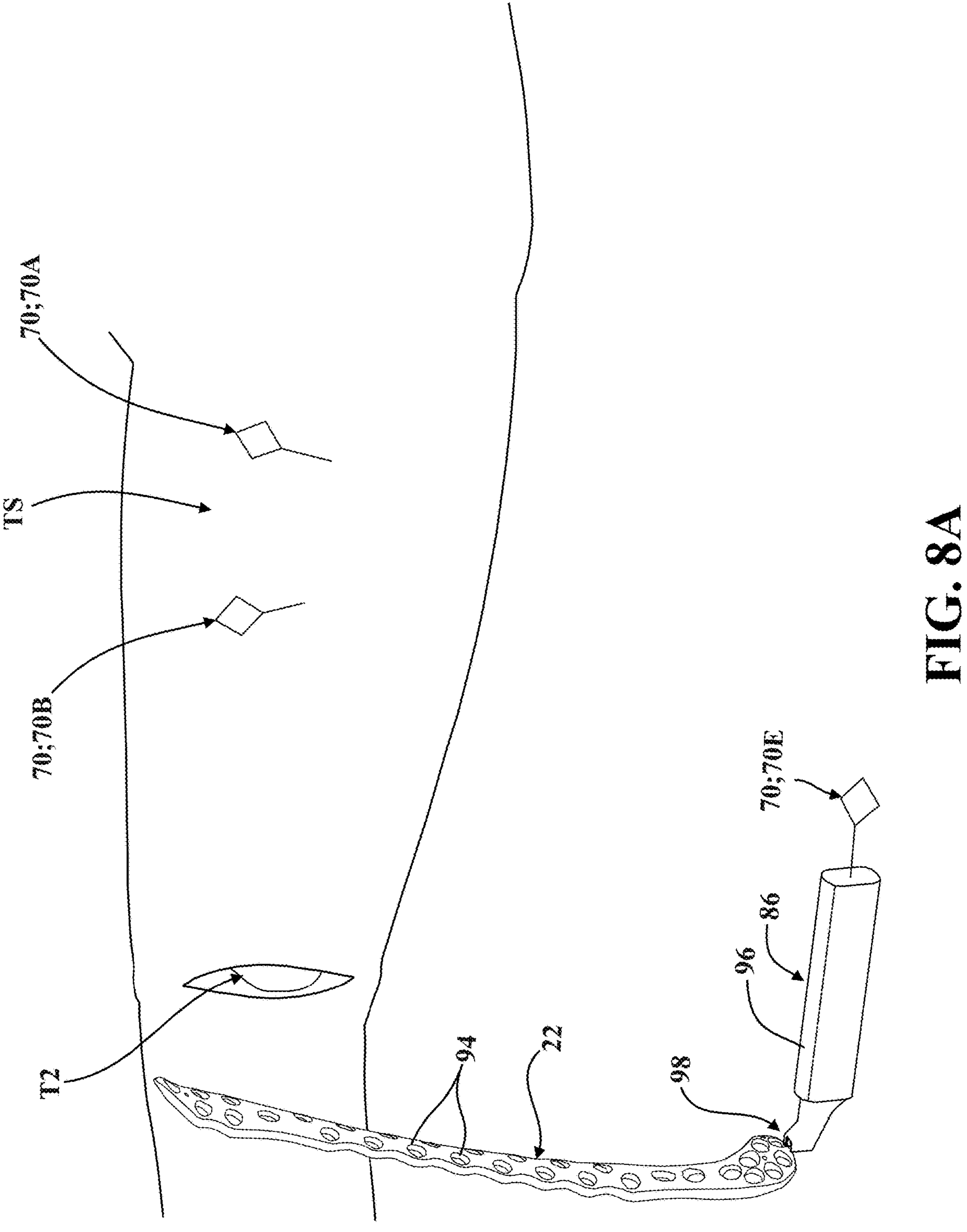
FIG. 8A is another partial perspective view of the patient's anatomy orientated as depicted in FIGS. 7A-7D, shown with a stabilizer releasably attached to the handle assembly of FIGS. 6A-6E, and with the stabilizer arranged near an incision made adjacent to the lateral epicondyle of the patient's left femur.
Figure 8B:
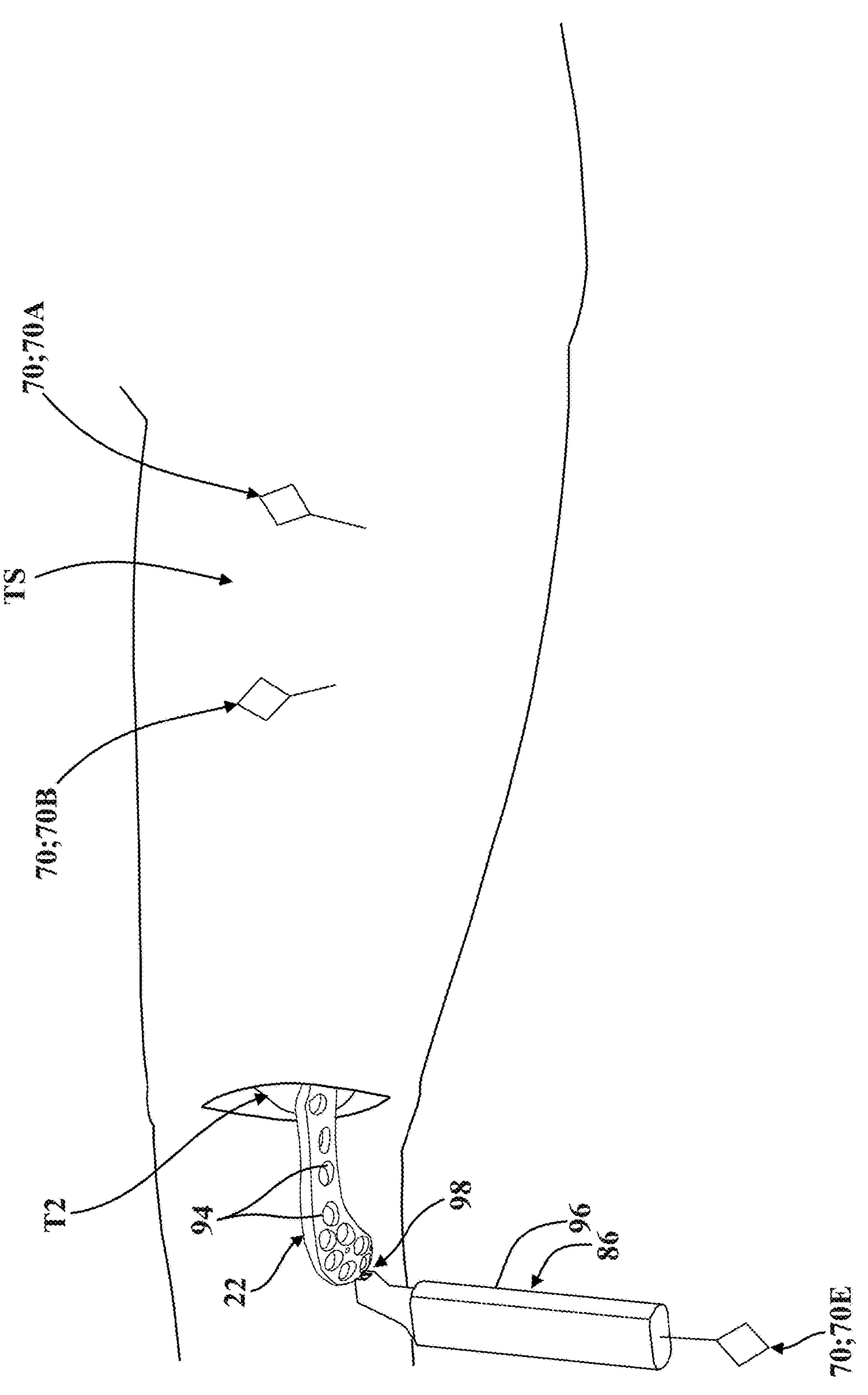
FIG. 8B is another partial perspective view of the patient's anatomy orientated as depicted in FIG. 8A, shown with the handle assembly moved to advance the stabilizer into the incision.
Figure 8C:
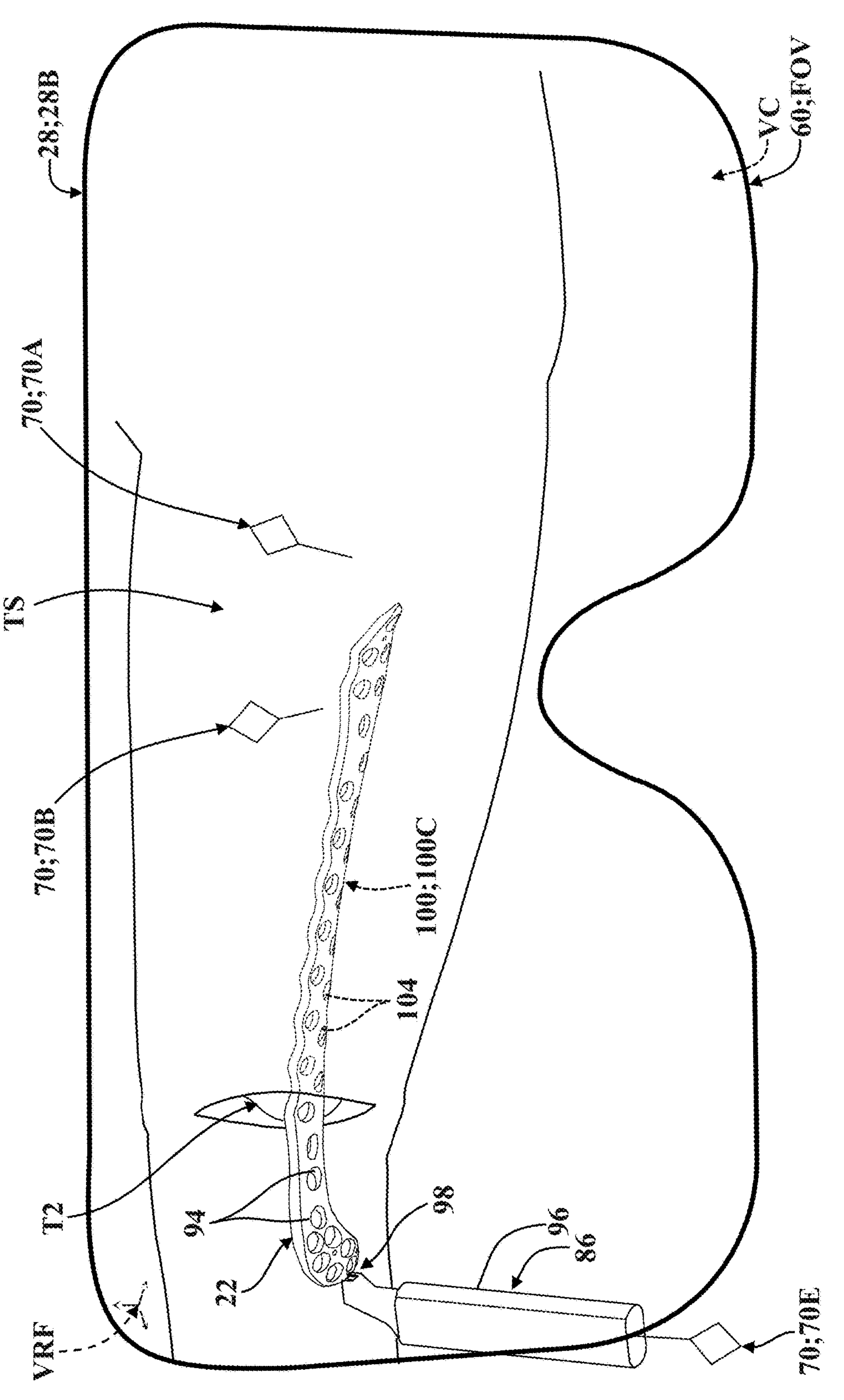
FIG. 8C is another partial perspective view of the patient's anatomy orientated as depicted in FIGS. 8A-8B, with the handle assembly and the stabilizer arranged as depicted in FIG. 8B, and shown as viewed through a head-mountable display unit displaying visual content comprising a virtual stabilizer model displayed fixed to the handle assembly to illustrate portions of the stabilizer advanced into the incision.

It will be appreciated that aspects of the concepts of "virtual trialing" described above in connection with FIGS. 6A-6E, as well as aspects of the concepts of rendering at least a portion of the virtual viability model 44 in the visual content VC displayed by the display unit 28 overlaid onto the patient's anatomy within the field of view FOV to assist the user in visually distinguishing the viable portions 46 from the non-viable portions 48 described above in connection with FIGS. 7A-7D, may also be utilized during actual execution of the surgical procedure to, among other things, facilitate tissue stabilization at the target site TS. For example, FIG. 8A depicts the patient's anatomy orientated in the same way as is depicted in FIGS. 7A-7D, but also shows the stabilizer 22 corresponding to the third virtual stabilizer model 100C selected during "virtual trialing" releasably attached to the handle assembly 86 and positioned nearby an incision made adjacent to the lateral epicondyle of the patient's left femur.

Here, FIGS. 8A-8F illustrate how aspects of the present disclosure can help the user visualize unexposed portions of the target site TS via portions of one or more virtual patient models 158 and/or virtual implant models 160 rendered as visual content VC displayed by the display unit 28 overlaid onto the patient's anatomy within the field of view FOV during insertion of the selected stabilizer 22. As demonstrated in FIG. 8B, partial insertion of the stabilizer 22 into the incision via the handle assembly 86 obscures parts of the stabilizer 22 from the field of view (e.g., behind muscle and skin). However, as is demonstrated in FIG. 8C, in some embodiments of the present disclosure, the visualization program 36 may be further configured to arrange the selected virtual stabilizer model 100 (here, the third virtual stabilizer model 100C) within the virtual reference frame VRF based on the handle location data HLD in a fixed relation RF such that the selected virtual stabilizer model 100 is rendered in the visual content VC displayed by the display unit 28 as attached to the coupler 98 of the handle assembly 86 within the field of view FOV to assist the user in visualizing the stabilizer 22 corresponding to the virtual stabilizer model 100 as releasably attached to the coupler 98 of the handle assembly 86. Put differently, the portions of the stabilizer 22 attached to the handle assembly 86 that are concealed from view (e.g., behind muscle and skin) can nonetheless be visualized by overlaying the virtual stabilizer model 100 directly over the stabilizer 22.

Figure 8D:
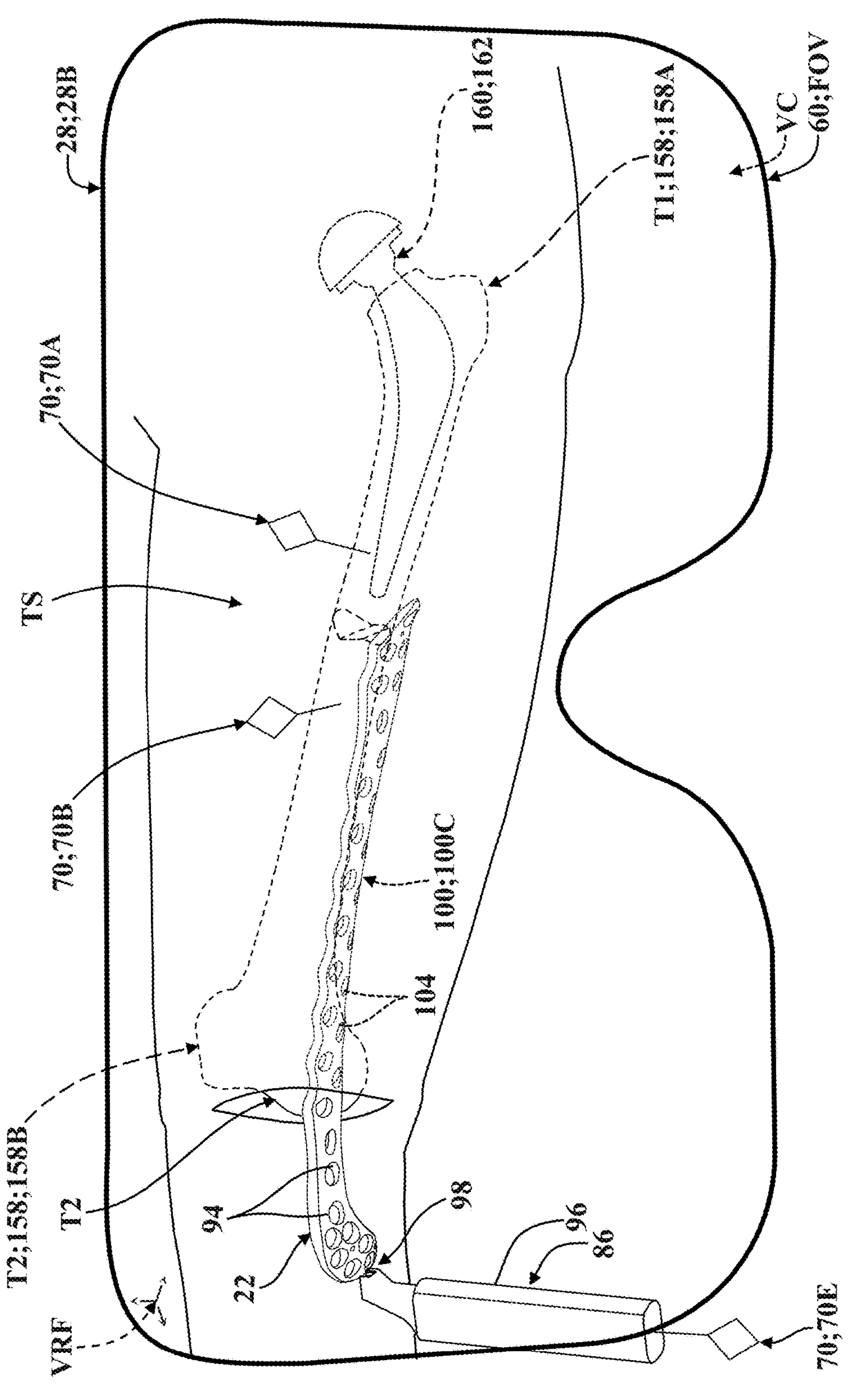
FIG. 8D is another partial perspective view of the patient's anatomy orientated as depicted in FIGS. 8A-8C, with the handle assembly and the stabilizer arranged as depicted in FIGS. 8B-8C, and shown as viewed through the head-mountable display unit displaying visual content of FIG. 8C along with the visual content of FIG. 7A.
Figure 8E:
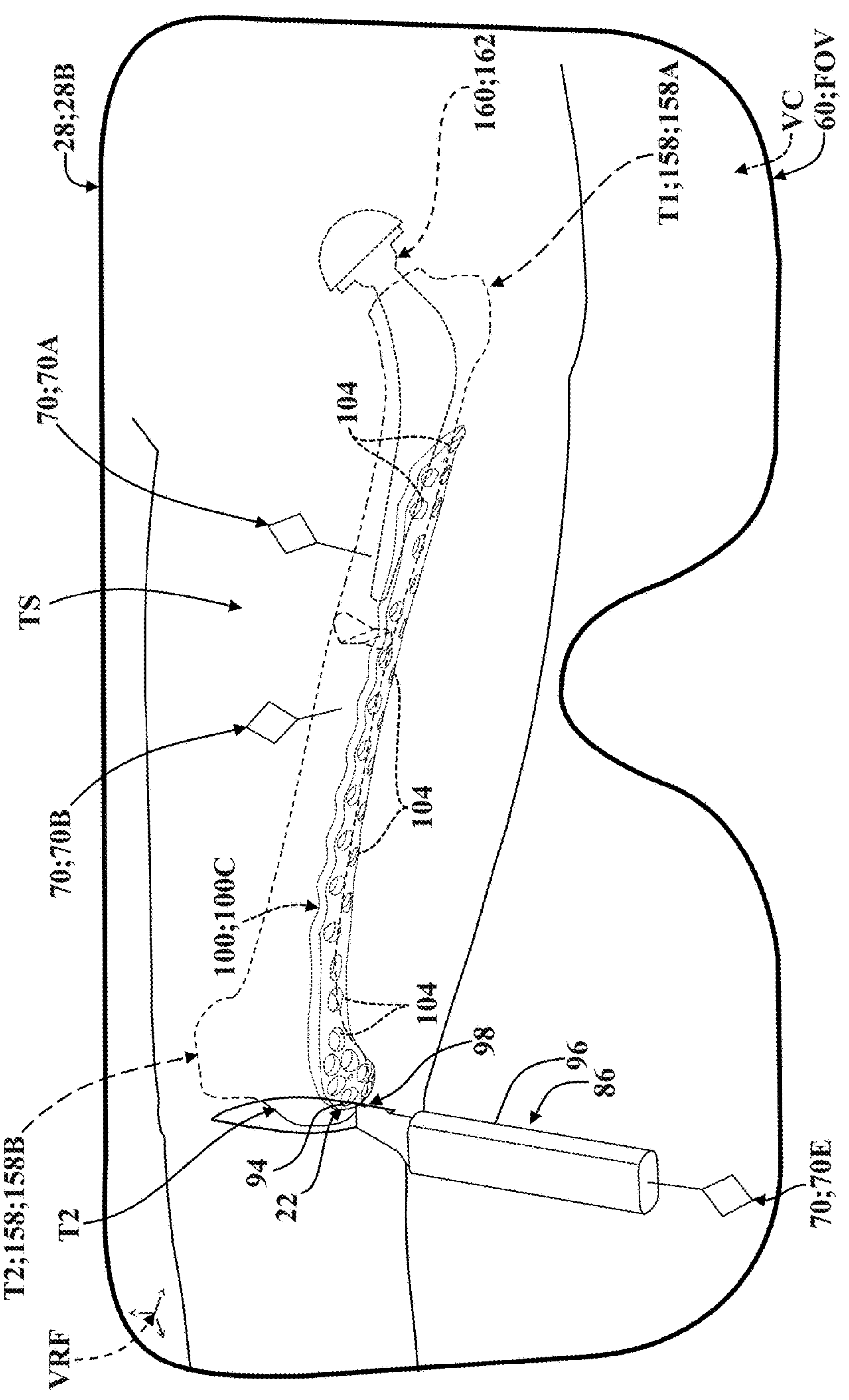
FIG. 8E is another partial perspective view of the patient's anatomy orientated as depicted in FIGS. 8A-8D, with the handle assembly moved to advance the stabilizer further into the incision, and shown as viewed through the head-mountable display unit displaying visual content of FIG. 8D.

Here too, as is demonstrated in FIG. 8D, other virtual objects such as the virtual patient models 158 and the virtual implant models 160 can also be displayed simultaneously as the user advances the stabilizer 22 toward the target site TS (see FIG. 8E) and subsequently releases the stabilizer 22 from the handle assembly 86 (see FIG. 8F), such as after installing one or more fixation elements 24 adjacent to the incision to temporarily secure the stabilizer 22 in position (not shown in detail). It will be appreciated that this "overlaying" affords the user with a significantly improved amount of visualization, in "near real-time," between the relative poses of the first and second tissue portions T1, T2 and the stabilizer 22 without necessitating that the target site TS be exposed to radiation (e.g., via fluoroscopy) and without necessitating that an excessively large incision be made to expose the target site TS.

Figure 8F:
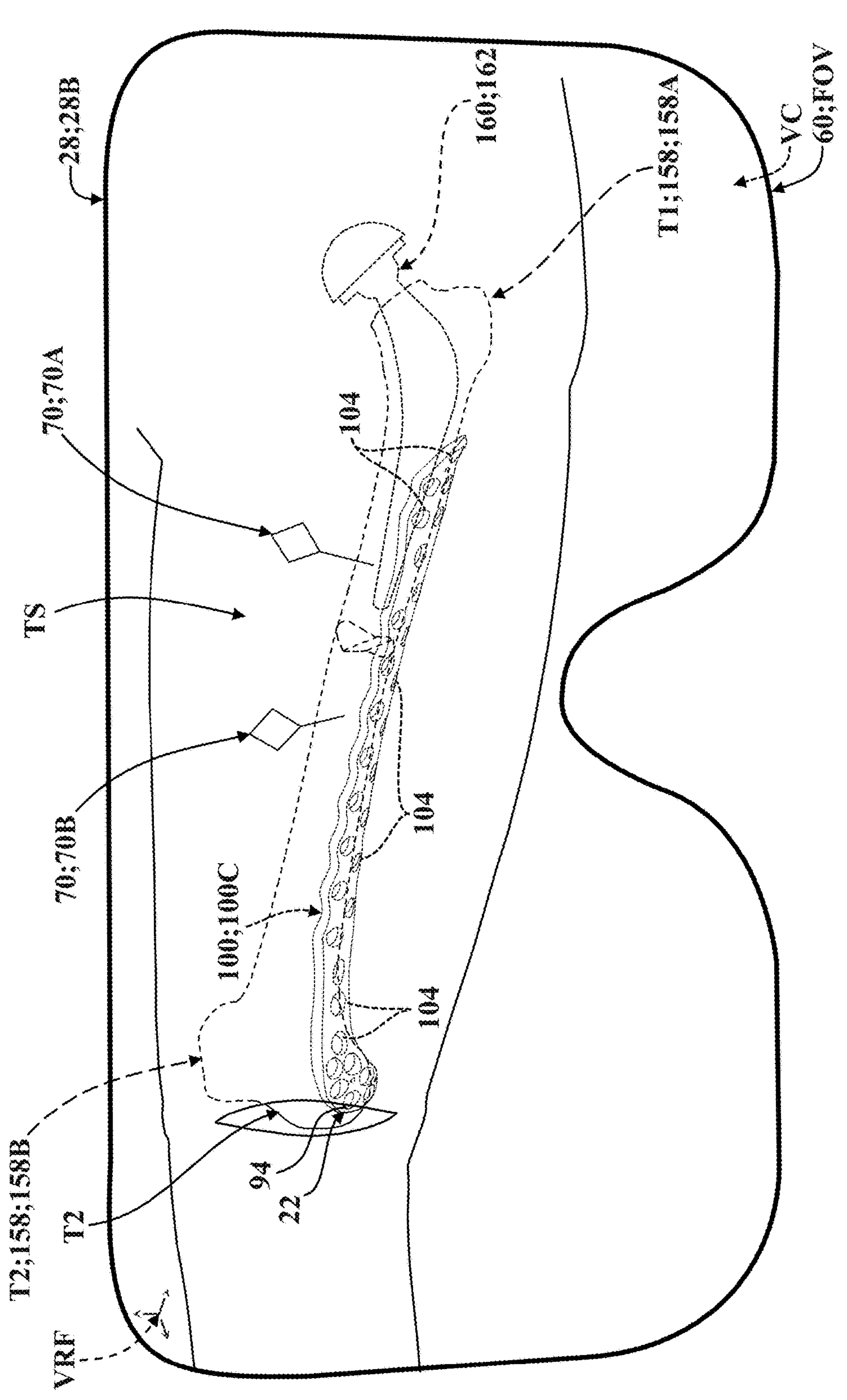
FIG. 8F is another partial perspective view of the patient's anatomy orientated as depicted in FIGS. 8A-8E, with the stabilizer arranged as depicted in FIG. 8E after being released from the handle assembly, and shown as viewed through the head-mountable display unit displaying visual content of FIGS. 8D-8E.

Referring now to FIGS. 9A-9D, the visual content VC displayed by the display unit 28 overlaid onto the patient's anatomy depicts the third virtual stabilizer model 100C, the first and second virtual patient models 158A, 158B, and the virtual implant model 160 arranged corresponding to as shown in FIG. 8F after the stabilizer 22 has been temporarily secured in position adjacent to the incision (not shown in detail). In FIG. 9A, the visual content VC also depicts the virtual viability model 44 with differently-configured viable portions 46 (as described in greater detail below), and with the non-viable portion 48 illustrated as barrier indicia corresponding to as shown in FIG. 7D.

Here too in FIGS. 9A-9D, the guide assembly 88 is shown arranged adjacent to the target site TS and, in the illustrated embodiment, the visualization program 36 is further configured to arrange the virtual axis 156 within the virtual reference frame VRF based on the guide location data GLD, and to render at least a portion of the virtual axis VA in the visual content VC displayed by the display unit 28 overlaid onto the patient's anatomy within the field of view FOV to assist the user in visualizing the virtual axis VA relative to other virtual objects within the virtual reference frame VRF, such as without limitation the one or more viable fixation approaches 40 represented by viable portions of the virtual viability model 44, the one or non-viable fixation approaches 42 represented by non-viable portions 48 of the virtual viability model 44, and the selected virtual stabilizer model 100. Here in this embodiment, the visualization program 36 is configured to arrange the virtual axis 156 within the virtual reference frame VRF based on the guide location data GLD in a fixed relation RF such that the virtual axis VA is rendered in the visual content VC displayed by the display unit 28 as aligned with the bore element 120 of the guide assembly 88 within the field of view FOV to assist the user in visualizing the virtual axis VA (compare FIGS. 9A-9C).

In the embodiment illustrated in FIGS. 9A-9C, only certain viable portions 46 of the virtual viability model 44 are depicted for illustrative purposes, including a single superior viability portion 46S, a single first inferior viability portion 46IA, and a single second inferior viability portion 46IB, each of which is configured as a "virtual drill corridor" corresponding to virtual apertures 104 of the third virtual stabilizer model 100C and each representing at least one viable fixation approach 40, rendered in the visual content VC displayed by the display unit 28 overlaid onto the patient's anatomy within the field of view FOV to assist the user in visualizing each of the "virtual drill corridors" (e.g., specific viable portions 46 of the virtual viability model 44 associated with correspondingly-specific virtual apertures 104) relative to the virtual axis 156.

In the illustrated example, each of the "virtual drill corridors" illustrating viable portions 46 of the virtual viability model comprise an least partially-frustoconical profile that is shaped and arranged to define a subset of viable fixation approaches 40 each passing through a common one of the plurality of virtual apertures 104 of the virtual stabilizer model 100. This is illustrated by comparing FIGS. 9B-9C, whereby the virtual axis 156 is shown extending through the same virtual aperture 104 of the third virtual stabilizer model 100C in two different ways which nonetheless pass through the virtual aperture 104. Here, it will be appreciated that the illustrated viable portions 46 of the virtual viability model 44 each comprise "hourglass" shaped profiles that are aligned with certain virtual apertures 104 and may be sized and/or shaped to extend from the patient's skin to a "maximum penetration depth" in tissue. Some of the "hourglass" shaped viable portions 46 may be narrower than others to indicate that a relatively smaller subset of viable fixation approaches 40 are available for a particular virtual aperture 104 (e.g., one represented having a narrower profile than others to illustrate potential interference with the implanted component 162). In some embodiments, one or more viable portions 46 could instead be depicted with generally frustoconical-shaped profiles arranged along one of the virtual apertures 104 and facing toward tissue to define a volume indicating all possible positions that a particular selected fixation element 24 could occupy (e.g., with locking poly-axial screws). The visualization program 36 may determine parameters associated with fixation elements 24, and/or may identify fixation elements 24 and/or stabilizers 22 that can be used based on the virtual viability model 44, in ways similar to as is disclosed in one or more of: U.S. Pat. No. 9,855,104, entitled "Locking Screw Length Measurement;" and U.S. Published Patent Application No. 2018/0344406, entitled "Implant Placement Planning," the disclosures of which are each hereby incorporated by reference. Other configurations are contemplated, including without limitation those disclosed in other publications referenced herein.

Here too, it will be appreciated that the specific shape, profile, and/or configuration of the viable portions 46 may be of a number of different styles, colors, and the like with different types of shading and/or outlines to help differentiate from each other or to otherwise assist the user in clearly visualizing fixation approaches 38. By way of non-limiting example, instead of "hourglass" shapes, one or more viable portions 46 could be configured as "rings" or "circles" that are displayed projected onto the patient's skin to assist the user in initially placing an incision along a viable fixation approach 40. It is also contemplated that the viable portions 46 could dynamically change based on the relative position of the virtual axis 156, such as to differentiate between a superior fixation approach 40S (e.g., along a neutral drilling axis) and an otherwise viable fixation approach 40 in near-real time as the user repositions the guide assembly 88 (e.g., by changing the color of the viable portion 46 from green to orange when the user moves the guide assembly 88 away from the neutral drilling axis). Furthermore, while the above examples relate to positioning of the guide assembly 88 relative to the target site TS to assist the user in drilling pilot holes (e.g., with a drill bit rotated within the bore element 120) or otherwise rotating fixation elements 24 along penetration trajectories PT to approach and engage against tissue, it will be appreciated that other types of tools or surgical instruments could be used within the scope of the present disclosure to assist the user in visualizing viable fixation approaches 40 (e.g., a tracked "wire driver" with "K-wire" fixation elements 24). Other configurations are contemplated.

Figure 9D:
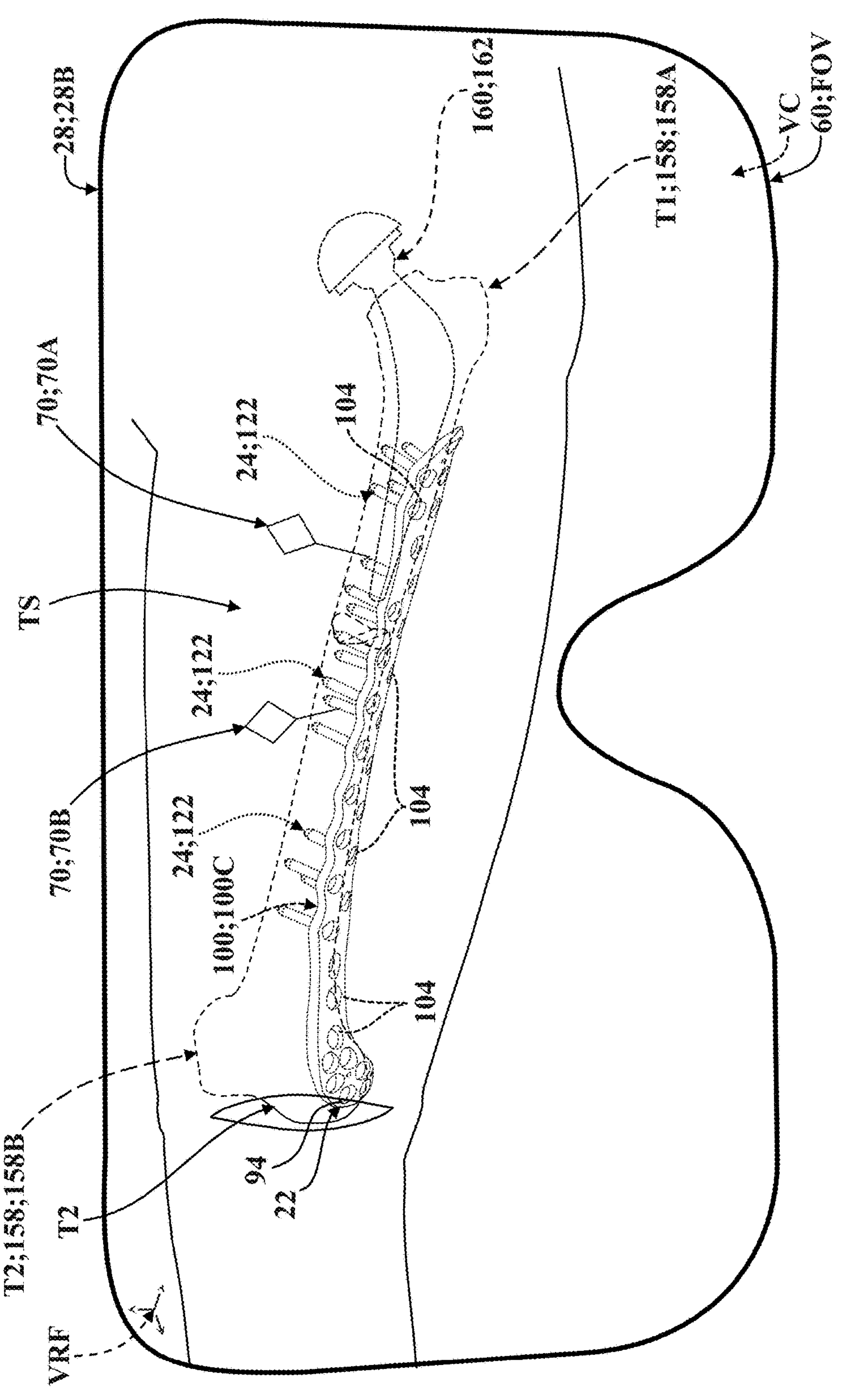
FIG. 9D is another partial perspective view of the patient's anatomy orientated as depicted in FIGS. 9A-9B, shown as viewed through the head-mountable display unit displaying the visual content of FIG. 8F along with a plurality of virtual fixation elements arranged with respect to virtual apertures of the virtual stabilizer model to illustrate a corresponding plurality of fixation elements arranged with respect to apertures of the stabilizer.

Referring now to FIG. 9D, in addition to displaying the virtual stabilizer model 100, the virtual patient models 158, and the virtual implant models 160 arranged within the virtual reference frame VRF, as noted above, the visualization program 36 may also be configured to at least partially display virtual fixation element models 122, either based on confirmed positions/orientations observed intraoperatively (e.g., via imaging systems 50), or based on intended placement of fixation elements 24 in specific apertures 94 of the selected stabilizer 22. Here, by rendering at least a portion of one or more virtual fixation element models 122 as visual content VC displayed by the display unit 28 overlaid onto the patient's anatomy, the user can verify, validate, or otherwise refine certain steps of the surgical plan intraoperatively (e.g., adjust a particular fixation approach 38 based on the placement of a previous fixation element 24). Other configurations are contemplated.

Referring now to FIGS. 10A-10F, as noted above, the present disclosure can be utilized in connection with assisting the user in visualizing various aspects related to tissue stabilization utilizing a number of different types of stabilizers 22 and/or fixation elements 24 in connection with both internal fixation FI and external fixation FE methodologies, techniques, and the like. In FIG. 10A, the visual content VC displayed with the head-mountable display unit 28B overlaid onto the patient's anatomy at the target site TS is similar to as was described above in connection with FIG. 7B. However, in the representative illustrations shown in FIG. 10A-10F, the user employs aspects of the present disclosure to facilitate assembly of an external fixation frame 170 (see FIGS. 10E-10F) according such as to the Ilizarov technique. As noted above, FIGS. 10A-10F depict the target site TS with a diaphyseal periprosthetic fracture to the patient's left femur which is similar to the target site TS described in connection with FIGS. 5A-9D. Those having ordinary skill in the art will appreciate that external fixation FE systems are generally employed in connection with treating tissue at other types of target sites TS, such as those which do not involve an implanted component 162. Nevertheless, FIGS. 10A-10F illustrate the same diaphyseal periprosthetic fracture as described above in connection with FIGS. 5A-9D in order to, among other things, afford clarity and consistency with respect to how the virtual viability model 44 can be defined and utilized, irrespective of whether external fixation FE systems or internal fixation IF systems are utilized to treat tissue at the target site TS (compare FIG. 10A with FIG. 7B).

Here too in FIG. 10A, the visualization program 36 renders the virtual viability model 44 to depict viable portions 46 and non-viable portions 48 as regions (or "areas") delineated from each other as comprising a total of four exemplary portions, including three viable portions 46 associated with viable fixation approaches 40, and one non-viable portion 48 associated with non-viable fixation approaches 42; one of the viable portions 46 comprises a superior viability portion 46A associated with one or more superior fixation approaches 40S, while the other two viable portions 46 comprise first and second inferior viability portions 46IA, 46IB associated with one or more inferior fixation approaches 40I. Because the visualization program 36 can identify fixation approaches 38 and render the virtual viability model 44 via, among other things, the relative orientation of different tissue portions T1, T2 and/or implanted components 162 based on patient-specific imaging data ID, it will be appreciated that identifying viable fixation approaches 40 does not necessarily require consideration of the geometry of a selected virtual stabilizer model 100 to generate the virtual viability model 44.

Put differently, and as is shown in FIG. 10A, the visualization program 36 may arrange the virtual viability model 44 to depict generalized regions that comprise viable portions 46 (including those of different types) and non-viable portions 48 to assist the user in visualizing viable fixation approaches 40 initially without any consideration to the type of stabilizer 22 to be utilized. It will be appreciated that this configuration affords significant advantages when used in connection with external fixation EF tissue stabilization methodologies, in that the visualization of the virtual viability model 44 promotes improved accuracy of fixation element 24 engagement with tissue, and thereby contributes to improved ease-of-assembly of external fixation frames 170 to secure fixation elements 24 used to, among other things, reduce complex fractures, correct bone deformities, stabilize joints while maintaining a certain amount of range of motion, perform arthrodesis and limb-salvage, and the like.

While a number of different types of external fixation FE systems are contemplated by the present disclosure, FIGS. 10A-10F illustrate one type of external fixation frame 170 that may be constructed according to the present disclosure. In FIG. 10B, the user has placed one ring member 130 around the patient's left thigh, the states of which are tracked by the navigation system 68 via the first stabilizer tracker 70G. As shown in FIG. 10C, the visualization program 36 may be configured to enable the selection of one or more virtual stabilizer models 100 (more specifically, a virtual ring member model 146) for arrangement within the virtual reference frame VRF which defines a plurality of virtual mounts 148 arranged relative to a corresponding plurality of mounts 132 defined by the stabilizer 22 (e.g., the ring member 130) that are each shaped to receive a lock 138 to secure a respective fixation element 24 (see FIG. 10E). As noted above, the navigation system 68 (as well as various other parts of the surgical system 20) can be configured in various ways, and it will be appreciated that certain trackers 70 are depicted in FIGS. 10A-10F for illustrative purposes.

As shown in FIGS. 10C-10D, in some embodiments, the visualization program 36 affords the ability to conduct "virtual trialing" or "virtual construction" of the external fixation frame 170 by, among other things, identifying the plurality of different fixation approaches 38 based on the arrangement of the plurality of virtual mounts 148 of a selected virtual stabilizer model 100 within the virtual reference frame VRF. Here, the visualization program 36 is also configured to render at least a portion of the selected virtual stabilizer model 100 in the visual content VC displayed by the display unit 28 overlaid onto the patient's anatomy within the field of view FOV to assist the user in visualizing one or more of the plurality of virtual mounts 148 of the selected virtual stabilizer model 100. In this way, the visualization program 36 can help the user optimize the construction of the external fixation frame 170, such as by adjusting the virtual viability model 44 based on the proposed arrangement of different ring members 130, connecting rods 134, and the like, and/or by suggesting specific positions for components of the external fixation frame 170 to be utilized at one or more levels in order to achieve optimized stability. Here, the visualization program 36 may enable construction of external fixation frames 170, or may otherwise facilitate tissue stabilization or reconstruction according to various computer-assisted surgical techniques similar to as is disclosed in one or more of: U.S. Pat. No. 10,082,384, entitled "Systems and Methods for Detecting Fixation Frame Parameters;" and U.S. Patent Application Publication No. 2017/0281233, entitled "Software for Use with Deformity Correction;" the disclosures of which are each hereby incorporated by reference. Other configurations are contemplated, including without limitation those disclosed in other publications referenced herein.

As noted above, the present disclosure is also directed toward various methods of treating tissue of the patient's anatomy at the target site TS, with stabilizers 22 and fixation elements 24, based on patient-specific imaging data ID. In one embodiment, the method comprises: generating the patient location data PLD associated with a location of at least a portion of the patient's anatomy; identifying the plurality of different fixation approaches 38 for the fixation element 24 to engage tissue and secure the stabilizer 22 relative to the target site TS, with the plurality of different fixation approaches 38 delineated between one or more viable fixation approaches 40 and one or more non-viable fixation approaches 42 based on the patient-specific imaging data ID; arranging the virtual viability model 44 within the virtual reference frame VRF based on the patient location data PLD, the virtual viability model 44 comprising at least one of: one or more viable portions 46 associated with the viable fixation approaches 40; and one or more non-viable portions 48 associated with the non-viable fixation approaches 42; providing the display unit 28 to display visual content VC overlaid onto the patient's anatomy within the field of view FOV observable by a user; and rendering at least a portion of the virtual viability model 44 in the visual content VC displayed by the display unit 28 overlaid onto the patient's anatomy within the field of view FOV to assist the user in visualizing at least one of: the one or more viable fixation approaches 40; and the one or more non-viable fixation approaches 42.

In some embodiments, the method further comprises the steps of: arranging one or more virtual patient models 158 within the virtual reference frame VRF based on the patient location data PLD; and rendering at least a portion of the one or more virtual patient models 158 in the visual content VC displayed by the display unit 28 overlaid onto the patient's anatomy within the field of view FOV to assist the user in visualizing the one or more virtual patient models 158.

In some embodiments, the method further comprises the steps of: identifying one or more implanted components 162 adjacent to the target site TS based on the patient-specific imaging data ID; arranging one or more virtual implant models 160, corresponding to the one or more identified implanted components 162, within the virtual reference frame VRF based on the patient location data PLD; and rendering at least a portion of the one or more virtual implant models 160 in the visual content VC displayed by the display unit 28 overlaid onto the patient's anatomy within the field of view FOV to assist the user in visualizing the one or more virtual implant models adjacent to an unexposed portion of the target site TS.

In some embodiments, the method further comprises the step of selecting one or more virtual stabilizer models 100 for arrangement within the virtual reference frame VRF with at least one of the one or more virtual stabilizer models 100 defining a plurality of virtual apertures 104 arranged relative to a corresponding plurality of apertures 94 defined by the stabilizer 22 each shaped to receive the fixation element 24 therethrough. Here, the step of identifying the plurality of different fixation approaches 38 is based at least partially on the arrangement of the plurality of virtual apertures 104 of a selected virtual stabilizer model 100 within the virtual reference frame VRF.

In some embodiments, the method further comprises the steps of: providing the handle assembly 86 with the handle grip 96 configured for engagement by the user and a coupler 98 to facilitate releasable attachment of the stabilizer 22; generating handle location data HLD associated with a location of at least a portion of the handle assembly 86; and arranging the selected virtual stabilizer model 100 within the virtual reference frame VRF based on the handle location data HLD. Here, in some embodiments, the step of arranging the selected virtual stabilizer model 100 with this virtual reference frame VRF may be based on a fixed relation RF such that the selected virtual stabilizer model 100 is rendered in the visual content VC displayed by the display unit 28 as attached to the coupler 98 of the handle assembly 86 within the field of view FOV to assist the user in visualizing the stabilizer 22 corresponding to the selected virtual stabilizer model 100 as releasably attached to the coupler 98 of the handle assembly 86. However, in some embodiments, the step of arranging the selected virtual stabilizer model 100 with this virtual reference frame VRF may be based on an offset relation RO such that the selected virtual stabilizer model 100 is rendered in the visual content VC displayed by the display unit 28 as offset from the coupler 98 of the handle assembly 86 within the field of view FOV to assist the user in visualizing the stabilizer 22 corresponding to selected virtual stabilizer model 100 as offset from the coupler 98 of the handle assembly 86.

In this way, the surgical system 20, the visualization program 36, and the various methods and computer-implemented techniques of the present disclosure afford significant advantages in connection with treating tissue in connection with a number of different types of surgical interventions by assisting the user in visualizing various virtual objects displayed by the display unit 28 in near-real time overlaid onto the patient's anatomy (e.g., via mixed reality and/or augmented reality). By affording the user with the ability to visualize the virtual viability model 44, the virtual patient models 158 representing portions of the patient's own anatomy, the virtual implant models 160 representing previously implanted components 162, and/or one or more virtual stabilizer models 100 and/or virtual fixation element models 122 as visual content VC displayed overlaid onto the patient's anatomy adjacent to the unexposed target site TS, the user can significantly reduce the likelihood of and risks associated with unnecessary tissue damage while driving fixation elements 24 into tissue and/or when attaching or otherwise positioning stabilizers 22. Furthermore, the surgical system 20, the visualization program 36, and the various methods and computer-implemented techniques of the present disclosure afford the user with the ability to visualize visual content VC directly overlaid onto corresponding physical components or tissues which would otherwise be obstructed from view without necessitating the use of fluoroscopy at the target site TS. This also allows the user to conduct "virtual trialing" of different types of stabilizers 22 without exposing the target site TS, which promotes a significant reduction in the risk of infection and can result in less time spent in the operating room. This also promotes improved logistics, in that certain types of stabilizers 22 and/or fixation elements 24 may be proposed using the surgical system 20, allowing staff to obtain identified stabilizers 22 and/or fixation elements 24 during or shortly after "virtual trialing" such that they are readily available for the user after the incision is made. Similarly, the visualization program 36 can be utilized to facilitate reporting support (e.g., for use by the surgeon and/or hospital staff), such as by exporting data regarding "virtual trialing" and/or the various types of stabilizers 22 and/or fixation elements 24 utilized during the procedure. Furthermore, by using patient-specific imaging data ID, the user is able to visualize the patient's own anatomy, and can therefor readily appreciate (and visualize) patient-specific anatomical structure that may be abnormal, previously-altered, and the like.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A surgical system for use in treating tissue of a patient's anatomy based on patient-specific imaging data, the surgical system comprising:

an external fixation system including: a fixation element configured to engage bone at a target site, and a plurality of stabilizers for constructing an external fixation frame to support the fixation element;

a display unit to display visual content overlaid onto the patient's anatomy within a field of view observable by a user; and a computing device coupled to the display unit, the computing device comprising one or more processors and a non-transitory storage medium having stored thereon a visualization program that when executed by the one or more processors is configured to:

generate a virtual reference frame, identify at least one viable fixation approach for the fixation element of the external fixation system to engage bone based on the patient-specific imaging data, arrange a virtual stabilizer model within the virtual reference frame, the virtual stabilizer model being associated with one of the plurality of stabilizers of the external fixation system, and render at least a portion of the virtual stabilizer model in the visual content displayed by the display unit overlaid onto the patient's anatomy within the field of view to assist the user in constructing the external fixation frame of the external fixation system.

2. The surgical system as set forth in claim 1, wherein the visualization program is further configured to:

arrange a virtual fixation element model within the virtual reference frame, and render at least a portion of the virtual fixation element model in the visual content displayed by the display unit overlaid onto the patient's anatomy within the field of view to assist the user in constructing the external fixation frame of the external fixation system.

3. The surgical system as set forth in claim 2, wherein the visualization program is further configured to:

enable selection of one or more virtual fixation element models for arrangement within the virtual reference frame with at least one of the one or more virtual fixation element models comprising:

a virtual interface end arranged relative to a corresponding interface end defined by the fixation element, and a virtual engagement end arranged relative to a corresponding engagement end defined by the fixation element configured to engage tissue at the target site.

4. The surgical system as set forth in claim 1, wherein the visualization program is further configured to enable selection of one or more virtual stabilizer models for arrangement within the virtual reference frame.

5. The surgical system as set forth in claim 4, wherein the visualization program is further configured to:

identify at least one viable fixation approach for the fixation element to engage bone based on the patient-specific imaging data, arrange a virtual viability model within the virtual reference frame, the virtual viability model comprising one or more viable portions associated with the one or more viable fixation approaches, and render at least a portion of the virtual viability model in the visual content displayed by the display unit overlaid onto the patient's anatomy within the field of view to assist the user in visualizing the one or more viable fixation approaches.

6. The surgical system as set forth in claim 5, wherein at least one of the one or more virtual stabilizer models defines a plurality of virtual apertures arranged relative to a corresponding plurality of apertures defined by one of the plurality of stabilizers, the plurality of apertures each shaped to receive the fixation element therethrough.

7. The surgical system as set forth in claim 6, wherein the visualization program is further configured to identify the at least one viable fixation approach based at least partially on the arrangement of the plurality of virtual apertures of a selected virtual stabilizer model within the virtual reference frame.

8. The surgical system as set forth in claim 7, wherein the visualization program is further configured to arrange the virtual viability model within the virtual reference frame such that at least one of the one or more viable portions of the virtual viability model aligns with one of the plurality of virtual apertures of the selected virtual stabilizer model.

9. The surgical system as set forth in claim 7, wherein the visualization program is further configured to render at least a portion of the selected virtual stabilizer model in the visual content displayed by the display unit overlaid onto the patient's anatomy within the field of view to assist the user in visualizing one or more of the plurality of virtual apertures of the selected virtual stabilizer model.

10. The surgical system as set forth in claim 7, wherein the visualization program is further configured to arrange the virtual viability model within the virtual reference frame such that at least one of the plurality of virtual apertures of the selected virtual stabilizer model defines a viable portion of the virtual viability model.

11. The surgical system as set forth in claim 7, wherein the visualization program is further configured to:

further delineate at least one identified viable fixation approach as either a superior fixation approach or an inferior fixation approach based on the patient-specific imaging data, and arrange the virtual viability model within the virtual reference frame such that the one or more viable portions comprise one or more of: a superior viability portion associated with one or more superior fixation approaches; and an inferior viability portion associated with one or more inferior fixation approaches.

12. The surgical system as set forth in claim 11, wherein the visualization program is further configured to render the virtual viability model in the visual content displayed by the display unit overlaid onto the patient's anatomy within the field of view to assist the user in visually distinguishing between one or more of:

one or more superior fixation approaches rendered as superior viability portions of the virtual viability model, and one or more inferior fixation approaches rendered as inferior viability portions of the virtual viability model.

13. The surgical system as set forth in claim 1, further comprising a localizer coupled to the computing device and configured to generate patient location data associated with a location of at least a portion of the patient's anatomy.

14. The surgical system as set forth in claim 13, further comprising a handle assembly with a handle grip configured for engagement by the user and a coupler to facilitate releasable attachment to at least one of the plurality of stabilizers;

wherein the localizer is further configured to generate handle location data associated with a location of at least a portion of the handle assembly; and wherein the visualization program is further configured to:

arrange the virtual stabilizer model within the virtual reference frame based on the handle location data, arrange one or more virtual patient models within the virtual reference frame based on the patient location data, and render at least a portion of the one or more virtual patient models and at least a portion of the virtual stabilizer model in the visual content displayed by the display unit overlaid onto the patient's anatomy within the field of view to assist the user in visualizing the virtual stabilizer model.

15. The surgical system as set forth in claim 13, further comprising a guide assembly with a guide grip configured for engagement by the user and a bore element defining a penetration trajectory;

wherein the localizer is further configured to generate guide location data associated with a location of at least a portion of the guide assembly; and wherein the visualization program is further configured to:

arrange a virtual axis corresponding to the penetration trajectory within the virtual reference frame based on the guide location data, and render at least a portion of the virtual axis in the visual content displayed by the display unit overlaid onto the patient's anatomy within the field of view to assist the user in visualizing the virtual axis.

16. The surgical system as set forth in claim 15, wherein the visualization program is further configured to arrange the virtual axis within the virtual reference frame based on the guide location data in a fixed relation such that the virtual axis is rendered in the visual content displayed by the display unit as aligned with the bore element of the guide assembly within the field of view to assist the user in visualizing the virtual axis.

17. The surgical system as set forth in claim 1, wherein the visualization program is further configured to:

enable selection of one or more virtual stabilizer models for arrangement within the virtual reference frame with at least one of the one or more virtual stabilizer models defining a plurality of virtual mounts arranged relative to a corresponding plurality of mounts defined by one of the plurality of stabilizers, the plurality of mounts each shaped to receive a lock to secure to a respective fixation element;

identify the at least one viable fixation approach based at least partially on the arrangement of the plurality of virtual mounts of a selected virtual stabilizer model within the virtual reference frame; and render at least a portion of the selected virtual stabilizer model in the visual content displayed by the display unit overlaid onto the patient's anatomy within the field of view to assist the user in visualizing one or more of the plurality of virtual mounts of the selected virtual stabilizer model.

18. The surgical system as set forth in claim 1, wherein the visualization program is further configured to identify a plurality of different tissue portions adjacent to the target site based on the patient-specific imaging data.

19. The surgical system as set forth in claim 18, wherein the visualization program is further configured to differentiate one or more of the plurality of different tissue portions into one or more of:

at least one viable tissue region defined by intended engagement with the fixation element along one or more viable fixation approaches, and at least one non-viable tissue region defined by intended avoidance with the fixation element.

20. The surgical system as set forth in claim 1, wherein the visualization program is further configured to:

identify one or more implanted components adjacent to the target site based on the patient-specific imaging data;

arrange one or more virtual implant models, corresponding to the one or more identified implanted components, within the virtual reference frame; and render at least a portion of the one or more virtual implant models in the visual content displayed by the display unit overlaid onto the patient's anatomy within the field of view to assist the user in visualizing the one or more virtual implant models adjacent to an unexposed portion of the target site.

* * * * *